(12) United States Patent
Staines et al.

(10) Patent No.: US 7,501,231 B2
(45) Date of Patent: Mar. 10, 2009

(54) METHODS AND COMPOSITIONS FOR CRYOPRESERVATION OF DISSOCIATED PRIMARY ANIMAL CELLS

(75) Inventors: William Staines, Ottawa (CA); Anthony Krantis, Ottawa (CA)

(73) Assignee: University of Ottawa, Ottawa (CA)

( * ) Notice: Subject to any disclaimer, the term of this patent is extended or adjusted under 35 U.S.C. 154(b) by 335 days.

(21) Appl. No.: 10/472,461

(22) PCT Filed: Mar. 25, 2002

(86) PCT No.: PCT/CA02/00393

§ 371 (c)(1),
(2), (4) Date: Dec. 19, 2003

(87) PCT Pub. No.: WO02/076206

PCT Pub. Date: Oct. 3, 2002

(65) Prior Publication Data

US 2004/0242495 A1  Dec. 2, 2004

Related U.S. Application Data

(60) Provisional application No. 60/278,492, filed on Mar. 23, 2001.

(51) Int. Cl.
*A01N 1/02* (2006.01)
*C12N 5/02* (2006.01)
(52) U.S. Cl. .................................. 435/1.3; 435/392
(58) Field of Classification Search .............. None
See application file for complete search history.

(56) References Cited

U.S. PATENT DOCUMENTS

| | | | |
|---|---|---|---|
| 4,927,762 A | 5/1990 | Darfler | |
| 5,328,821 A | 7/1994 | Fisher et al. | |
| 5,849,584 A | 12/1998 | Coon et al. | |
| 5,849,585 A | 12/1998 | Mather et al. | |
| 5,942,437 A | 8/1999 | Sanberg et al. | |
| 5,958,767 A | 9/1999 | Snyder et al. | |
| 5,968,829 A | 10/1999 | Carpenter | |
| 5,972,923 A | 10/1999 | Simpkins et al. | |
| 6,037,175 A | 3/2000 | Cameron et al. | |
| 6,140,116 A | 10/2000 | Dinsmore | |
| 6,140,123 A | 10/2000 | Demetriou et al. | |
| 2002/0110546 A1* | 8/2002 | Major et al. | 424/93.21 |

FOREIGN PATENT DOCUMENTS

WO   WO 99/35242   7/1999

OTHER PUBLICATIONS

Gibco Catalog, pp. 93-94 (1992).*
Culture of Animal Cells: A Manual of Basic Techniques, ed. Freshney, Wiley-Liss, Inc. pp. 297-299, 301 (1994).*
Current Protocols in Cell Biology, Eds. Bonifacino et al., Use of Antibiotics in Media (1998).*
Xie et al., "Survival of Hippocampal and Cortical neurons in a Mixture of MEM+ and B27-Supplemented Neurobasal Medium", Free Radical Biology & Medicine 28 (5) : 665-672 (2000).*
Gray et al., Society for Neuroscience Abstracts, (2001), 27 (2) : 2045.*
Brewer et al., "Optimized Survival of Hippocampal Neurons in B27-Supplemented Neruobasal, a New Serum-free Medium Combination", J. Neuroscience Research 35 : 567-576 (1993).*
Han et al., "Protection against glutamate-induced cytotoxicity in C6 glial cells by thiol antioxidants", American Journal of Physiology 273 (5 pt. 2) : R1771-R1778 (1997).*
Corrigall et al., Electrophysiological studies of fetal mouse olfactory bulb explants during development of synaptic functions in culture.J Neurobiol. Nov. 1976;7(6):521-36.
Donat et al., Heme oxygenase immunoreactive neurons in the rat intestine and their relationship to nitrergic neurons. J Auton Nerv Syst. Jul. 7, 1999;77(1):4-12.
Hashimoto et al., Isolation and characterisation of fetal bovine brain cells in primary culture. Res Vet Sci. Aug. 2000;69(1):39-46.
Jessen et al., The enteric nervous system in tissue culture. I. Cell types and their interactions in explants of the myenteric and submucous plexuses from guinea pig, rabbit and rat.Brain Res. Feb. 28, 1983;262(1):17-35.
Matini et al., Neurochemical differentiation of rat enteric neurons during pre- and postnatal life. Cell Tissue Res. Apr. 1997;288(1):11-23.
Nishi and Willard, Neurons dissociated from rat myenteric plexus retain differentiated properties when grown in cell culture. I. Morphological properties and immunocytochemical localization of transmitter candidates.Neuroscience. Sep. 1985;16(1):187-99.
Schafer et al., Morphological changes of the myenteric plexus during early postnatal development of the rat. Anat Rec. Sep. 1, 1999;256(1):20-8.
Swales et al., Cryopreservation of rat and mouse hepatocytes. I. Comparative viability studies. Drug Metab Dispos. Nov. 1996;24(11):1218-23.

* cited by examiner

*Primary Examiner*—Sandra E Saucier
(74) *Attorney, Agent, or Firm*—Wilmer Cutler Pickering Hale and Dorr LLP

(57) ABSTRACT

The invention can be summarized as follows. The present invention provides cell culture compositions and cell cryopreservation compositions for culturing and cryopreserving enteric system (ENS) neurons and central nervous system (CNS) neurons. The present invention also provides a method of culturing and cryopreserving ENS and CNS cells. The compositions of the present invention comprise nutrient medium, serum, glutamine, glucose an antibiotic and one or more of the following components: one or more mitotic inhibitors, one or more antioxidants, and a cryopreservative.

13 Claims, 36 Drawing Sheets

021100 Cortex Frozen 7 days in culture no treatment plated at 2X live density

Cortical culture: frozen 15-Feb-2000
thawed 30-May-2000
recorded 10-June-2000

Same culture without freezing: recorded 24-Feb-2000

FROZEN MOUSE CEREBELLUM
7 days in culture

Fresh Mouse Hippocampus, Postnatal day 1
7 days in vitro, Maintained in CNS plating media
Plating density 500.000 cells/ml  Batch 250601

Fresh Mouse Cortex, Embryonic day 18/19
7 days in vitro, Maintained in CNS plating media
Plating density 500.000 cells/ml  Batch 250601

Frozen Mouse Hippocampus, Embryonic day 18/19, 7 day in vitro, Maintained in CNS - ACG, Batch 250601

Immunohistochemistry:
Neurofilament marker Tuj
Neurotransmitter marker GABA

Fresh Mouse Hippocampus, Postnatal day 1
7 days in vitro, Maintained in CNS plating media
Plating density 500.000 cells/ml  Batch 250601

Fresh Mouse Cortex, Embryonic day 18/19
7 days in vitro, Maintained in CNS plating media
Plating density 500.000 cells/ml  Batch 250601

Frozen Rat Hippocampus. Embryonic day 18/19.
7 days in vitro. Maintained in Neurobasal media with B27 plus AO.
Immunohistocemistry:
green neuronal marker PGP
red neurotransmitter marker GABA

METHODS AND COMPOSITIONS FOR CRYOPRESERVATION OF DISSOCIATED PRIMARY ANIMAL CELLS

This application is a U.S. national stage filing under 35 U.S.C. §371 of PCT Application No. PCT/CA02/00393, filed on Mar. 25, 2002, and claims benefit of application U.S. Ser. No. 60/278,492, filed Mar. 23, 2001.

The present invention relates to cell culture compositions, cryopreservation compositions and methods of cryopreserving cells.

BACKGROUND OF THE INVENTION

Cell cultures are used routinely for a variety of research, drug screening and diagnostic testing procedures. Animal and human cell cultures, especially three dimensional cell cultures are used for testing active agents, drugs and cosmetics, as well as for substitution of animal tests and for transplantations.

Neuronal cultures are widely employed in research, particularly in the study of receptor function, receptor localization, neuronal inflammation, neuronal degeneration and cell death. Further, the use of primary neuronal cultures has increased in part due to the increased prevalence of neuronal disorders and diseases such as Huntingtons, Parkinsons and Alzheimers disease in the population. The use of such primary neuronal cultures permit normal and neuropathological target cell populations to be studied in isolation.

Primary cell cultures more faithfully reproduce the characteristics of native tissue than do immortalized cell lines. A serious limitation of using cell lines is that the phenotype and genotype of cells may change with time in culture, especially over several generations. These changes may manifest as a loss of tissue-specific function or biotransformation capacity. Further, alterations in karyotype, morphology, and biochemical properties may occur. Recently, immortalized cell lines derived from primary cultures have been isolated in which the cells exhibit apparently stable phenotypes and genotypes and retain much of the differentiated function of the parent cell. However, it is difficult if not impossible to ascertain whether such immortalized cells may accurately model native tissue in all physiological aspects.

Dissociated primary cell culture is the most widely used in vitro system in neurobiology and much work has focused on obtaining cultures representative of neuronal populations in the brain, spinal cord, and dorsal root ganglion. The majority of studies on central and peripheral nervous tissue in primary culture have been performed using embryonic or neonatal tissues, as cells at early developmental stages possess greater potential for growth in culture (Crain, 1976). Both explant cultures and dissociated cell cultures from neonatal animals have been isolated to study specific cell types. For example, explants (Jessen et al., 1983) and cell cultures (Nishi and Willard, 1985) from the neonatal rat myenteric plexus have been developed to study the enteric nervous system (ENS). While primary cell cultures more faithfully reproduce the characteristics of native tissue than do immortalized cell lines, primary neuronal cell cultures derived from neonatal animals do not, in all cases, represent accurate models of adult neuronal systems. Specifically, ENS maturity is reached only at one month after birth and certain neuronal populations can only first be detected two to three weeks after birth (Matini et al., 1997). Further, nerve cell numbers per ganglia decrease by approximately half in the first two weeks of life (Schafer et al., 1999). Therefore, there is a need within the art of a supply of primary cells (v. primary cell cultures) from all developmental stages of an animal.

There are also other drawbacks associated with the use of primary cell cultures Primary cell cultures are inconvenient to work with in that they often require ordering and delivery of animals and/or timed pregnant animals and then difficult and expertise intensive dissection and dissociation procedures. Further, there are many scheduling difficulties that incur delays when carrying out primary cell culture work. This is particularly true in the case of primary neuronal cultures as they require fetal or neonatal substrate tissue. Also, the financial costs and resources required to maintain viable neuronal cultures at a research site can be high and often prohibitive. At present, there is currently no commercial source for mammalian neurons either as primary culture material or precursor culture material. This is due to the poor viability of neurons in culture and the inability to cryopreserve and transport neurons Cryopreservation is employed widely for the prolonged storage of mammalian cell lines, tissue and primary non-neuronal cells such as hepatocytes (Swales et al 1996). However, cryopreservation of primary neurons has been limited to blocks of dissected CNS tissue which require thawing and dissociation of cells for culture (Hashimoto et al., 2000) A drawback of cryopreserving blocks of tissue is that the tissue must be thawed and cells of interest dissociated and isolated from the tissue and subsequently cultured. Processing of the cells requires significant expertise and the chances of injury or contamination of the neuronal cultures are high. U.S. Pat. No. 5,328,821 discloses cryopreservation solutions for tissue slices obtained from liver. Thus, there is a need for cryopreserved dissociated primary neuronal cells which may be easily thawed and cultured.

U.S. Pat. No. 6,140,123 discloses a method for preconditioning and cryopreservation of porcine hepatocytes cells harvested from a donor wherein the cells are suspended in a cryopreservation medium comprising DMSO, glutathione, adenosine, a calcium channel blocker and a cell nutrient matrix. The reference does not teach whether the compositions may be used for cryopreservation of primary dissociated neuronal cells. U.S. Pat. No. 6,140,116 discloses cell culture of porcine neural cells and methods for using the cells to treat neurological deficits due to neurodegeneration. The reference teaches that N-acetylcysteine and ascorbic acid may be used to counteract the adverse effects of oxidative stress during preparation for transplantation. However, there is no disclosure of the cryopreservation of neuronal cells. U.S. Pat. No. 5,972,923 discloses methods and compositions for enhancing the cytoprotective effects of polycyclic phenolic compounds through the synergistic interaction with anti-oxidants. The compositions disclosed may comprise a plurality of antioxidants including ascorbic acid, and glutathione. There is no disclosure as to whether any of the compositions may be employed to cryopreserve primary neuronal cells.

U.S. Pat. No. 5,849,585 discloses a method for enhancing the survival and proliferation of Schwann cells in cell culture using serum free culture medium comprising mitotic agents. In addition, other optional supplements may be added to the cell medium including vitamin E as an antioxidant and anti-transforming agent. U.S. Pat. No. 5,849,584 discloses a method for producing an expanded, primary, non-transformed cell culture wherein the cultured cells may be selected from glandular neuroblast, liver, adrenal cortex, oral mucosa, cartilage inner ear or bladder cells. The cells may be cultured in a medium comprising ascorbic acid between 30 and 125 mg/L. U.S. Pat. No. 4,927,762 discloses culturing cells in serum free media in combination with a non-toxic antioxidant (N-acetylcysteine, mercaptoproprionic acid, 2-mercaptoethanesulfonic acid, or thiolactate). WO 99/35242 teaches media compositions and culturing compositions for the growth and function of secretory cells. However, none of these documents disclose whether the compositions may be employed to cryopreserve primary dissociated neuronal cells.

The article entitled "Heme oxyenase immunoreactive neurons in the rat intestine and their relationship to nitrergic neurons" by Donat et al., Journal of the Autonomic Nervous System (1999) discloses isolation and culturing primary rat enteric neurons. However, the article does not teach cryopreservation of ENS or other cells from primary dissociated neuronal tissue.

There is a need in the art for cell culture and cell cryopreservation compositions which may be used to culture and cryopreserve primary neuronal cells. Further there is a need in the art for processes for the cryopreservation of primary neuronal cells. Further there is a need for cell cryopreservation compositions and methods of cryopreserving primary neuronal cell in high yield so that these cells may be shipped to distant destinations for use and study.

Further there is a need in the art to identify cryopreservation compositions and methods of culturing primary neuronal cells, such that cryopreserved cells are physiologically indistinguishable from noncryopreserved primary cells in regard to cell morphology, physiology and electrophysiology.

It is an object of the present invention to overcome disadvantages of the prior art.

The above object is met by a combination of the features of the main claims. The sub claims disclose further advantageous embodiments of the invention.

SUMMARY OF THE INVENTION

The present invention relates to cell culture compositions, cryopreservation compositions and methods of cryopreserving cells.

According to the present invention there is provided a ENS cell cryopreservation composition comprising ENS cell culture composition (nutrient medium, serum, D-glucose, L-glutamine, an antibiotic, at least one mitotic inhibitor), and at least one cryopreservative. Preferably, the at least one cryopreservative is dimethylsulfoxide (DMSO. The present invention also provides for a kit comprising an ENS cell culture composition and an ENS cell cryopreservation composition, as just defined, or an ENS cell cryopreservation composition, along with instructions for use of the kit.

The present invention is also directed to the use of the ENS cell cryopreservation composition as defined above for cryopreservation of ENS cells. Preferably, the ENS cells are primary ENS cells selected from the group consisting of enteric nervous system neurons, glial cells, fibroblasts, or a combination thereof.

The present invention also provides for a composition comprising a ENS cell cryopreservation composition, and primary ENS cells. The present invention also provides for a kit comprising an ENS cell cryopreservation composition and an ENS cell culture composition. The present invention also embraces the kit as just defined, that further comprises cryopreserved ENS cells. Preferably, the ENS cells are primary ENS cells.

The present invention pertains to a method of cryopreserving primary ENS cells comprising the steps of
  A) isolating said primary ENS cells;
  B) freezing said ENS cells in an ENS cell cryopreservation composition comprising nutrient medium, serum, glucose, glutamine, an antibiotic, at least one mitotic inhibitor and at least one cryopreservative.

According to the present invention, there is also provided a CNS cell culture composition comprising nutrient medium, serum, D-glucose, L-glutamine, an antibiotic, and at least one antioxidant.

The present invention further pertains to a CNS cell cryopreservation composition comprising a nutrient medium, serum, D-glucose, L-glutamine, an antibiotic, at least one antioxidant, and a cryopreservative. Preferably the cryopreservative is dimethylsulfoxide (DMSO).

The present invention also pertains to the use of the CNS cell culture composition for culturing primary CNS cells. Preferably the primary CNS cells comprise cells selected from the group consisting of central nervous system neurons, glial cells, fibroblasts, or a combination thereof.

The present invention provides for a CNS cell culture composition comprising primary CNS cells.

This invention also pertains to the use of a CNS cell cryopreservation composition for cryopreserving primary CNS cells. Preferably, the primary CNS cells comprise cells selected from the group consisting of central nervous system neurons, glial cells, fibroblasts, or a combination thereof.

The present invention also provides for a CNS cell cryopreservation composition comprising primary CNS cells.

The present invention further provides a kit comprising a CNS cell cryopreservation composition and a CNS cell culture composition. The invention also provides the kit as just defined and (1) cryopreserved CNS cells. Preferably, the CNS cells are primary CNS cells.

The present invention also pertains to a method of cryopreserving primary CNS cells comprising the steps of
  A) isolating said primary CNS cells;
  B) freezing said CNS cells in a CNS cell cryopreservation composition comprising nutrient medium, serum, glucose, glutamine, an antibiotic, at least one antioxidant, and at least one cryopreservative.

The present invention also provides a cryopreserved ENS cell, and a cryopreserved CNS cell.

ENS and CNS cells have not been successfully dissociated from the mammalian intestine, stored frozen and subsequently thawed and maintained in primary culture. Cryopreserving these cells provides the opportunity to maintain on hand a supply of dissociated primary neurons that are 'culture' ready for broad application in general research, drug screening and neurotoxicity testing.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1A shows results obtained by immunohistochemical staining of primary enteric neurons with an anti-neuron enolase specific antibody following cryopreservation, thawing and re-culturing primary cells using the cell culture and cryopreservation compositions of the present invention. FIG. 1B shows immunohistochemical staining of the intermediate filament protein GFAP in glial cells co-isolated, crypreserved, and cultured with enteric neurons. FIG. 1C shows immunostaining of vimentin in fibroblasts co-isolated, crypreserved, and cultured with enteric neurons.

FIG. 1C' shows the culture represented in FIG. 1C, at a different focal plane emphasizing the localization of fibroblasts (arrows).

FIG. 4 shows electrophysiological characteristics of enteric neuronal cells.

FIG. 14 shows results of cryopreserving and culturing mouse cortex cells using the cryopreservation and cell culture compositions of the present invention.

FIG. 16 shows results of staining rat hippocampus cells subjected to cryopreservation and culturing using the compositions of the present invention.

DESCRIPTION OF PREFERRED EMBODIMENT

Figure 1:
FIG. 1 SC shows fresh mouse hippocampal cells (postnatal day 1), or cortex cells (embryonic day 18/19) cultured for 7 days in CNS cell culture composition medium.

The present invention relates to cell culture compositions, cryopreservation compositions and methods of cryopreserving cells.

The following description is of a preferred embodiment by way of example only and without limitation to the combination of features necessary for carrying the invention into effect.

According to the present invention, there are provided cell culture compositions and cell cryopreservation compositions for culturing and cryopreserving cells. Preferably, the cells are primary cells. More preferably, the cells are primary neuronal cells such as, but not limited to primary neurons derived from the enteric nervous system and central nervous system of an animal. By the term "primary cell" it is meant a cell derived directly from an organism such as, but not limited to an animal. For example, but not wishing to be limiting, a primary neuronal cell may comprise any type of neuronal cell derived directly from any animal, or more preferably cells obtained from a mammal. As is evident to someone of skill in the art, a primary neuronal cell is incapable of undergoing mitosis in culture. However, the present invention also contemplates cell culture compositions, cell cryopreservation compositions and methods for culturing and cryopreserving cells including primary cells which may be capable of dividing in culture. Examples of such cells include, but are not limited to glial cells and fibroblasts. Cells are preferably derived from animals comprising a known genotype. The present invention further contemplates culturing and cryopreservation of cells from, but not limited to, native, gene knock-out, or transgenic animals.

Primary Enteric Nervous System (ENS) Cells

According to an embodiment of the present invention, there is provided an enteric nervous system (ENS) cell culture composition. The ENS cell culture composition comprises nutrient medium, serum, glucose, glutamine, an antibiotic and at least one mitotic inhibitor. An example a suitable ENS cell culture composition is disclosed in Donat et al. (Donat E. M., Wong K., Staines W. A. Krantis A., (1999), J Autonomous Nervous Sys. 77:4-12; which is incorporated herein by reference).

By the term "nutrient medium" it is meant a medium which comprises salts, buffers, and other components in sufficient concentration to maintain the osmolarlity and pH of a solution and to enhance viability of cultured animal cells, as would be evident to someone of skill in the art. The buffer medium may comprise, without wishing to be limiting, calcium chloride ($CaCl_2$), potassium chloride (KCl), D-glucose, phosphate buffers such as but not limited to $NaH_2PO_4$, magnesium sulfate ($MgSO_4$), sodium bicarbonate ($NaHCO_3$), glutamine, magnesium chloride ($MgCl_2$), ethylenediamine tetraacetic acid (EDTA), vitamins, amino acids, and minerals. The nutrient medium may also comprise other components beneficial to the viability of cultured cells, as would be known or determined to someone of skill in the art.

Preferably, the nutrient medium comprises Minimal Essential Medium (MEM) and is prepared according to standard protocols as known in the art. Other nutrient media which may be used in the composition of the present invention, as would be known to someone of skill in the art. Further, it is preferred that the nutrient medium be sterilized prior to use. Sterilization maybe performed according to any method known in the art, for example, but not limited to autoclave sterilization at high temperature and pressure, or microfiltration, as would be known to someone of skill in the art. Further, nutrient medium may comprise liquid medium or a solid composition which subsequently hydrated with water to produce a liquid nutrient medium.

The ENS cell culture composition of the present invention also comprises serum, such as, but not limited to rat serum, horse serum, fetal bovine serum, or a combination thereof. Preferably the serum is rat serum and is present in an amount between about 0.5% to about 5.0% (v/v). More preferably the serum is rat serum and is present in an amount of about 2.5% (v/v). As would be evident to someone of skill in the art, the serum is preferably heat inactivated.

L-glutamine is present in the ENS cell culture composition of the present invention in the amount from about 0.5 mM to about 10 mM preferably, at about 2 mM Further, D-glucose is present in the ENS cell culture composition of the present invention in the amount of from about 5 mM to about 50 mM, and preferably, at about 15 mM.

The ENS cell culture composition also comprises at least one mitotic inhibitor. By the term "mitotic inhibitor" it is meant a chemical or compound which inhibits cells from undergoing mitosis. Mitotic inhibitors include, but are not limited to flurodeoxyuridine, cytosine arabinoside, uridine triphosphate or a combination thereof. Fluorodeoxyuridine may be employed in an amount from about 5 μM to about 50 μM, preferably at about 10 μM. Cytosine arabinoside may be present in an amount from about 10 μM to about 5 mM, and preferably at about 1 mM. Uridine triphosphate may be present in an amount from about 10 μM to about 2.5 mM, and preferably at about 0.5 mM. The ENS cell culture composition of the present invention may comprise flurodeoxyuridine, cytosine arabinoside, uridine triphosphate, or a combination thereof.

The ENS cell composition of the present invention also comprises an antibiotic, such as, but not limited to penicillin-streptomycin. Preferably the cell culture composition of the present invention comprises about 1 U/mL of penicillin-streptomycin. However, as would be evident to someone of skill in the art, other antibiotics may be used in the composition of the present invention at concentrations which inhibit the growth of bacteria and other microorganisms in culture, without affecting the viability of ENS or other cells. The amount of antibiotic required to inhibit the growth of microorganisms may be easily determined by someone of skill in the art.

An example of an ENS cell culture composition, which is not to be considered limiting in any manner, comprises about 90% (v/v) MEM, about 2.5% (v/v) rat serum, about 2 mM L-glutamine, about 15 mM glucose, about 10 μM fluorodeoxuridine, about 1 mM cytosine arabinoside, about 0.5 mM uridine triphosphate and about. 100 U penicillin-streptomycin. Preferably, glutamine, glucose, mitotic inhibitors and antibiotic are prepared individually in distilled water and collectively form about 6.5% (v/v) of the ENS cell culture composition of the present invention. The ENS cell culture composition of the present invention may be prepared according to Example 1.

The ENS cell culture composition of the present invention is employed to culture animal cells such as, but not limited to neuronal cells. Preferably, the ENS cell culture medium is employed to culture primary neuronal cells such as, but not limited to enteric neurons and neuronal cells derived from the myenteric plexus of the small intestine. In a preferred embodiment the neuronal cells derived from the myenteric plexus of the small intestine are mouse, rat, pig, chimpanzee; ape, human, porcine, amphibian, fish, canine, bovine, or poultry cells. However, cells other than mouse, rat, chimpanzee, ape, human, porcine, amphibian, fish, canine, bovine, or poultry cells may be cultured using the ENS cell culture composition of the present invention.

Also according to the present invention there is also provided an ENS cell cryopreservation composition comprising ENS cell culture composition and a cryopreservative. Preferably the cryopreservative is DMSO and is present in an amount of about 6% (v/v) to about 9% (v/v), more preferably about 7% (v/v). An example, which is not to be considered limiting, of an ENS cell cryopreservation composition comprises about 93% (v/v) ENS cell culture composition and about 7% (v/v) DMSO.

The ENS cell cryopreservation composition may be employed to cryopreserve animal cells such as, but not limited to neuronal cells. Preferably, the ENS cell cryopreservation composition is used to cryopreserve primary neuronal cells such as, but not limited to enteric neurons and neuronal cells derived from the myenteric plexus of the small intestine. In a preferred embodiment the neuronal cells are derived from the myenteric plexus of the small intestine and are mouse, rat, pig, or human cells. However, other cells may be cryopreserved using the ENS cell cryopreservation composition of the present invention.

The present invention also provides a kit comprising the ENS cell culture composition as described herein, the ENS cryopreservation composition as described herein, or both. The kit may further comprise ENS cells which are cryogenically frozen using the ENS cryopreservation composition of the present invention. Also, the kit may comprise instructions for the culturing ENS cells, cryopreserving cells, thawing cells, reculturing thawed cells or any combination thereof.

The present invention further provides a method of culturing and cryopreserving ENS cells using the ENS cell culture and ENS cell cryopreservation compositions of the present invention. The method of the present invention may comprise, but is not limited to, the following steps:
 a) dissecting tissue comprising ENS cells from an animal;
 b) dissociating ENS cells from dissected tissue;
 c) isolating ENS cells;
 d) culturing ENS cells in the ENS cell culture composition of the present invention;
 e) freezing ENS cells in the ENS cell cryopreservation composition of the present invention;
 f) storing cryopreserved ENS cells;
 g) thawing ENS cells;
 h) culturing thawed ENS cells;
 As would be evident to someone of skill in the art, not all of the steps described above may be required to achieve a desired goal. For example, steps a) through e) or f) may be performed separately, and by different users, from steps g) and h). Similarly, ENS cells maybe dissected, dissociated, isolated and cultured (steps a) through d)) using the ENS cell culture composition of the present invention. In such an embodiment, the cells are not subjected to freezing, thawing or other steps as described above. Thus, the method of the present invention contemplates culturing ENS cells, cryopreserving ENS cells, or both.

Dissection of Tissue Comprising ENS Cells

Dissecting tissue comprising ENS cells from an animal may be performed according to any method known in the art. Further, any tissue may be dissected from any animal provided that the animal and the tissue comprise ENS cells. Animals which may be used in the method of the present invention include, but are not limited to, mammals, including, mice, rats, cats, dogs, humans, chimpanzees, apes, bovine, porcine, hamster, equine, fish, nematode, leech, drosophila or *Aplaysia*. In a preferred embodiment, tissue comprising ENS cells is dissected from Sprague Dawley rats. For example, cells comprising the myenteric plexus maybe isolated from rat ileum. Preferably the dissection is performed under conditions which minimize damage of tissue and ENS cells. It is preferred that tissue isolated from an animal be flushed with an ice-cold solution which is compatible with the tissue being isolated. For example, but not to be considered limiting, rat ileum segments are preferably flushed with freshly prepared Krebs solution (gassed with 95% $CO_2$, 5% $O_2$) throughout dissection to minimize damage to ENS cells (Donat E. M., Wong K., Staines W. A., Krantis A., (1999), J Autonomous Nervous Sys. 77:412; which is incorporated herein by reference).

As will be evident to someone of skill in the art, it is preferred that the dissection of tissue be performed relatively quickly to minimize the time that ENS cells are exposed to unfavorable growth conditions.

Dissociation of ENS Cells from Tissue

Dissociation of ENS cells from tissue maybe performed according to any method known in the art, for example, but not limited to physical dissociation, enzymatic dissociation or combinations thereof. Preferably, dissociation of ENS cells are performed under sterile conditions, for example, but not limited to, in a sterile laminar flow hood. A suitable method for dissociating ENS cells from tissue is provided in Donat et a; (Donat E. M., Wong K., Staines W. A., Krantis A., (1999), J Autonomous Nervous Sys. 77:4-12; which is incorporated herein by reference).

Tissue comprising ENS cells may be dissociated using enzymes such as, but not limited to papain, collagenase, dispase and combinations thereof. If the ENS cells comprise neurons derived from the myenteric plexus of rat ileum, preferably the dissociated tissue is placed in filter-sterilized Hanks Balanced Salt solution about pH 7.3 containing about 1% (v/v) papain and about 0.61% (w/v) L-cysteine, or other suitable medium, and incubated for about 10 minutes in a 37° C. water bath. However, it is to be understood that any mammalian ENS cell may be dissociated as described herein in the presence of suitable media.

Following enzymatic treatment with papain, the tissue is rinsed in a suitable washing medium, such as, but not limited to Leibovitz's L15 medium supplemented with 10% (v/v) fetal bovine serum, 2 mM L-glutamine, 15 mM glucose and 100 U penicillin-streptomycin (see Example 1).

The tissue is subsequently incubated with Hank's Balanced Salt solution containing about 0.1% (w/v) collagenase type I and about 4% (w/v) dispase II at about 37° C. for a period of about 10 minutes. Following the 10 minute incubation period, the tissue may be gently triturated to aid dissociation of the ENS cells from the tissue. Preferably, the medium of dissociated cells is cooled to about 4° C. and then gently centrifuged to separate ENS cells from medium containing enzymes. The ENS cells may be subjected to any number of centrifugations and medium additions to remove enzyme-containing medium. However, it is preferred that a single centrifugation is performed to sediment ENS cells. Using the above method ENS cells, for example but not limited to, rat enteric neurons may be readily dissociated.

As would be known to someone of skill in the art, dissociation of cells may be performed using enzymes and conditions other than those described above. For example, but not wishing to be limiting, the incubation times and temperatures may vary depending on factors such as, but not limited to the type of tissue being digested, the amount of tissue being digested and the activity of the enzymes. Further, other enzymes may be employed to aid dissociation of cells from tissue.

It is also contemplated that ENS cells may be dissociated from tissue without enzymes such as, but not limited to couagenase, dispase and papain. However, it is preferred that the process is performed with enzymes and in a manner which minimizes damage to the ENS cells.

Dissociated ENS cells may be added to the ENS cell culture composition or the ENS cell cryopreservation composition of the present invention (as defined above), for culturing or cryopreservation of ENS cells, respectively. Dissociated ENS cells may be cultured by adding the cells to the ENS cell culture composition of the present invention and subsequently plating the ENS cells on a suitable substrate at a suitable density. For example which is not to be considered limiting, if the ENS cells comprise neuronal cells derived from the myenteric plexus of rat ileum, then cells are plated onto a suitable substrate at about 1000 cells per square mm. A suitable substrate may comprise, but is not limited to a coated coverslip, a coated sterile glass slide or a coated cell culture plate. Preferably the substrate is coated with a material which aids in the attachment of the ENS cells onto the substrate, such as, but not limited to Matrigel. Following plating, the cell cultures are maintained at about 37° C. in an incubation chamber with an atmosphere comprising about 95% $CO_2$, 5% $O_2$.

Freezing and Cryopreservation of ENS Cells

Freezing ENS cells is performed using the ENS cell cryopreservation composition of the present invention. However, there exists several ways that the cells may be frozen, as would be evident to someone of skill in the art.

The following is provided as an example only and is not meant to be limiting in any manner. ENS cells obtained from dissociated tissue are suspended in the ENS cell culture composition as described herein, or a composition in which the cells remain viable. An aliquot of this cell suspension is added to a solution comprising ENS cell culture composition as defined above, and DMSO such that the resulting solution comprises the ENS cell cryopreservation composition of the present invention. Preferably, the ENS cell cryopreservation composition of the present invention is allowed to equilibrate for a period at about 37° C. More preferably, the ENS cell cryopreservation composition is at a temperature of about 37° C. prior to contacting ENS cells. After the cells of interest are combined with the ENS cryopreservation composition of the present invention, the cells are cooled to about −80° C. Preferably, the cooling takes place at a controlled rate, for example but not limited to, a rate of about 1° C. per minute until about −80° C. The cells remain at about −80° C. for a period of time, for example, from about 4 hours to about 12 hours, prior to transfer to liquid nitrogen for prolonged storage. ENS cells may remain frozen in liquid nitrogen for any period of time. Preferably the ENS cells remain frozen in liquid nitrogen for a period less than about 5 years, more preferably less than about 2 years, still more preferably less than about 1 year. In a preferred embodiment, the cells remain frozen in liquid nitrogen for a period of about 1 day to about 8 months. However, it is also contemplated that ENS cells may be thawed, and the remainder refrozen, prior to storage in liquid nitrogen.

Also contemplated by the present invention, is the transport of ENS cells which are frozen at −80° C. or in liquid nitrogen. These frozen cells may be packaged in the presence of dry ice and shipped to destinations for use by an end user. For example, the present invention contemplates the creation of ENS cell or tissue banks wherein ENS cells may be shipped to various researchers for study. In a preferred embodiment, ENS cells derived from animals comprising a known genotype are stored. The present invention further contemplates culturing and cryopreservation of ENS cells from, but not limited to, native animals, gene knock-out animals, or transgenic animals.

Thawing of Cryogenically Frozen ENS Cells

Thawing of cryogenically frozen ENS cells may be performed in a number of ways, as would be evident to someone of skill in the art. Preferably, ENS cells frozen in the ENS cell cryopreservation composition of the present invention are rapidly thawed, for example, which is not be considered as limiting in any manner, frozen cells may be heated at about 37° C. using a water bath for about 3 minutes. As would be evident to someone of skill in the art, the heating time maybe dependent on the volume of the liquid in which the cells are cryogenically frozen. Preferably, the volume of cryogenically frozen ENS cells which is thawed as discussed above is about 250 µL. Following thawing of ENS cells, cells are diluted with any suitable medium, preferably, the ENS cell culture composition as described herein.

Culturing ENS Cells

Preferably, ENS cells are cultured using the ENS cell culture composition of the present invention on an appropriate substrate. Preferably the substrate comprises an appropriate coating. For example, but not wishing to be limiting, ENS cells may be cultured on cover slips, cell culture dishes or glass slides, or microtitre plates and the like, coated with, but not limited to, Matrigel, poly-D-Lysine, poly-L-Lysine, or collagen. However other coatings may be employed in the method of the present invention, such as, but not limited to specific cells types. For example, but not wishing to be limiting, enteric neurons may be grown on or in the presence of glial cells. Thus, the present invention contemplates culturing enteric neurons and other cells on or in the presence of glial cells. Also, as will be evident to someone of skill in the art, it is preferred that ENS cells be cultured in an appropriate incubator, within a specific temperature range and under conditions which maintain the viability of the cells, as would be known to someone of skill in the art. Preferably the ENS cells are cultured at about 37° C. under an atmosphere comprising about 95% $CO_2$, 5% $O_2$. Preferably, the ENS cell culture composition is replaced with fresh ENS cell culture composition after about the first 24 hours of culturing the ENS cells, and again about every 72 hours following the first change of the ENS cell culture composition of the present invention. However, these time intervals may vary.

ENS cells may be observed microscopically using phase contrast microscopy to monitor the progression of cell adhesion and process extension. Preferably, ENS cultures are removed from incubators for less than about 10 minutes at a time.

ENS cells may be used at any time after plating, preferably 3 to 14 days, more preferably 5 to 10 days, still more preferably 7 days after plating. As will be evident to someone of skill in the art, ENS cells may be unattached to substrate in early stages after thawing and plating.

Referring now to FIG. 1A, there is shown immunohistochemical staining of fixed primary enteric neurons with an anti-neuron enolase specific antibody following dissection of tissue, dissociation of ENS cells from tissue and culturing in the ENS cell culture composition as described herein. The results shown in FIG. 1A demonstrate that enteric neurons which have been isolated from an animal and cultured are morphologically similar to other types of neuronal cells. Referring now to FIG. 1B, there is shown immunohistochemical staining of the intermediate filament protein glial fibrillary acidic protein (GFAP) which is known to be present in glial cells. FIG. 1B shows that glial cells maybe isolated in combination with enteric neurons in the method of the present invention. Referring now to FIG. 1C, there is shown staining for the presence of the mesenchymal intermediate filament protein vimentin, which is known to be present in fibroblasts. The results shown in FIG. 1C show that the ENS cultures prepared as described herein, may comprise small numbers of morphologically-identifiable fibroblasts. Fibroblasts are generally present in isolated small clusters, and constitute less than about 10% of the total cell population in culture. Collectively, FIGS. 1A-C suggest that a variety of cells, including, but not limited to neuronal and non-neuronal cells may be obtained in practising the method of the present invention and that a variety of cell types may be cultured using the ENS cell culture composition of the present invention.

Figure 2A:
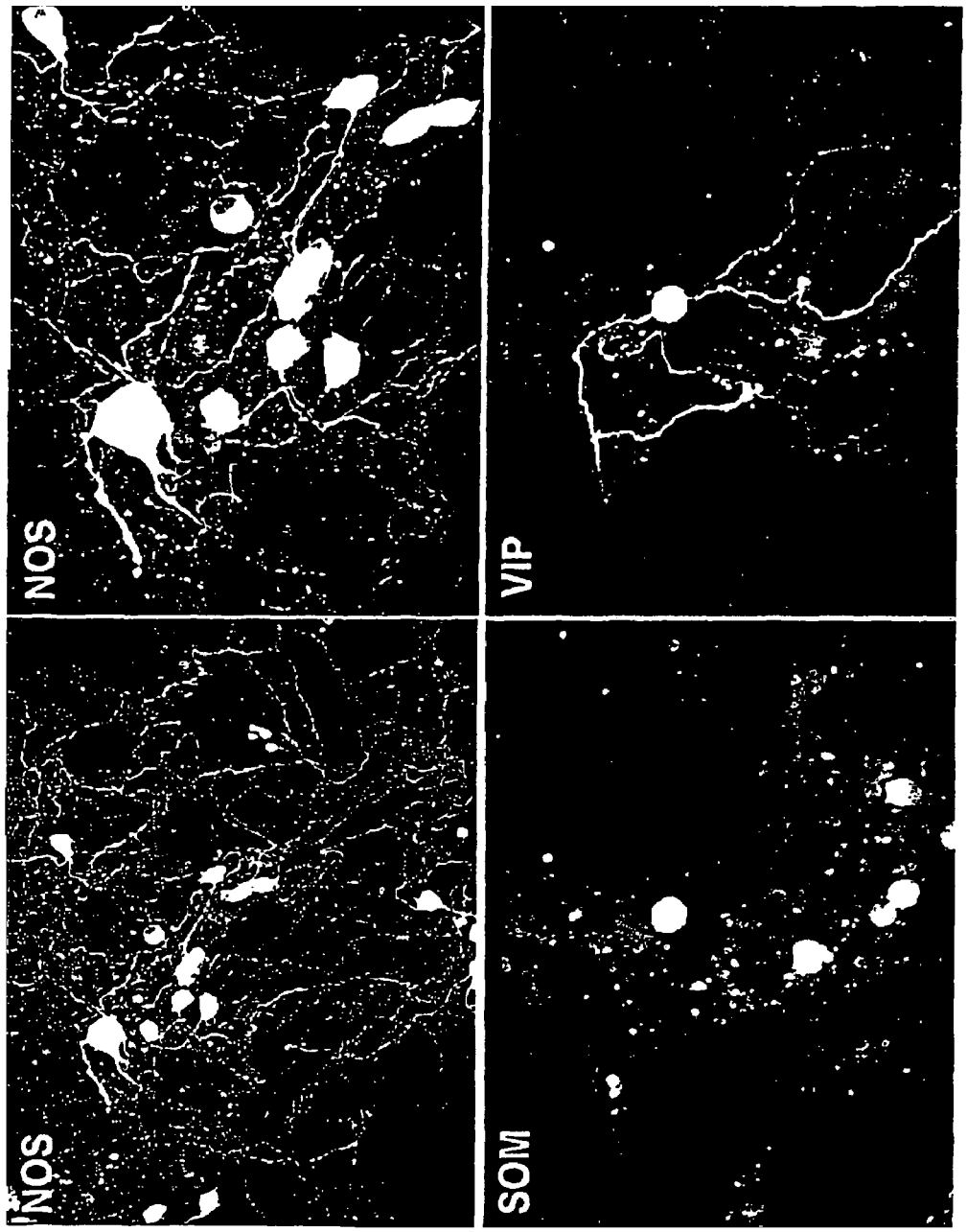
FIG. 2A shows immunohistochemical staining of enteric neuronal subtypes using anti-vasoactive intestinal peptide (VIP), anti-somatostatin (SOM), and anti-nitric oxide (NO) antibodies following cryopreservation, thawing and culturing.
Figure 2B:
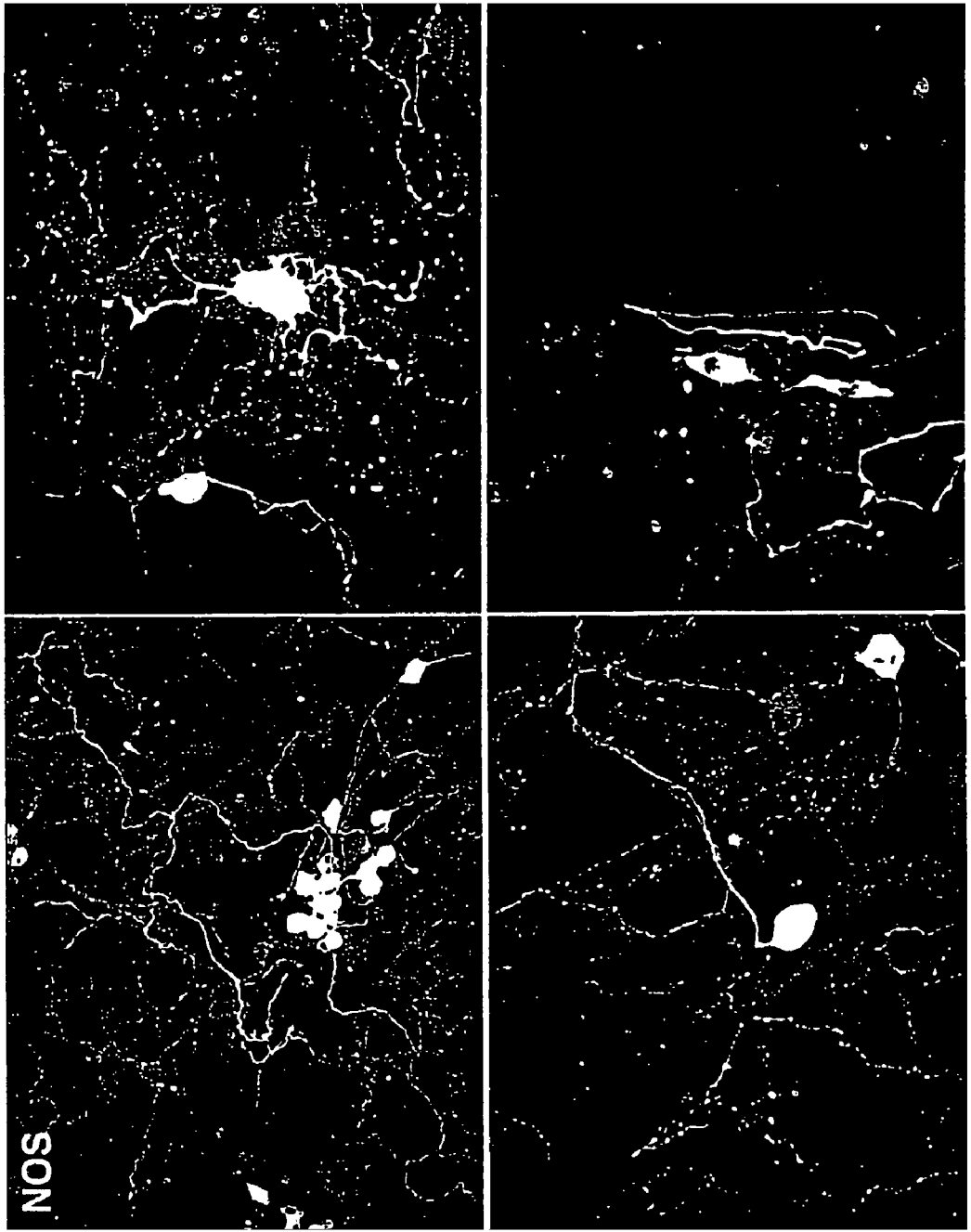
FIG. 2B shows histochemical results suggesting nitric oxide (NO) neuron activity (demonstrated by NADPH-diaphorase staining for NO synthase activity).

Referring now to FIG. 2A, there is shown immunohistochemical staining for typical enteric neuronal cell subtypes following cryopreservation, thawing and culturing (using the ENS compositions and method of the present invention), as indicated by neurotransmitter localization, including anti-vasoactive intestinal peptide (VIP), anti-somatostatin (SOM), and anti-nitric oxide (NO). Referring now to FIG. 2B, there is shown histochemical staining of NO in enteric neuronal cells. The results shown in FIG. 2A and FIG. 2B demonstrate that a variety of neuronal cell types are present in cryopreserved cell cultures. Furthermore, the morphological characteristics, and the number of cells that survive the cryopreservation protocol as described herein are similar to those observed in isolated unfrozen control cell cultures (not shown). The staining patterns observed in FIG. 2A and FIG. 2B suggest the presence of neurons with Dogiel Types I and II morphologies, which are normally present in the mammalian myenteric plexus in vivo.

Figure 3:
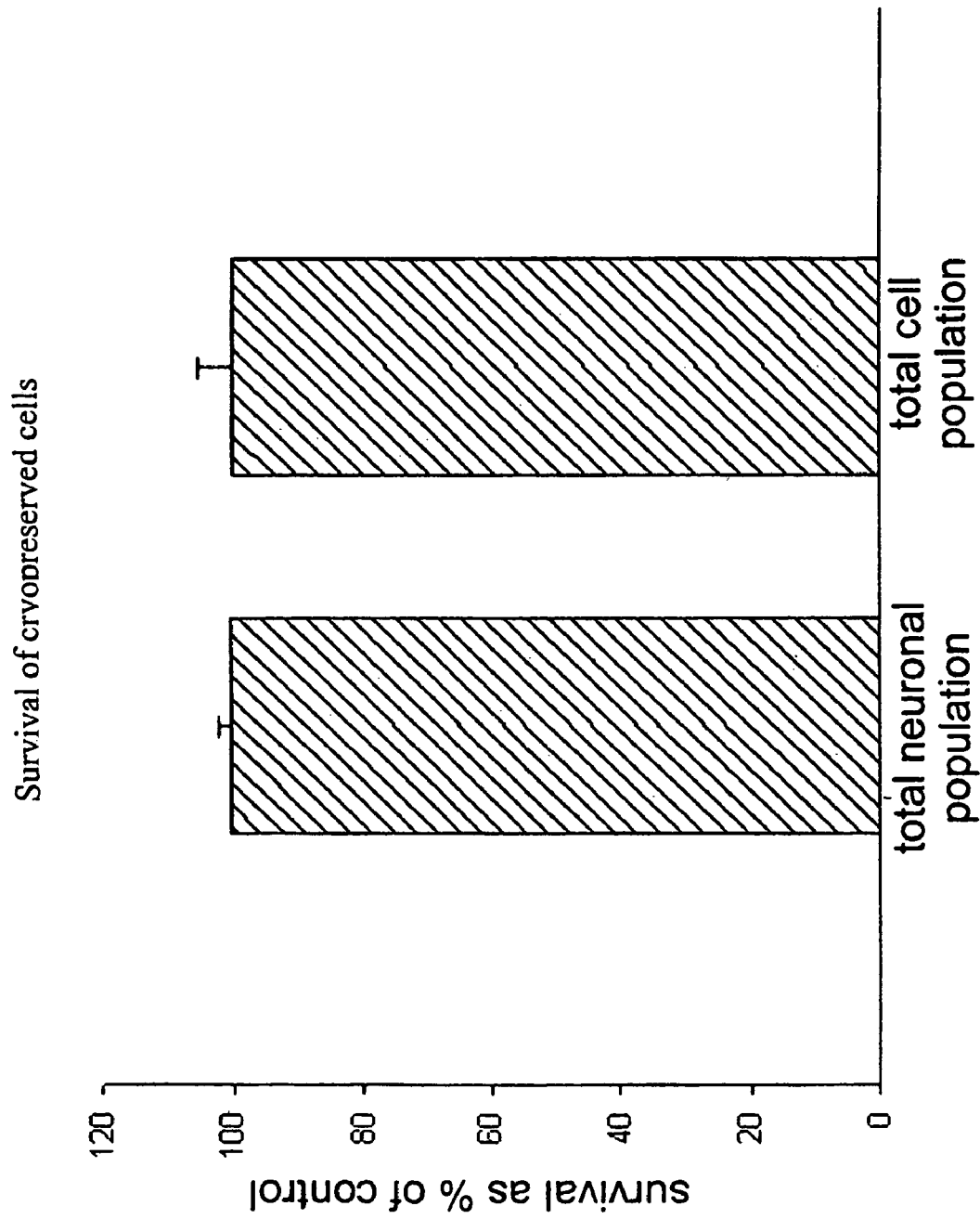
FIG. 3 shows a graphic representation of the percent survival of neuronal and total cells following cell culturing, cryopreservation, thawing and reculturing primary cells, as described herein, relative to cells isolated and cultured without cryopreservation.

Referring now to FIG. 3, there is shown the percent survival of neuronal and total cells following ENS cell culturing, cryopreservation, thawing and reculturing relative to ENS cells isolated and cultured without cryopreservation. These results demonstrate that using the ENS cell culture and cryopreservation compositions of the present invention result from about 90 to about 100% survival of neuronal cells.

Figure 4A:
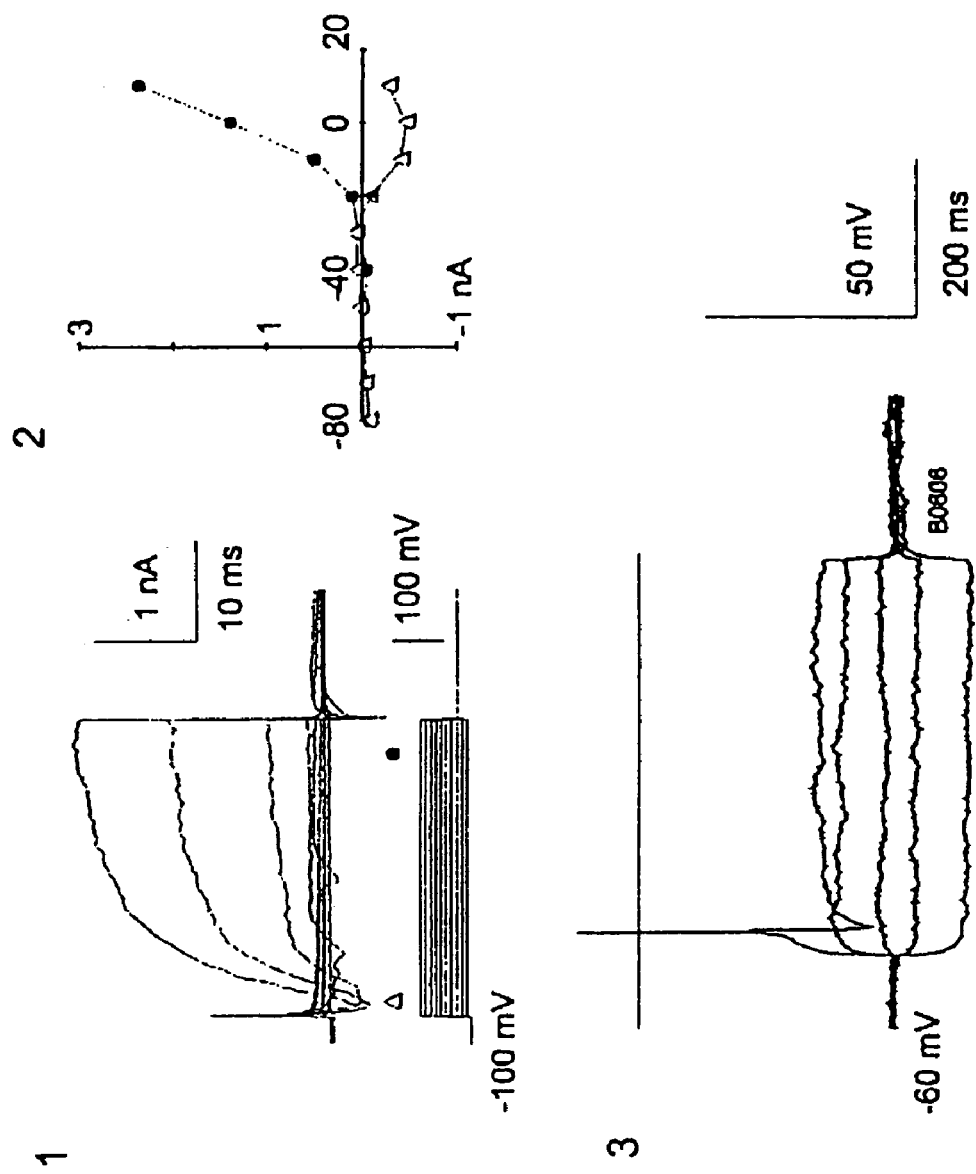
FIG. 4A shows electrophysiological characteristics of ENS cells prior to cryopreservation.
Figure 4B:
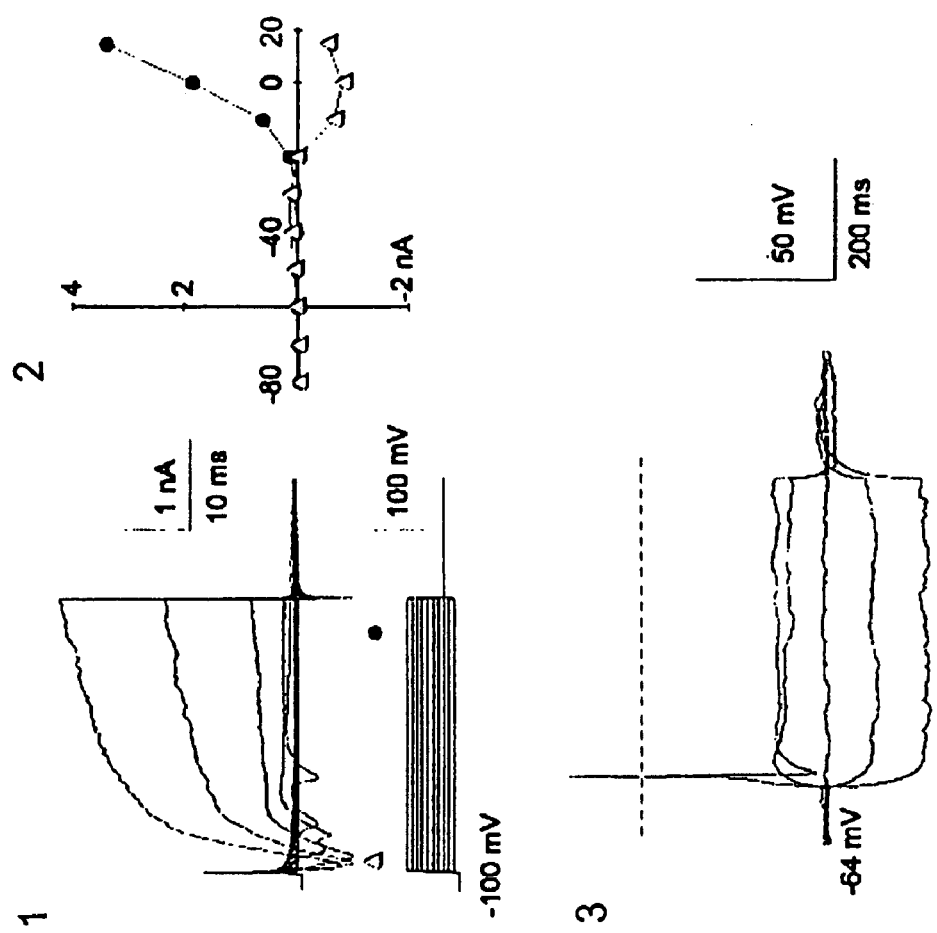
FIG. 4B shows electrophysiological characteristics following cryopreservation, thawing and culturing. Panels 4A-1 and 4B-1 show results of current responses to 10 mV steps from −100 MV in an enteric neuron. Panels 4A-2 and 4B-2 and show the current-voltage relationship obtained by plotting the amplitude of the currents in Panels 4A-1 and 4B-1 against the corresponding membrane potential of the enteric neuron. Open triangles and closed circles represent data from early and late in the response, respectively (exact times are indicated by the symbols below the current traces in Panels 4A-1 and 4B-1). Panels 4A-3, and 4B-3 show results of current clamp behaviour of the same neurons used in Panel 4A-1 and 4B-1 wherein current inputs are 30PA apart.

Referring now to FIG. 4, there is shown electrophysiological characteristics of enteric neuronal cells, cultured with the compositions of the present invention, prior to (FIG. 4A) and after cryopreservation (FIG. 4B). Panels 4A-1 and 4B-1 show results of current responses to 10 mV steps from −100 mV in an enteric neuron. Transient inward currents appear prominent at the beginning of the responses followed by large slowly developing outward currents. The brief inward deflections with latencies longer than about 2 to 3 milliseconds at the beginning of the voltage step suggest the presence of unclamped voltage dependent conductances in the processes of neurons. Panels 4A-2, and 4B-2 show a current-voltage relationship obtained by plotting the amplitudes of the currents shown in Panels 4A-1 and 4B-1, respectively, against the corresponding membrane potentials. Panels 4A-3 and 4B-3 show current clamp behavior of the same neuron wherein current inputs are 30 pA apart. The results shown in FIGS. 4A and B demonstrate that cells subjected to cryopreservation, thawing and re-culturing using the cell culture and cryopreservation compositions of the present invention display similar electrophysiological responses to stimulation as unfrozen control cultures. Specifically, but not wishing to be limiting in any manner, myenteric neurons cryopreserved using the ENS cryopreservation composition of the present invention, exhibit AH- and S-type electrophysiological responses. These electrophysiological responses are similar to the responses observed by myenteric neurons in vivo (not shown).

Collectively, FIGS. 1-4 suggest that the cell culture and cryopreservation compositions of the present invention permit a wide variety of cells to be cultured and cryopreserved without loss of specific cell subtypes, or a reduction in cell viability following thawing. Further, the results shown in FIGS. 1-4 suggest that cryopreserved cells which are thawed and cultured are morphologically and physiologically similar to unfrozen cells.

Primary Central Nervous System (CNS) Cells

According to an embodiment of the present invention, there is provided a central nervous system (CNS) cell culture composition. The CNS cell culture composition comprises nutrient medium, serum, glucose, glutamine, an antibiotic and at least one antioxidant. The CNS cell culture composition may also comprise one or more mitotic inhibitors. Further, the CNS cell culture composition may be used for the preparation of suitable cells, for example but not limited to, primary CNS cells from an animal, for example, but not limited to a mammal, including murine, rat, pig or human. CNS cells may include, but are not limited to cells obtained from cerebral cortex, striatum, hippocampus, cerebellar granular layer, glial cells, spinal cord cells, dorsal root ganglia, sympathetic neurons, and submucosal plexus. Further, other cells which may be cultured using the CNS cell culture composition of the present invention include, but are not limited to retinal cells, cardiac myocytes, skeletal muscle cells, vascular smooth muscle cells, cerebral endothelial cells, pulmonary endothelial cells, and fibroblasts.

Preferably, the nutrient medium employed in the CNS cell culture composition of the present invention is Minimal Essential Medium (MEM) and is prepared as is known to one of skill in the art. Other nutrient media which may be used in the CNS cell culture composition, for the purposes of plating after thawing, as described below, include Neurobasal medium with B27; Neurobasal medium with B27 comprising one or more antioxidants, for example, but not limited to one or more of the antioxidants as described herein, or N2 medium. Further, as would be known to someone of skill in the art, it is preferred that the nutrient medium be sterilized prior to use. Sterilization may be performed according to any method known in the art, for example, but not limited to autoclave sterilization at high temperature and pressure, or microfiltration, as would be known to someone of skill in the art. Further, nutrient medium may comprise liquid medium or a solid composition which is subsequently hydrated with water to produce a liquid nutrient medium.

The CNS cell culture composition of the present invention comprises serum, such as, but not limited to horse serum, fetal bovine serum, or a combination thereof. The CNS cell culture composition comprises from about 10% to about 30% (v/v) serum, preferably about 20% (v/v) serum. More preferably, the CNS cell culture composition of the present invention comprises about 5% to about 15% (v/v) horse serum and from about 5% to about 15% (v/v) fetal bovine serum, preferably about 10% horse serum and 10% fetal bovine serum. As would be evident to someone of skill in the art, the serum is preferably heat inactivated.

L-glutamine is present in the CNS cell culture composition of the present invention in the amount of from about 0.5 mM to about 5 mM, preferably about 2 mM. Further, D-glucose is present in the CNS cell culture composition of the present invention in the amount from about 10 mM to about 50 mM, preferably about 20 mM.

The CNS cell culture composition of the present invention also comprises an antibiotic, such as, but not limited to penicillin-streptomycin. Preferably the cell culture composition of the present invention comprises about 1 U/mL of penicillin-streptomycin. However, as would be evident to someone of skill in the art, other antibiotics may be used in the composition of the present invention at concentrations which inhibit the growth of bacteria and other microorganisms in culture, without affecting the viability of CNS or other cells. The amount of antibiotic required to inhibit the growth of microorganisms may be easily determined by someone of skill in the art.

The CNS cell culture composition of the present invention may further comprise at least one antioxidant, such as, but not limited to ascorbic acid, N-acetylcysteine, and glutathione. Ascorbic acid maybe present in an amount of from about 100 mM to about 800 mM, preferably about 400 mM. Glutathione may be present in an amount from about 0.5 mM to about 10 mM, prefereably about 2 mM. N-acetylcysteine may be present in an amount from about 100 mM to about 600 mM, preferably about 300 mM. It is contemplated that the CNS cell culture composition may comprise ascorbic acid, glutathione and N-acetylcysteine.

The CNS cell culture composition may also comprise mitotic inhibitors, such as but are not limited to flurodeoxyuridine, cytosine arabinoside, uridine triphosphate or a combination thereof. Preferably, the mitotic inhibitors are fluorodeoxyuridine, from about 5 to about 25 mg/ml, and uridine triphosphate, from about 15 to about 50 mg/ml, More preferably fluorodeoxyuridine and uridine triphosphate are employed in the amount of about 15 mg/ml and 35 mg/ml, respectively.

An example, which is not to be considered limiting in any manner, the CNS cell culture composition of the present invention comprises MEM, about 10% (v/v) fetal bovine serum (BS), about 10% (v/v) horse serum (HS), about 20 mM D-glucose, about 2 mM L-glutamine, about 400 mM ascorbic acid, about 2 mM glutathione, about 300 mM N-acetylcysteine and about 1 U/ml penicillin-streptomycin. The CNS cell culture composition may be employed to culture CNS cells derived from an animal, for example, a mammal, including mouse, rat, pig or human CNS cells derived from cortical tissue, or all brain regions, for example, but not limited to embryonic cortices, spinal cord, retina, striatum, hippocampus, cerebellum, nigra and the like.

The present invention, also provides a central nervous system (CNS)-cell cryopreservation composition. The CNS cell cryopreservation composition comprises nutrient medium, serum, glucose, glutamine, an antibiotic, at least one antioxidant and a cryopreservative. The components and concentrations of the CNS cell cryopreservation composition may be similar to the CNS cell culture composition discussed above, with the addition of a cryopreservative. Preferably the cryopreservative is DMSO and is present in an amount of about 6% (v/v) to about 9% (v/v), preferably about 8% (v/v) The CNS cell cryopreservation composition may also comprise one or more mitotic inhibitors as disclosed above.

The DMSO which is employed in the ENS and CNS cell cryopreservation compositions of the present invention is substantially dry, that is the DMSO itself contains less than about 20% (v/v) water, more preferably less than about 10% (v/v) water and more preferably less than about 1% (v/v) water. The water content of DMSO may be determined by any method known in the art, for example, but not wishing to be limiting, by NMR, as would be evident to someone of skill in the art.

An example, which is not to be considered limiting in any manner, of a CNS cell cryopreservation composition, comprises MEM, about 10% (v/v) fetal bovine serum (FBS), about 10% (v/v) horse serum (HS), about 20 mM D-glucose, about 2 mM L-glutamine, about 400 mM ascorbic acid, about 2 mM glutathione, about 300 mM N-acetylcysteine about 1 U/ml penicillin-streptomycin and about 8% (v/v) DMSO. The CNS cell cryopreservation composition may be employed to cryopreserve CNS cells derived from an animal, for example a mammal, bovine, porcine, chimpanzee, ape, hamster, equine, canine, feline, *Aplysia*, nematode, leech, fish. Preferably the CNS cells are murine, rat, or human CNS cells derived from cortical tissue or tissues from all brain regions, for example, but not limited to embryonic cortices, spinal cord, retina, striatum, hippocampus, cerebellum, nigra and the like.

In an embodiment, the CNS cell cryopreservation composition of the present invention may be prepared according to Example 1. However, there exists other ways that the CNS cell cryopreservation composition of the present invention may be prepared, as would be evident to someone of skill in the art.

The CNS cell cryopreservation composition of the present invention maybe used to cryopreserve CNS cells, such as, but not limited to primary CNS cells derived from embryonic cortices, hippocampus, striata (caudate putamen) and the like. However, cells other than neuronal cells may be cryopreserved using the CNS cell cryopreservation composition of the present invention.

The present invention further contemplates a method of culturing and cryopreserving CNS cells using the CNS cell culture and CNS cell cryopreservation composition of the present invention. The method of the present invention may comprise but is not limited to:
   a) dissecting tissue comprising CNS cells from an animal;
   b) dissociating CNS cells from dissected tissue;
   c) isolating CNS cells;
   d) culturing CNS cells;
   e) freezing CNS cells in a CNS cell cryopreservation composition of the present invention;
   f) storing cryopreserved CNS cells;
   g) thawing CNS cells;
   h) culturing thawed CNS cells;
   As would be evident to someone of skill in the art, not all of the steps described above may be required in the method of the present invention. For example, but not to be considered limiting, CNS cells may be dissected, dissociated, isolated and cultured using the CNS cell culture composition of the present invention. The cells maybe studied after an appropriate time in culture. In such an embodiment, the cells are not subjected to freezing, thawing or other steps as described above. Furthermore, the cells may be frozen and transported to other users as required. Therefore, the method of the present invention also includes variations of the above steps.

Dissection of Tissue Comprising CNS Cells

Dissecting tissue comprising CNS cells from animal may be performed according to any method known in the art. Further, any tissue may be dissected from any animal providing that the animal and the tissue comprise the CNS cells of interest. Animals which may be used in the method of the present invention include, but are not limited to mice, rats, cats, dogs, humans, chimpanzees, apes, bovine, porcine, equine, avian, or fish. In a preferred embodiment, tissue comprising CNS cells is dissected from Sprague Dawley rats, aplysia, leech, nematode, or fish.

CNS cells to be cultured may be derived from a range of tissues, for example, but not limited to, dissected embryonic tissue, more preferably tissue derived from embryonic cortices, and striata (caudate putamen), substantia nigra, hippocampus, for example from rat, mouse or other subject. Preferably the cortices and striata are maintained in cold phosphate buffered saline (PBS) during dissection, dissociation and handling.

As will be evident to someone of skill in the art, it is preferred that the dissection of tissue comprising CNS cells be performed relatively quickly to minimize the time that the CNS cells are exposed to unfavorable growth conditions.

Dissociation of CNS Cells from Tissue

Dissociation of CNS cells maybe performed according to any method known in the art, for example, but not limited to physical dissociation. In an embodiment, CNS cells are physically dissociated from tissue, for example, but not limited to by trituration. However, it is preferred that the process is performed in a manner which minimizes damage to CNS cells. For example, but not to be considered limiting in any manner, cortices, hippocampus, and striata (caudate putamen) collected from embryonic Sprague-Dawley rats may be gently triturated to dissociate CNS cells. Preferably, few bubbles are created during trituration. Also, as is evident to someone of skill in the art, dissociation of CNS cells is performed under sterile conditions, for example, but not limited to, in a sterile laminar flow hood.

Dissociated CNS cells may be added to the CNS cell culture composition or a CNS cell cryopreservation composition of the present invention as defined above, for cell culturing or cryopreserving CNS cells, respectively.

Dissociated CNS cells may be cultured by adding cells to the CNS cell culture composition of the present invention and subsequently plating the CNS cells on a suitable substrate. A suitable substrate may comprise but is not limited to a coated coverslip, a coated sterile glass slide or a coated cell culture plate. Preferably the substrate is coated with a material which aids in the attachment of the cells onto the substrate, such as, but not limited to Matrigel. Following plating, the cell cultures are maintained at about 37° C. in an incubation chamber with an atmosphere comprising about 95% $CO_2$, 5% $O_2$ in air.

CNS cells may be obtained from dissociated CNS neurons derived from embryonic cortices, caudate putamen, substantia nigra, hippocampus, or a combination thereof, from for example, but not limited to rat, mouse or other source. Prior to culturing, the CNS cells are preferably diluted to about 500,000 cells per ml using the CNS cell culture composition of the present invention and plated onto an appropriate substrate. About 12 to about 16 hours after plating the CNS cells on a suitable substrate, the CNS cell culture composition is removed and replaced with a fresh aliquot of the CNS cell culture composition of the present invention. For CNS cells which have been cultured for a period longer than about 4 days, the CNS cell culture composition may comprise at least one mitotic inhibitor. Mitotic inhibitors may include, but are not limited to fluorodeoxyuridine, uridine triphosphate or a combination thereof. The CNS cell culture composition may comprise about 15 mg/ml fluorodeoxyuridine and about 35 mg/ml of uridine triphosphate. Without wishing to be bound by theory, the mitotic inhibitors may reduce the division of cells, such as but not limited to glial cells which are capable of dividing in culture and which may be isolated in combination with CNS cells.

Freezing and Cryopreservation of CNS Cells

Freezing CNS cells may be performed using the CNS cell cryopreservation composition of the present invention. However, there exists several ways that CNS cells may be frozen. The following embodiment is an example, which is not meant to be limiting in any manner. CNS cells obtained from dissociated tissue are suspended in CNS cell culture composition of the present invention, or a composition in which the cells remain viable. An aliquot of these cells is added to a solution to yield CNS cells suspended in the CNS cell cryopreservation composition of the present invention. Preferably, the CNS cell cryopreservation composition of the present invention which comprises DMSO is allowed to equilibrate for a period at about 37° C., or a temperature which is compatible with the CNS cells of interest. Preferably, the CNS cell cryopreservation composition is at about 37° C. prior to coming into contact with CNS cells. In a preferred embodiment, CNS cells are maintained at a suitable concentration, for example but not limited to, a concentration of about $5 \times 10^6$ cells per ml for freezing. After CNS cells are added to the CNS cryopreservation composition of the present invention, the cells are slowly cooled, for example which is not to be considered limiting in any manner, at a rate of about 1° C. per minute until about −80° C. The cells may remain at about −80° C. for a period of about 4 hrs. Subsequently, the cells are transferred to liquid nitrogen for prolonged storage. Cells may remain frozen in liquid nitrogen for any period of time. Preferably the cells remain frozen in liquid nitrogen for a period less than about 5 years, more preferably less than about 2 years, still more preferably less than about 1 year. In a preferred embodiment, CNS cells remain frozen in liquid nitrogen for a period of about 1 day to about 8 months.

Also contemplated by the present invention, CNS cultures frozen in liquid nitrogen may be packaged with dry ice and shipped to other end users. For example, the present invention contemplates the creation of a CNS cell or tissue bank wherein particular CNS cells may be shipped to various researchers or commercial applications. In a preferred embodiment, the CNS cells are derived from animals with a known genotype. Also, the CNS cells maybe derived from a native animal, a transgenic animal or a gene knock-out animal. In such a manner, the present invention may permit identical types of tissues to be studied by a plurality of end users.

Thawing of Cryogenically Frozen CNS Cells

Thawing of CNS cells may be performed in any number of ways, as would be evident to someone of skill in the art, for example, but not limited to as described in Example 4. Preferably, vials of CNS cells frozen in CNS cell cryopreservation composition are removed from liquid nitrogen and rapidly warmed, for example, heated at about 37° C. using a water bath for about 3 minutes. As would be evident to someone of skill in the art, the heating time maybe dependent on the volume of the liquid in which the cells are cryogenically frozen. Following thawing of the CNS cells, preferably the cells are diluted with the CNS cell culture composition, as described above, which may or may not comprise one or more antioxidant An aliquot of the CNS cell culture suspension is added to a suitable substrate, for example, but not limited to a coverslip coated with MATRIGEL. Preferably, CNS cells are allowed to remain in contact with the substrate for a period of about 6 hours, prior to adding about a ten fold excess of the CNS cell culture composition of the present invention. Further, it is preferable that the incubations are performed at a temperature and under incubation conditions, such as but not limited to 95% $CO_2$, 5% $O_2$ and moisture which are compatible with the viability of CNS cells.

Frozen CNS neurons derived from embryonic tissue, for example from rat embryonic tissue, may be rapidly thawed in a water bath at about 37° C. for about 3 minutes. The thawed cell suspension is then diluted with the CNS cell culture composition of the present invention which is warmed to about 37° C. prior to use. Preferably, the addition of the CNS cell culture composition to the thawed cell suspension is performed drop by drop over a period of about 2 minutes. Without wishing to be bound by theory, sudden dilution of the CNS cell cryopreservation composition of the present invention may result in osmotic damage to cells. Following dilution with the CNS cell culture composition of the present invention, the cells are plated onto an appropriate substrate and placed in an incubator at a temperature of about 37° C. comprising a 5% $CO_2$ in air atmosphere. The CNS cells are incubated under these conditions for a period of about 4 hours, after which the CNS cell culture composition of the present invention is removed and a fresh aliquot of the CNS cell culture composition of the present invention is added to cells. On the fourth day in culture, the CNS cell culture composition of the present invention may be supplemented with at least one mitotic inhibitor as discussed above.

Without wishing to be bound by theory, the stress of centrifuging cryopreserved CNS neurons upon thawing may affect viability of the neurons. Therefore, it is preferred that the method of the present invention not employ centrifugation directly after thawing for CNS cells. Preferably, CNS cells such as, but not limited to those derived from embryonic cortices are thawed and cultured without centrifugation.

Culturing CNS Cells

CNS cells maybe cultured using the CNS cell culture composition of the present invention on an appropriate substrate. For example, but not wishing to be limiting, CNS cells may be cultured on cover slips, cell culture dishes, glass slides or microtitre plates and the like. Preferably, the substrate comprise a coating, such as, but not limited to Matrigel, poly-D-lysine, poly-L-lysine or collagen. However, other coatings may be employed in the method of the present invention, such as, but not limited to specific cells types. For example, but not wishing to be limiting CNS cells may be grown on or in the presence of glial cells. Also, as will be evident to someone of skill in the art, it is preferred that the CNS cells be cultured in an appropriate incubator, within a specific temperature range and under conditions which enhance the viability of the cells, as would be known to someone of skill in the art. Preferably the cells are cultured at about 37° C. under an atmosphere comprising about 95% $CO_2$, 5% $O_2$. Preferably, the cell culture composition is replaced with fresh cell culture composition after about the first 24 hours of culturing the cells of interest, and again about every 48 hours following the first change of the cell culture composition of the present invention.

CNS cells may be observed microscopically using phase contrast microscopy to monitor the progression of cell adhesion and process extension. Preferably, cultures are removed from incubators for less than about 10 minutes at a time.

CNS cells maybe used at any time after plating, preferably 3 to 14 days, more preferably 5 to 10 days, still more preferably 7 days after plating. As will be evident to someone of skill in the art, CNS cells maybe unattached to substrate in early stages after thawing and plating.

It is also contemplated that CNS cells may be cultured in the presence of cryoprotectant, such as, but not limited to DMSO. For example, but without wishing to be limiting, cryogenically frozen CNS cells may which are thawed, diluted with CNS cell culture composition and plated may be cultured in the presence of small amounts of DMSO until the medium is changed. Preferably, the cryoprotectant is present in a CNS cell culture composition in an amount below about 1% (v/v).

Without wishing to be limiting CNS cells may be studied by any method known in the art. For example, but not wishing to be limiting the viability of cells may be determined by cell staining and counting, as would be known to someone of skill in the art. Further, morphological, physiological, biochemical changes of CNS cells cultured and cryopreserved in accordance with the method and compositions of the present invention may be studied for example by immunohistochemistry as would be known to someone of skill in the art. Further, the cells may be studied electrophysiologically, for example, by patch clamps to study voltage channels in the cultured CNS cells. All of the techniques described above which may be employed to characterize cells are well within the capabilities of someone of skill in the art.

Figure 5:
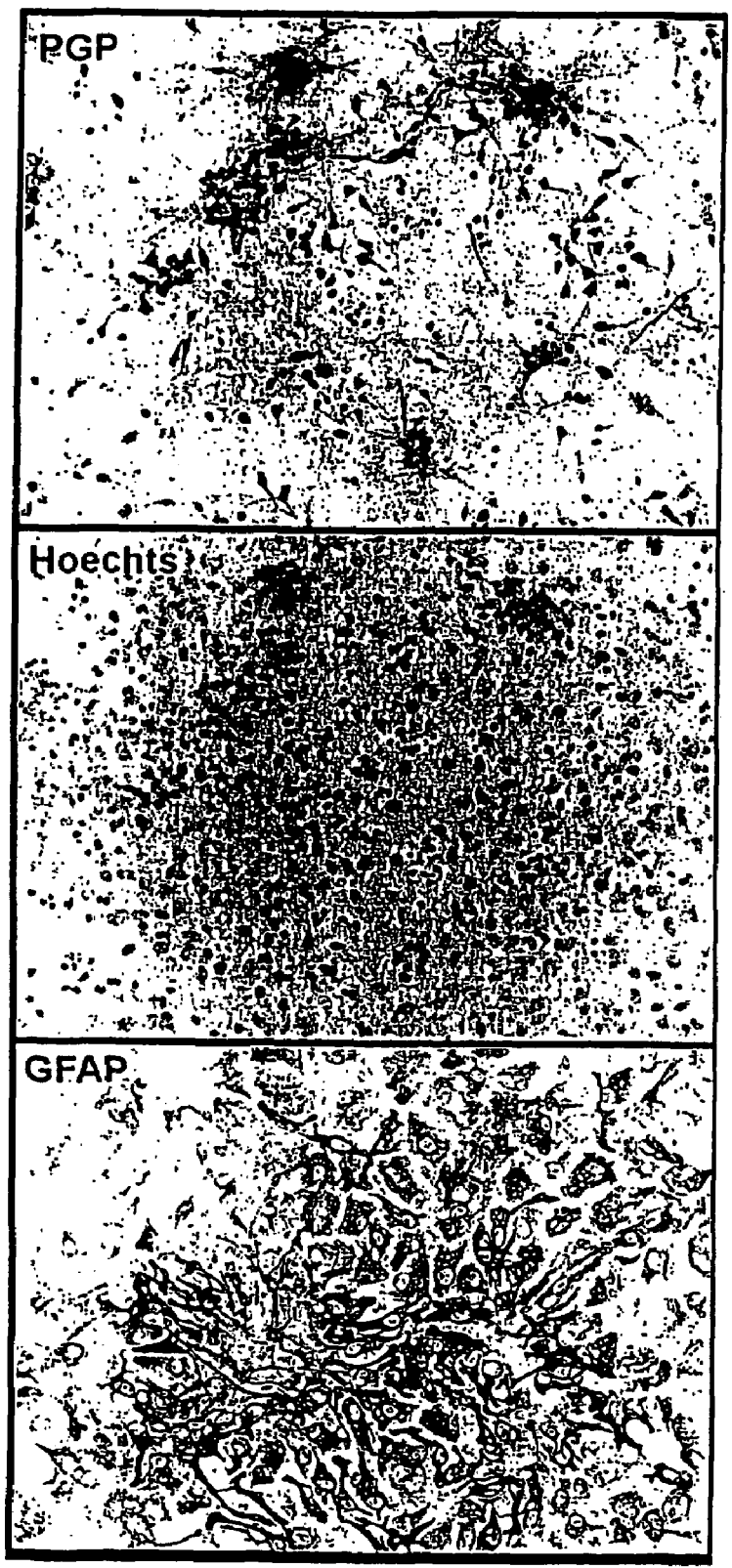
FIG. 5 shows results of immunohistochemical staining of neuronal cells derived from rat cortex following dissection, isolation, cryopreservation, thawing and reculturing using the cryopreservation and cell culture compositions of the present invention using PGP 9.5 antibodies (top panel), Hoechst reagent (middle panel) and GFAP antibodies (lower panel).

Referring now to FIG. 5, there are shown fixed neuronal cells derived from rat cortex following dissection, isolation, cryopreservation, thawing and reculturing using the CNS cell cryopreservation and CNS cell culture compositions of the present invention. The upper panel of FIG. 5 shows staining patterns of fixed neuronal cells using PGP 9.5, a neuron specific antibody directed against ubiquitin terminal carboxylase which may be present in an amount of up to about 2% of the neuronal cytoplasmic protein. The middle panel of FIG. 5 shows Hoechts staining of all cells present in culture. The lower panel shows GFAP staining of glial cells. Collectively, FIG. 5 suggests that a variety of cells and cell types derived from the central nervous system may be isolated, cryopreserved and cultured using the CNS cell culture and CNS cryopreservation compositions of the present invention.

Figure 6:
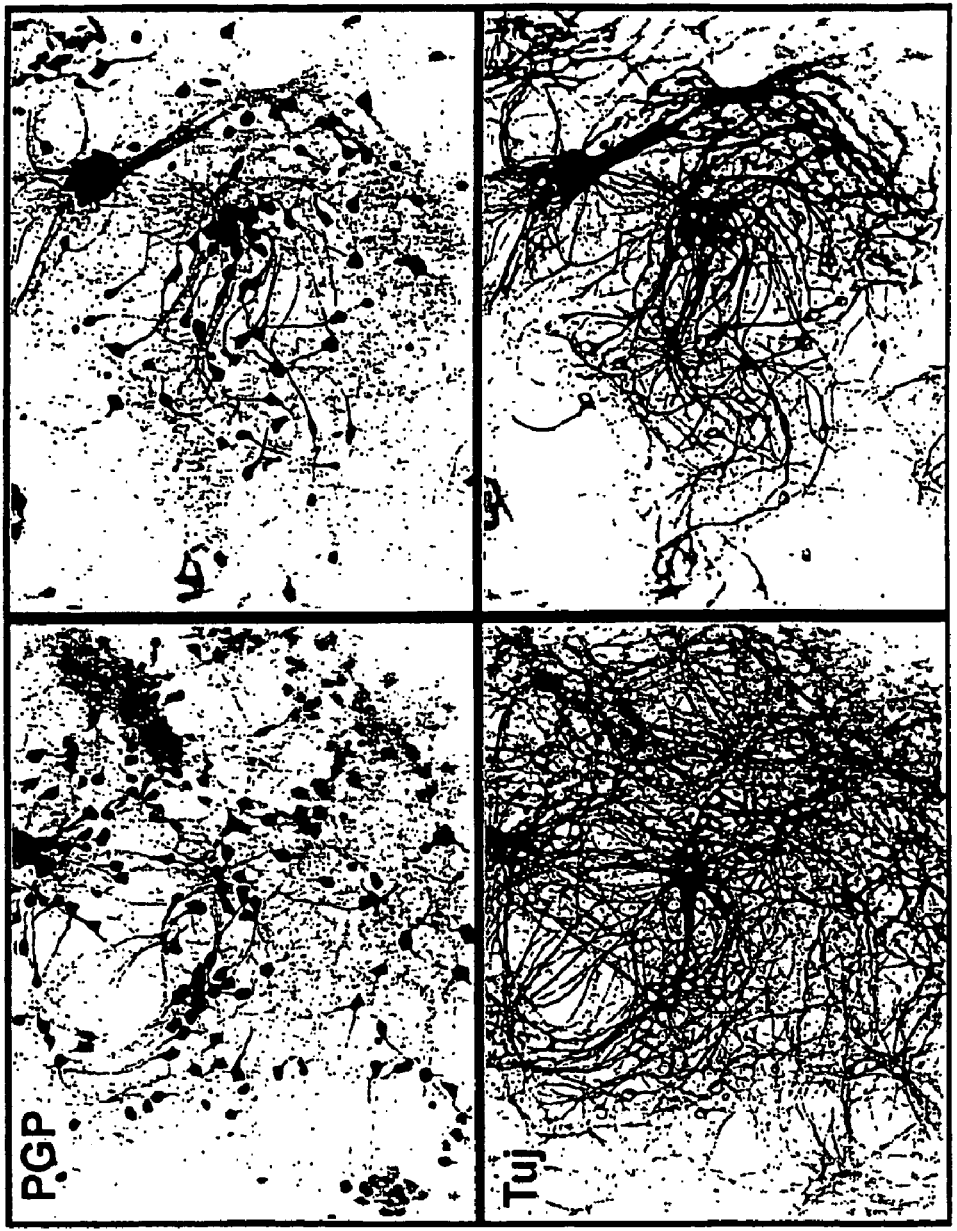
FIG. 6 shows results obatined from PGP and Tuj 1 immunohistochemical staining of fixed CNS cells using various amounts of cryoprotectants.

Referring now to FIG. 6, there is shown PGP and Tuj 1 immunohistochemical staining of fixed CNS cells, which are isolated, cryopreserved using different amounts of cryoprotectant, thawed and cultured. Tuj 1, a neuron specific antibody directed against a juvenile form of tubulin and is a marker for neuronal processes such as axons and dendrites. The results shown in FIG. 6 suggest that the CNS cryopreservation composition of the present invention may comprise different amounts of a cryopreservative in the composition. Specifically, but not wishing to be limiting, DMSO may be employed in the amount of about 6.5% (v/v) to about 9% (v/v), preferably 8% (w/w) in the CNS cryopreservation composition of the present invention. However, other types of cryopreservatives may be used in the CNS cryopreservation composition of the present invention. Further, other amounts of the cryopreservative nay be used in the cryopreservation compositions of the present invention.

Figure 7A:
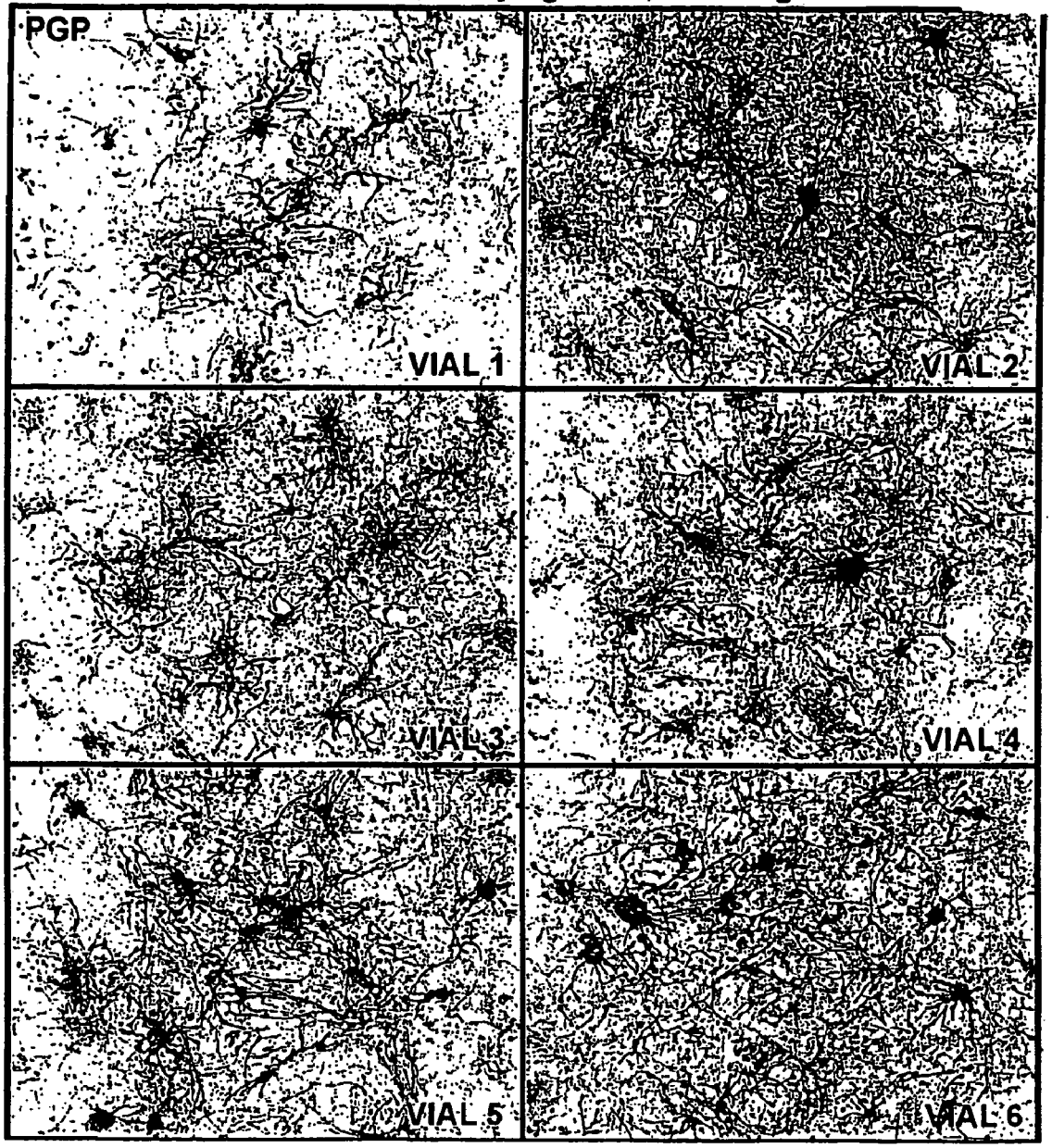
FIG. 7A shows results obtained from anti-PGP immunohistochemical staining of various neuronal cell isolates from various animals and frozen on different dates.
Figure 7B:
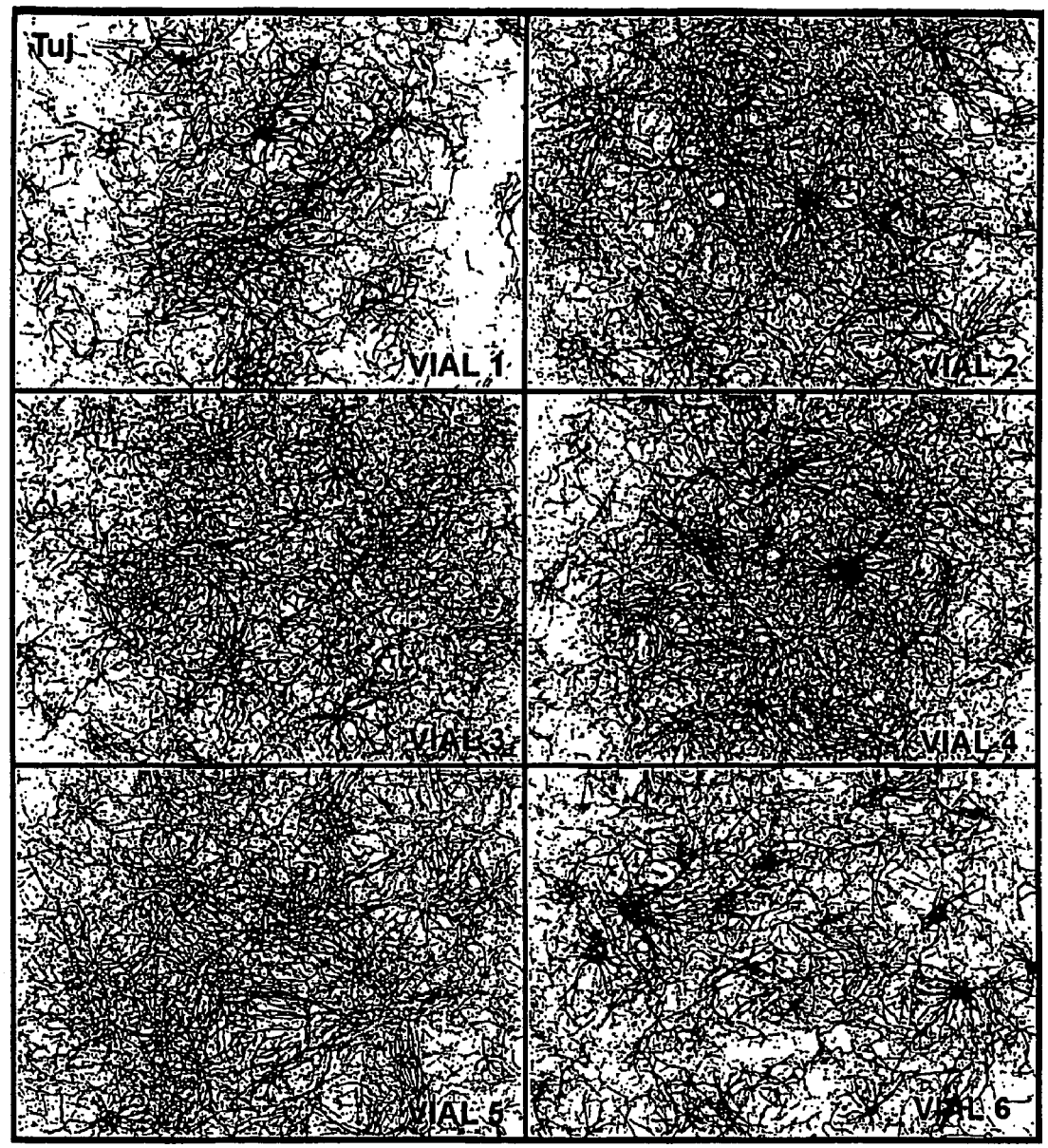
FIG. 7B shows results obtained from anti-Tuj immunohistochemical staining of various neuronal cell isolates from various animals and frozen on different dates.

Referring now to FIG. 7A and FIG. 7B, there is shown PGP and Tuj staining, respectively of multiple aliquots of CNS neurons following cryopreservation, thawing and culturing. The results shown in FIG. 7A and FIG. 7B suggest that the method of cryopreserving cells according to the present invention is reproducible and exhibits low variability.

Figure 8:
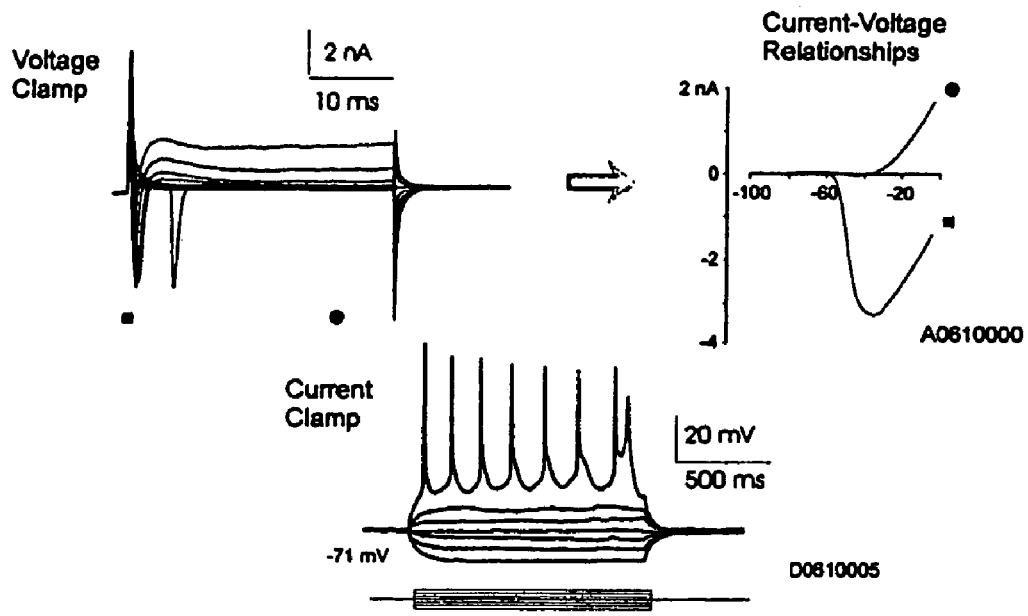
FIG. 8 shows electrophysiological results obtained from CNS neuronal cells cryopreserved and cultured using the compositions of the present invention and identical CNS neuronal cells not subjected to cryopreservation.
Figure 8:
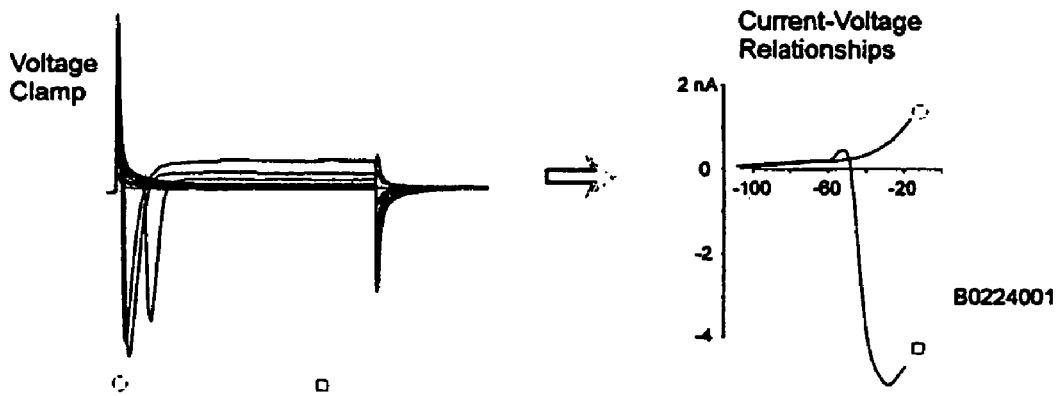

Referring now to FIG. 8, there is shown electrophysiological characteristics of CNS neuronal cells cryopreserved and cultured using the CNS compositions of the present invention and identical CNS neuronal cells not subjected to cryopreservation. The results shown in FIG. 8 suggest that CNS cells cryopreserved and thawed using the cell culture and cryopreservation compositions of the present invention exhibit similar eletrophysiological characteristics to nonfrozen cells.

Further, the results suggest that the CNS cell culture and CNS cell cryopreservation compositions of the present invention and the method of cryopreserving CNS cells yield cells which closely resemble identical uncryopreserved cells.

Figure 9:
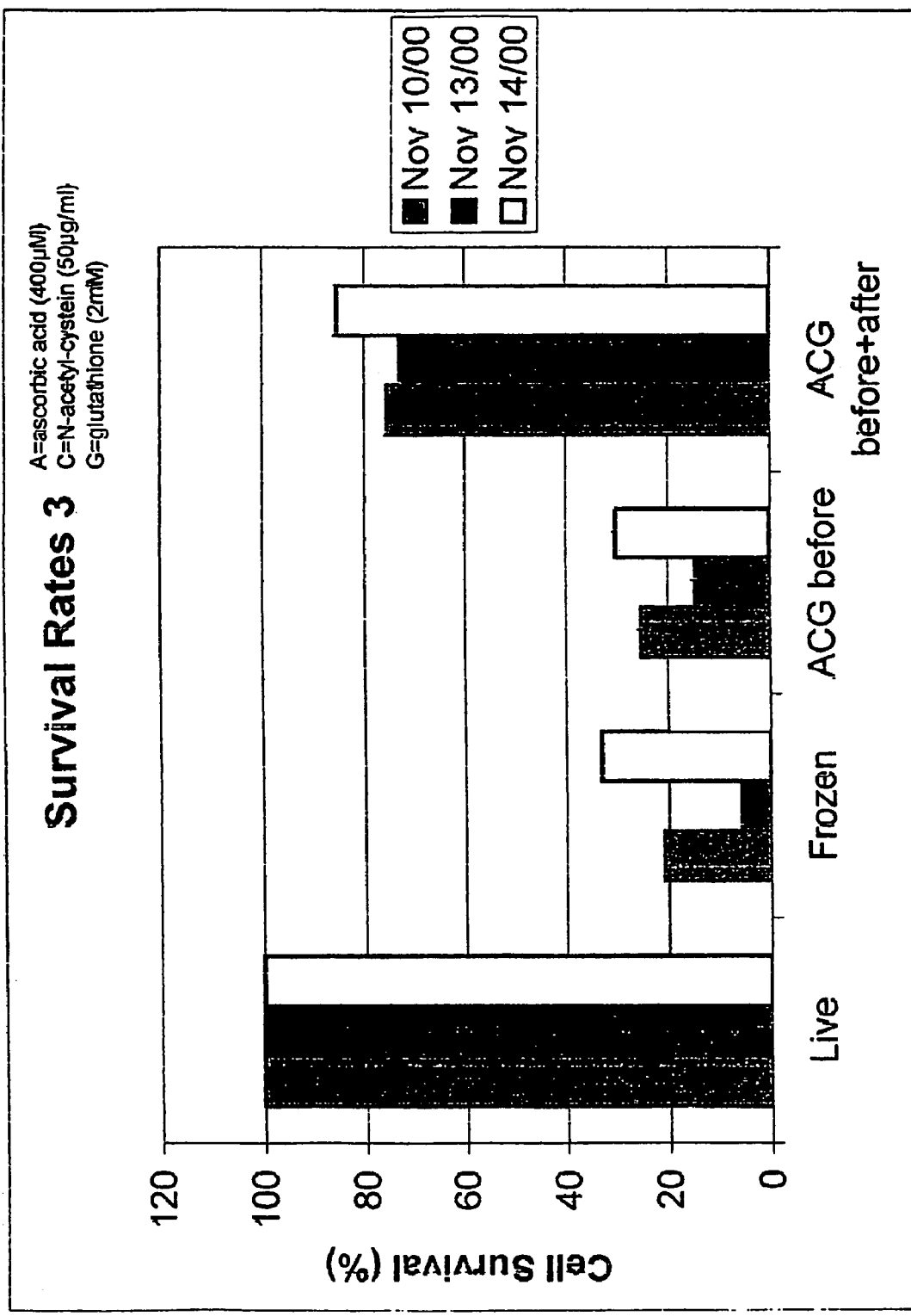
FIG. 9 shows a graphical representation of the percent cell survival for CNS cells subjected to various treatment conditions relative to the viability of isolated and cultured CNS cells. "AGC before", refers to the occurrence of AGC within the medium prior to cryopreservation only. "AGC before and after" refers to the inclusion of AGC within the media prior to and following cryopreservation of primary CNS cells.

Referring now to FIG. 9, there is shown the percent cell survival for CNS cells subjected to various treatment conditions. The percent survival is relative to the viability of isolated and cultured CNS cells (non-cryopreserved). As show in FIG. 9, CNS cells cryopreserved using cell culture compositions which lack antioxidants ("Frozen") exhibit about 25% viability when thawed and cultured. CNS cells which are cryopreserved in the presence of ascorbic acid, N-acetylcysteine and glutathione ("AGC Before") exhibit a slight increase in viability. CNS cells which are cryopreserved in the presence of ascorbic acid, N-acetylcysteine and glutathione, thawed and cultured in CNS cell culture medium comprising ascorbic acid, N-acetylcysteine and glutathione ("AGC Before & After") exhibit about 80% cell survival (all of the cells that were cryopreserved, in the presence or absence of cytoprotectants, were cryopreserved in the presence of DMSO). Thus, the presence of ascorbic acid, glutathione and N-acetylcysteine antioxidants prior to cryopreservation, increases viability of CNS cells. Furthermore, the presence of ascorbic acid, N-acetylcysteine and glutathione during cryopreservation and again within the CNS cell culture composition added to thawed CNS cells, further increases the viability of CNS cells.

Figure 10:
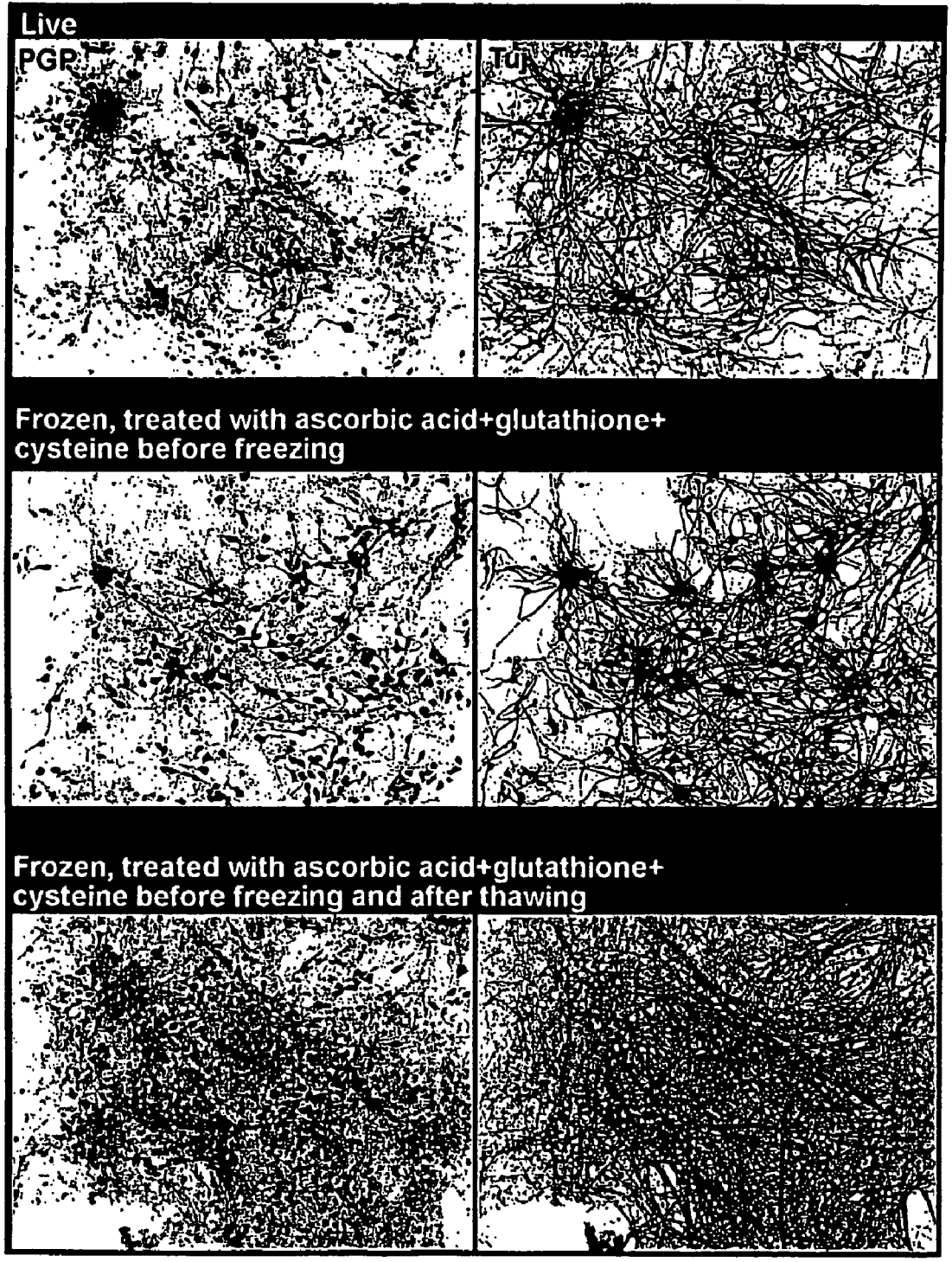
FIG. 10 shows micrographs of CNS cells cryopreserved and plated using cell culture and cryopreservation compositions which lack antioxidants (top panel) versus cell culture and cryopreservation compositions comprising ascorbic acid, glutathione and N-acetylcysteine in the cryopreservation medium (middle panel) and ascorbic acid, glutathione, N-acetylcysteine in both the cryopreservation composition and in the cell culture composition used to culture the CNS cells after thawing (lower panel).

Referring now to FIG. 10, there is shown micrographs of CNS cells cryopreserved and plated using cell culture and cryopreservation compositions which lack antioxidants (top panel) versus CNS cell culture and CNS cell cryopreservation compositions comprising ascorbic acid, glutathione and N-acetylcysteine, but lacking in the cell culture medium after thawed CNS cells are plated and cultured (middle panel) and ascorbic acid, glutathione, N-acetylcysteine in both the CNS cryopreservation compositions and in the CNS cell culture composition used to culture the CNS cells after thawing (lower panel). The results shown in FIG. 10 suggest that the presence of antioxidants, specifically ascorbic acid, N-acetyl cysteine and glutathione in CNS cell cryopreservation and CNS cell culture compositions enhances the viability of the CNS cells. Further, CNS cells cultured and cryopreserved in combination with the antioxidnats disclosed above appear more healthy and more closely resemble normal cells than do cells which are cryogenically frozen, thawed and cultured without antioxidants.

Figure 11A:
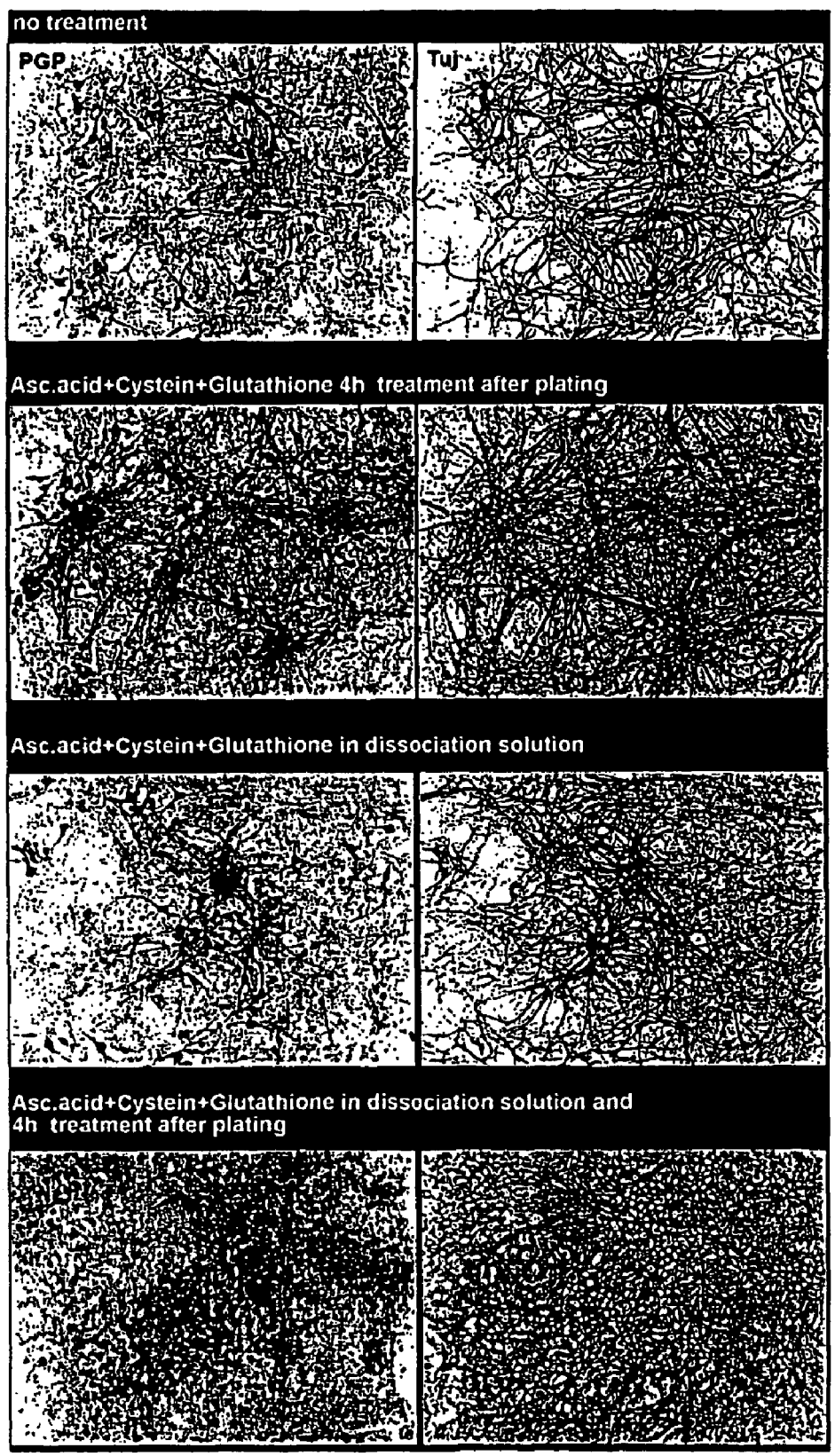
FIG. 11A shows PGP and Tuj immunohistochemical staining micrographs of fixed cortex cells isolated and cultured using a cell culture composition which lack antioxidants (upper panel) versus similar amounts of identical cells isolated and cultured with antioxidants comprising ascorbic acid, N-acetylcystine and glutathione about 4 hours after plating (upper middle panel); cells treated with ascorbic acid, N-acetylcysteine and glutathione during dissociation of the tissue into cells of interest (lower middle panel); cells treated with ascorbic acid, N-acetylcysteine and glutathione during dissociation and again about 4 hours after plating (lower panel).
Figure 11B:
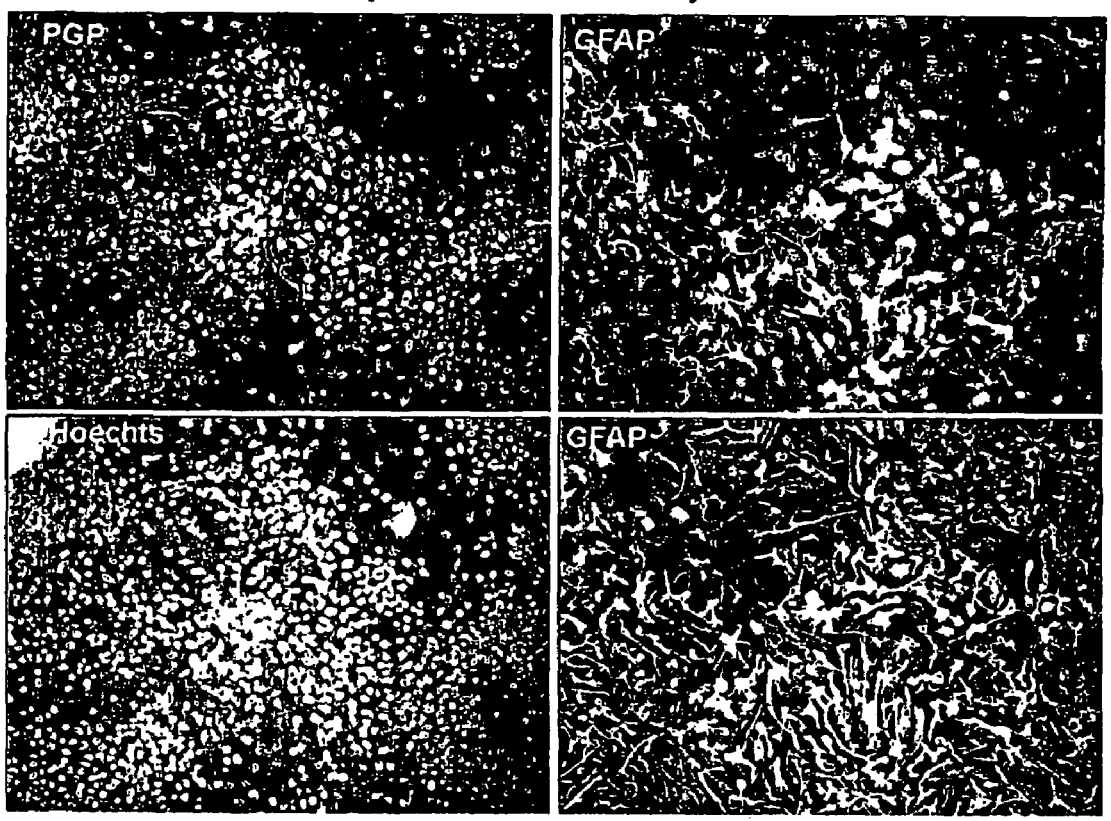
FIG. 11B shows PGP, GFAP immunohistochemical staining and Hoechst histochemical staining of CNS cell at 7 days in culture following cryopreservation, thawing and culturing using the CNS cell cryopreservation and CNS cell culture compositions of the present invention.

Referring now to FIG. 11A, there is shown PGP and Tuj immunohistochemical staining of fixed cortical cells which are isolated and cultured using a cell culture composition which lack antioxidants (upper pannel) in relation to similar amounts of identical cells isolated and cultured in the CNS cell culture composition of the present invention comprising ascorbic acid, N-acetylcystine and glutathione about 4 hours after plating (upper middle panel). Shown in the lower middle panel are cells treated with ascorbic acid, N-acetylcysteine and glutathione during dissociation of the tissue into cells of interest. Shown in the lower panel are cells treated with ascorbic acid, N-acetylcysteine and glutathione during dissociation and again about 4 hours after plating suggest that a combination of antioxidants, specifically ascorbic acid, cysteine and glutathione enhance viability of cells in culture. Referring now to FIG. 11B, there is shown PGP, and GFAP immunohistochemical staining and Hoechts histochemical staining of CNS cell at 7 days in culture following cryopreservation, thawing and culturing using the CNS cell cryopreservation and CNS cell culture compositions of the present invention. The results shown suggest that there is an increase in the number of supporting glial cells in culture when cells are treated with the CNS composition of the present invention comprising ascorbate, N-acetylcysteine and glutathione prior to cryopreservation and immediately following thawing. CNS cell cultures treated with the compositions of the present invention suggest that the compositions may enhance the viability and growth of glia (shown in FIG. 11B in two different focal planes) which appear to form elaborate three dimensional arrays amongst the neuronal cells, similar to that which occurs in vivo (not shown).

Figure 12:
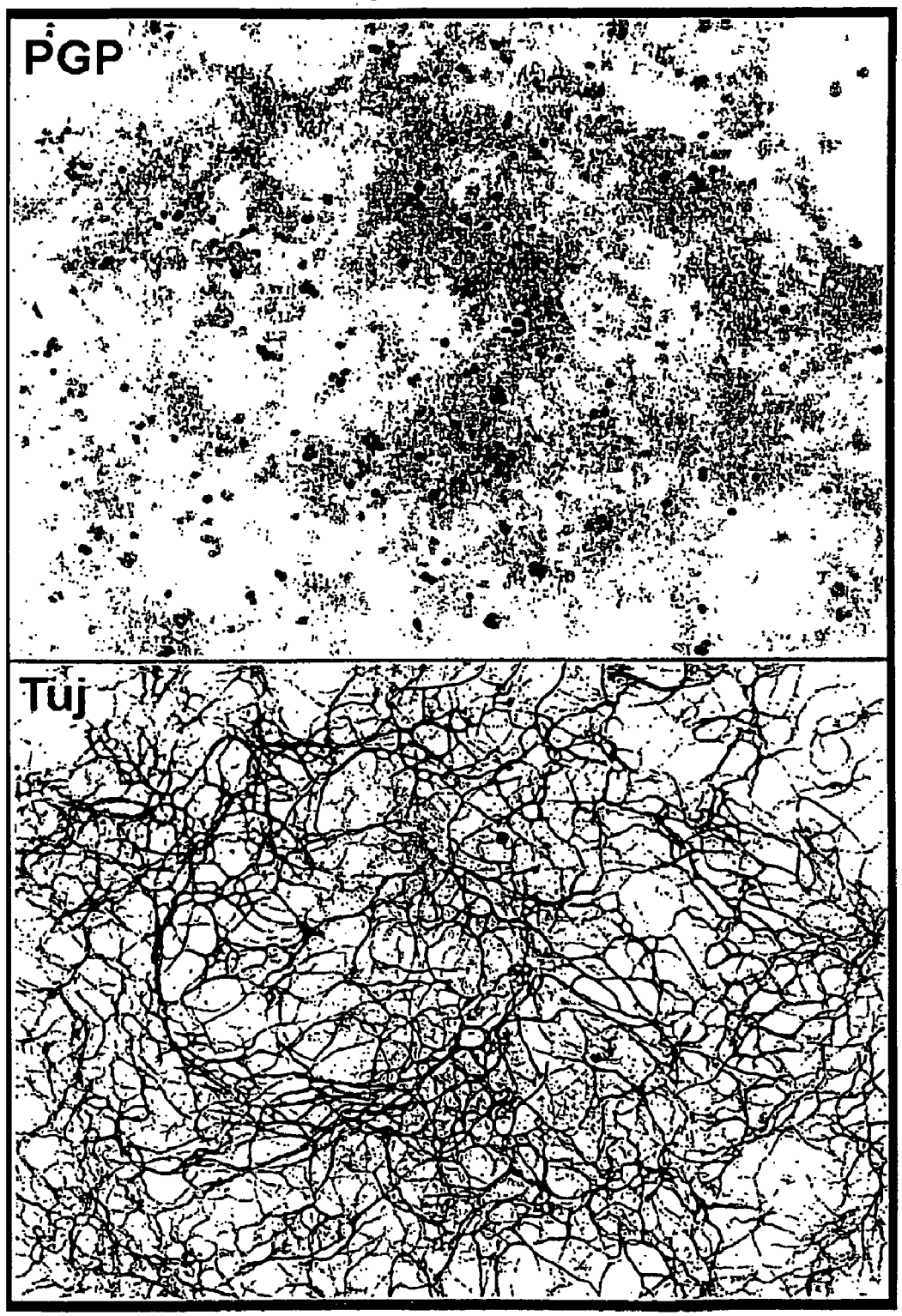
FIG. 12 shows PGP and Tuj immunohistochemical staining of fixed, dissociated mouse cerebellum cells following cryopreservation for about 9 months.
Figure 13A:
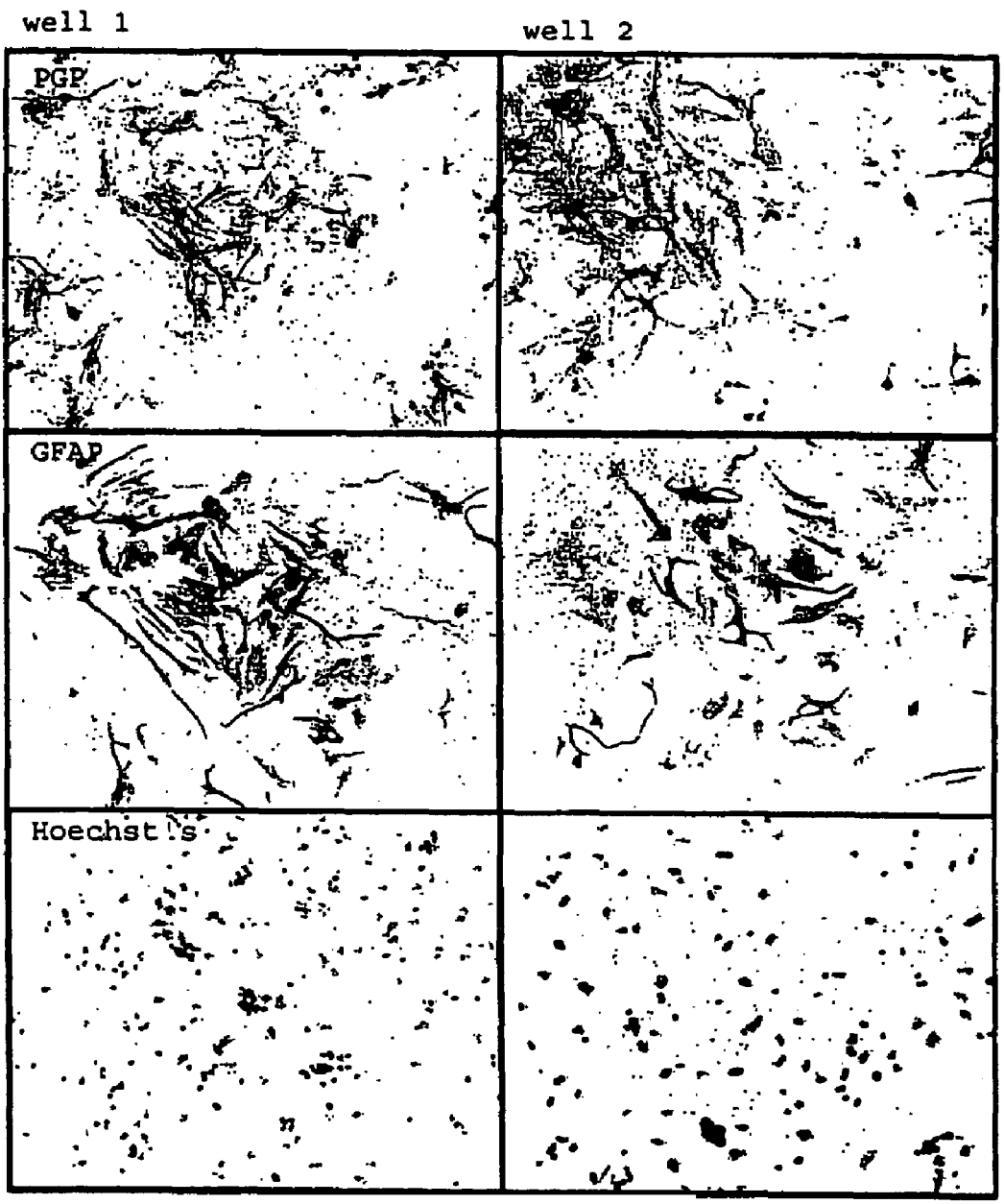
FIG. 13 shows PGP, GFAP and Hoechst's staining of rat cryopreserved cortex cells thawed by the various methods (FIG. 13A: hand thawed.
FIG. 13B: thawed at 37° C. for 5 minutes.
FIG. 13C: thawed at 37° C. for. 10 minutes.
FIG. 13D: thawing at 37° C. for 20 minutes.
FIG. 13E: thawed at 56° C. for 1 minute and 57 seconds.
FIG. 13F: thawed at 56° C. for 2.5 minutes.
FIG. 13G: thawed at 37° C. for 2.5 minutes.
FIG. 13H: thawed at 4° C. for 70 minutes. Not shown are cells subjected to a freezing-thawing freezing-thawing cycle.
Figure 13B:
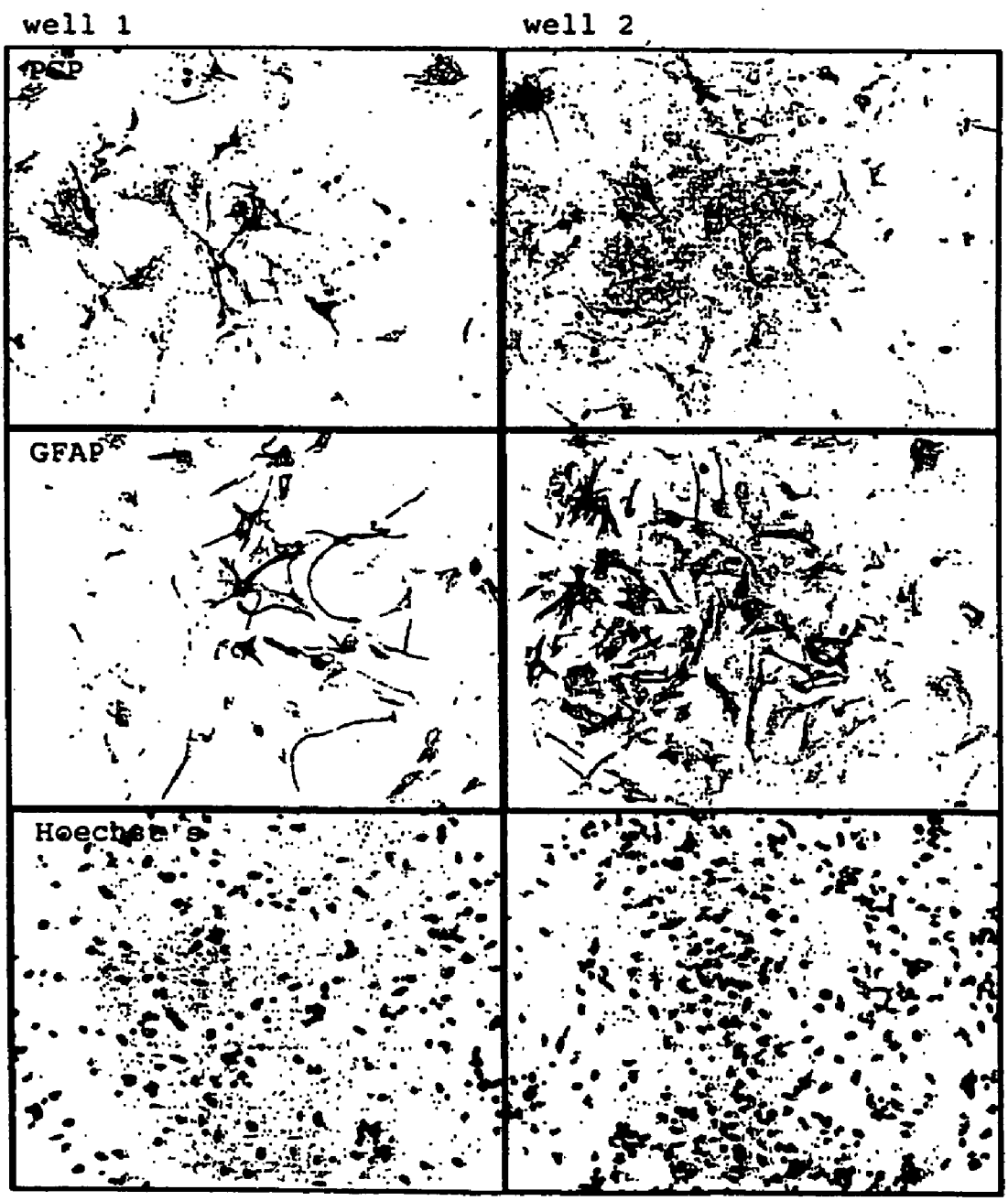
Figure 13C:
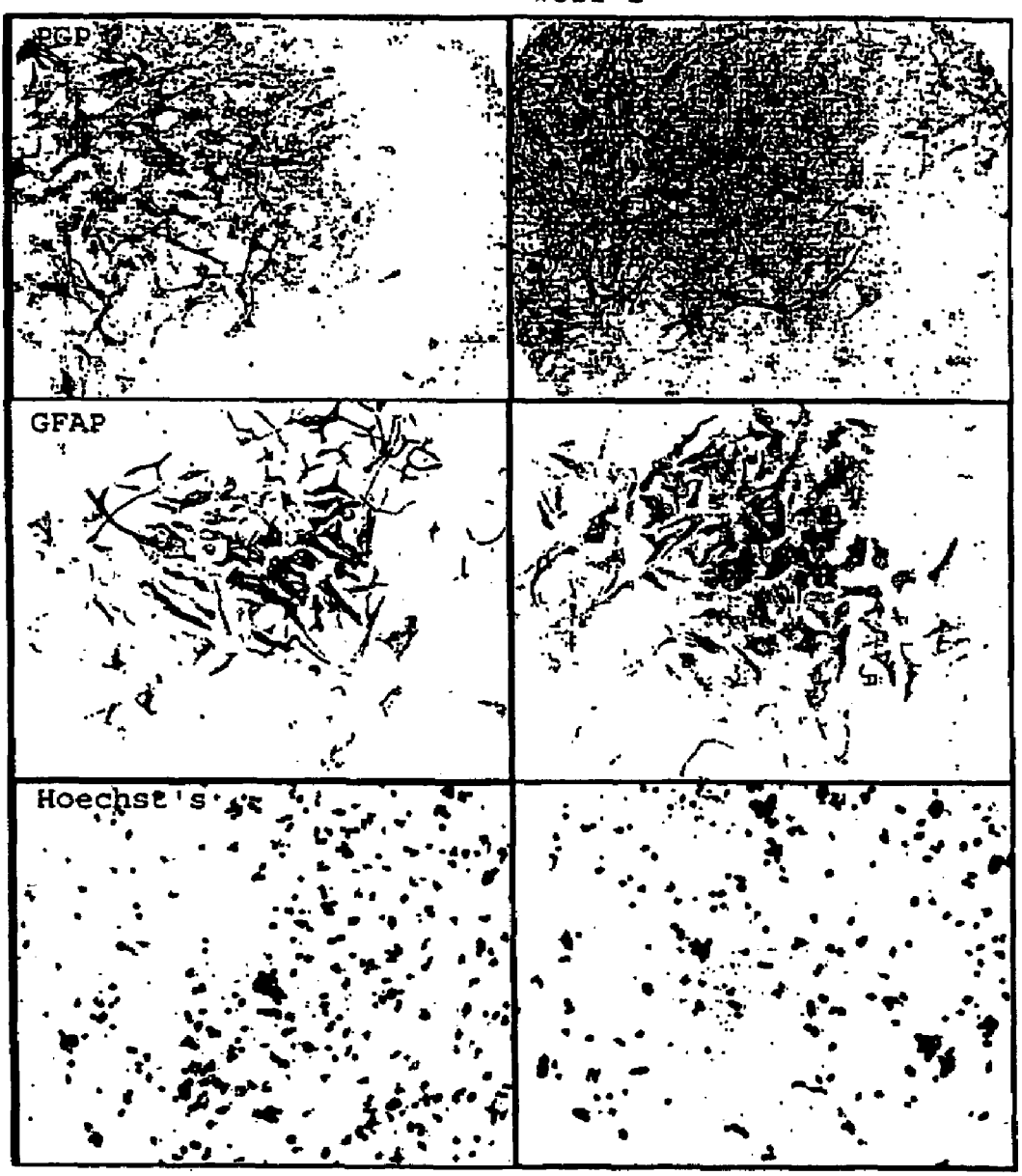
Figure 13D:
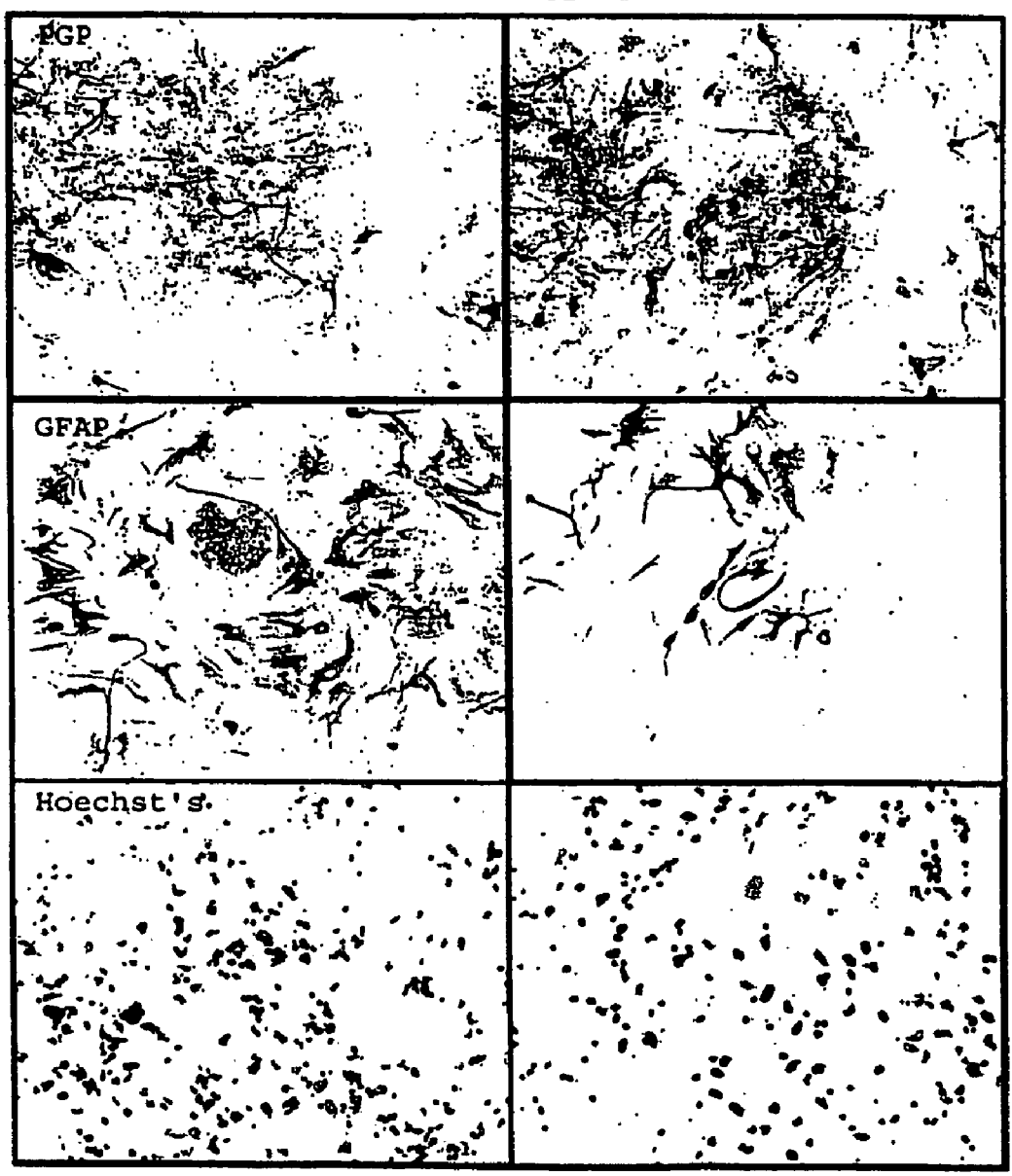
Figure 13E:
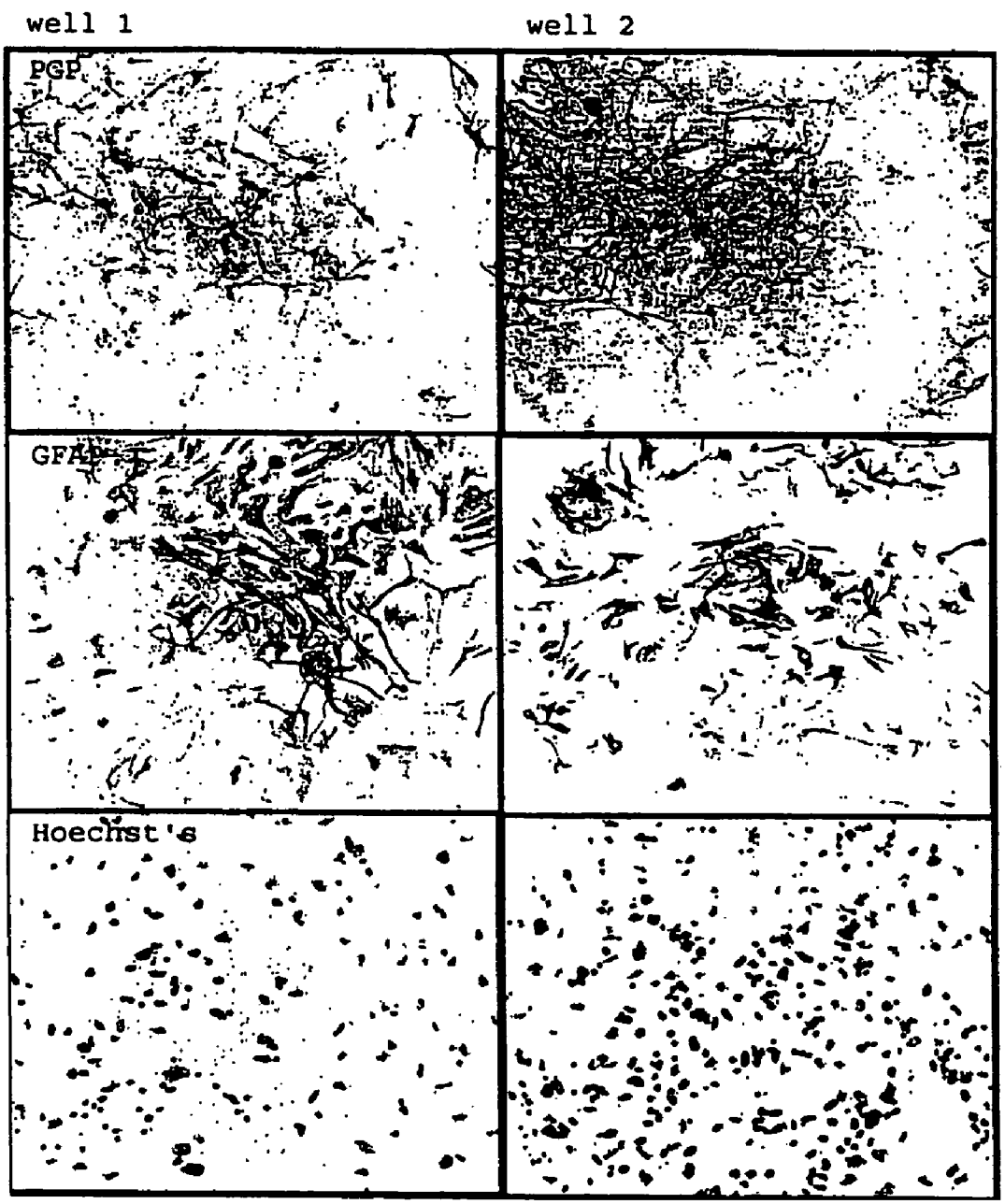
Figure 13F:
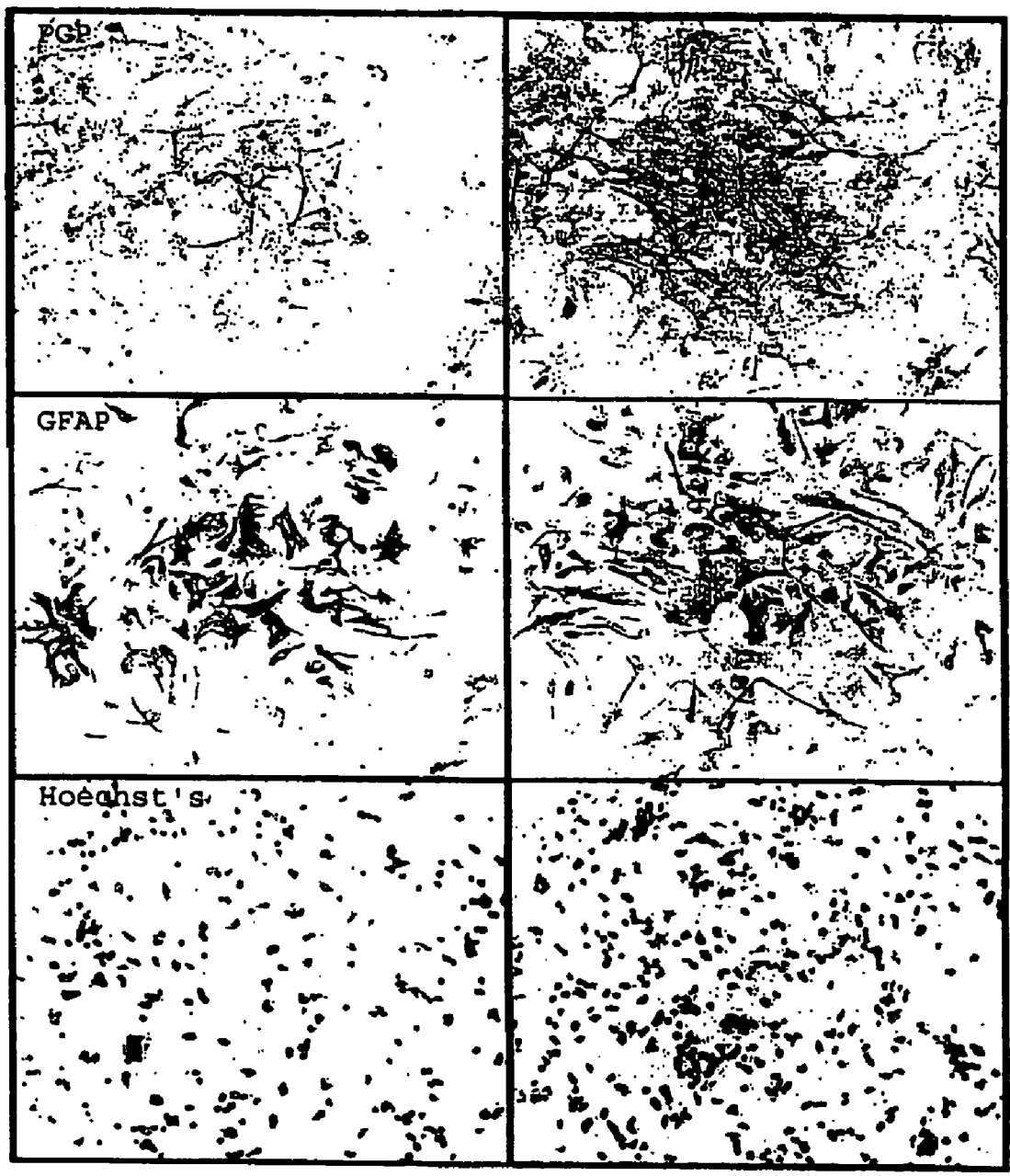
Figure 13G:
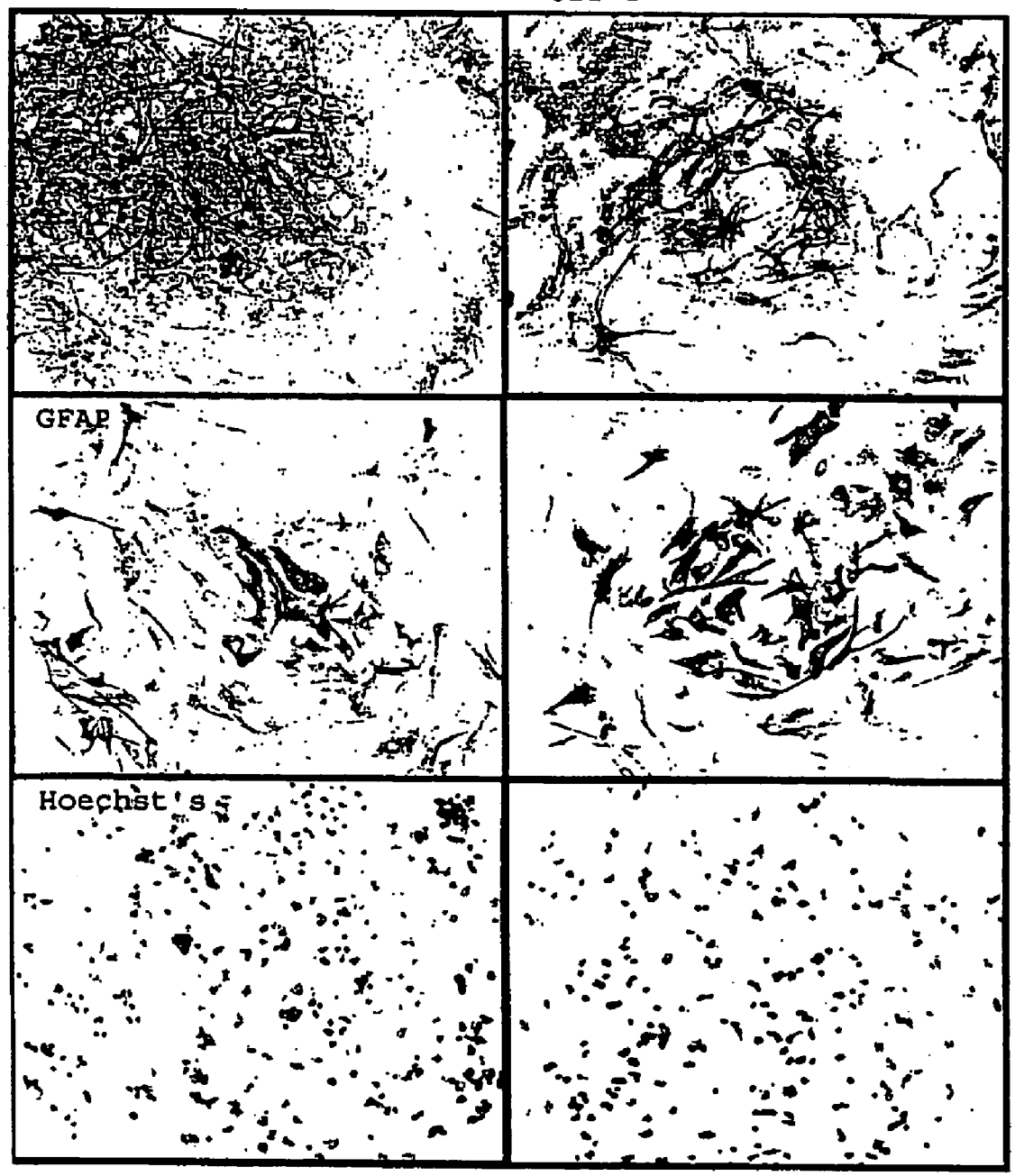
Figure 13H:
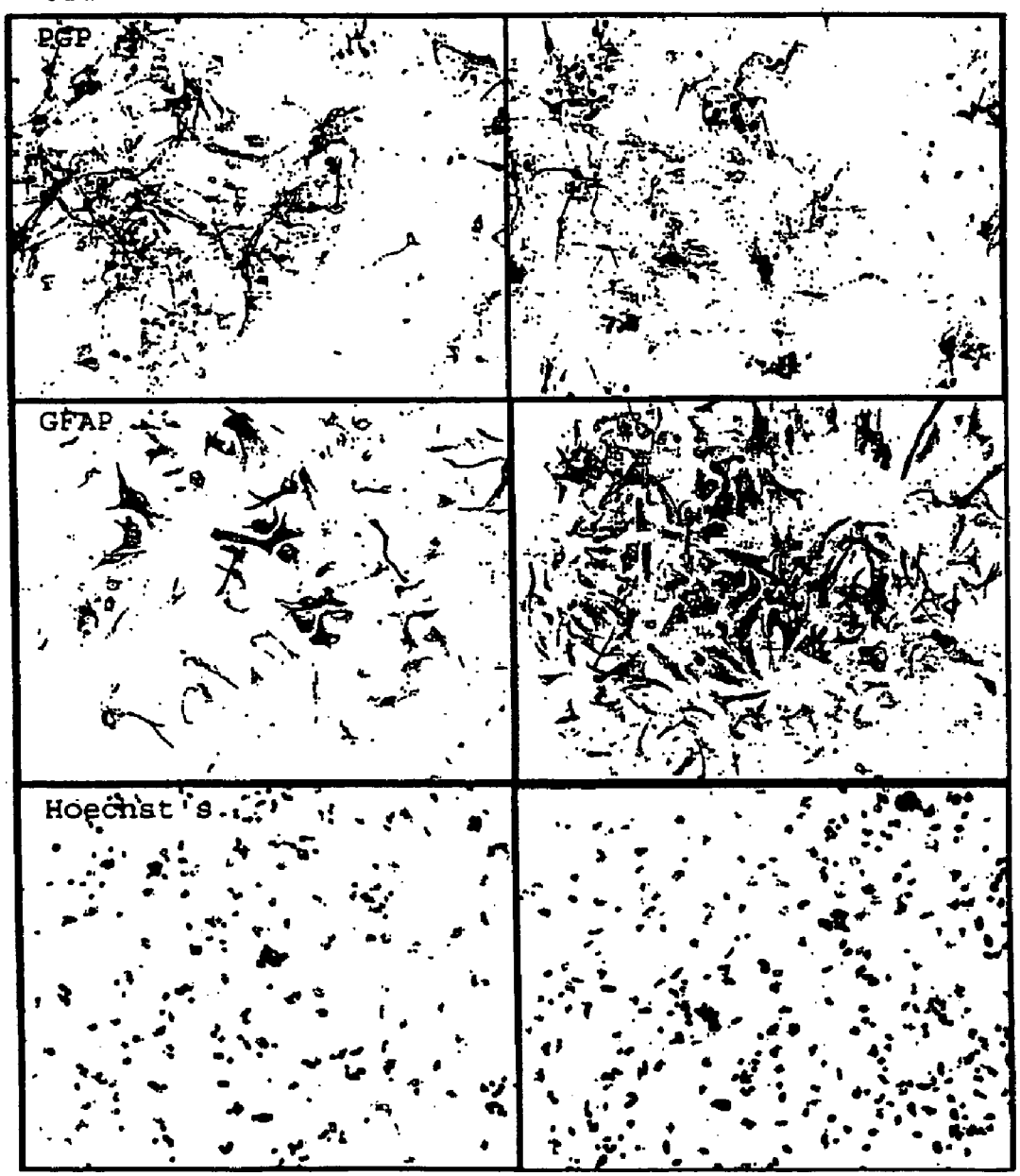

Referring now to FIG. 12, there is shown PGP and Tuj staining of fixed, dissociated mouse cerebellum cells following cryopreservation for about 9 months using the CNS cell cryopreservation composition of the present invention. The results shown in FIG. 12 suggest that the CNS cell culture composition and CNS cell cryopreservation composition of the present invention may be used to cryopreserve many types of cells. For example, but not wishing to be limiting, the CNS cell culture composition and CNS cell cryopreservation composition contemplates culturing and cryopreservation of CNS cells derived from cerebral cortex, striatum, hippocampus, cerebellar granular layer, glial cells, spinal cord cells, dorsal root ganglia, sympathetic neurons, and submucosal plexus. Further, other cells which maybe cultured using the CNS cell culture composition of the present invention include, but are not limited to retinal cells, cardiac myocytes, skeletal muscle cells, vascular smooth muscle cells, cerebral endothelial cells, pulmonary endothelial cells, and fibroblasts.

CNS cells which are cultured or cryopreserved using the CNS cell culture or CNS cryopreservation compositions of the present invention, respectively, may be derived from any animal, for example, but not limited to mouse, rat, hamster, cat, dog, human, bovine, porcine, equine, amphibian, chimpanzee, ape, aplysia, nematode, fish, or leech Further, the present invention contemplates culturing, cryopreserving or both culturing and cryopreserving CNS cells derived from transgenic animals. Without wishing to be limiting, the present invention contemplates culturing and cryopreserving cerebral cortex cells which are transgenic and express green fluorescent protein (GFP), GFP fluorescent hippocampal cells, cell repair impaired (GFP fluorescent) cerebral cortical cells, cell repair impaired (GFP fluorescent) hippocampal cells, GFP fluorescent striatum, GFP fluorescent hippocampus, GFP fluorescent cerebellar granular layer, GFP fluorescent glial cells, GFP fluorescent cardiac myocytes, GFP fluorescent skeletal muscle cells, GFP fluorescent pulmonary endothelial cells, cell repair impaired GFP fluorescent cardiac myocytes. Further, the present invention contemplates culturing and cryopreserving stem cells, including but not limited to neuronal stem cells using the CNS cell culture and the CNS cell cryopreservation compositions of the present invention.

Further, in an embodiment of the present invention which is not meant to be limiting in any manner, the present invention contemplates cryopreservation of co-cultures of cells and culturing of co-cultures using the cryopreservation and cell culture compositions of the present invention. By the term "co-cultures" it is meant a culture of cells which comprises at least two individual cell types, for example, but not limited to, striatum cells/substantia nigra cells, striatum/cortex cells, cortex/macrophage cells, or other combinations of other cells including, but not limited to cerebral cortex, striatum, hippocampus, cerebellar granular layer, glial cells, spinal cord cells, dorsal root ganglia, sympathetic neurons, and submucosal plexus. Further, other cells which may be co-cultured using the CNS cell culture composition of the present invention include, but are not limited to retinal cells, cardiac myocytes, skeletal muscle cells, vascular smooth muscle cells, cerebral endothelial cells, pulmonary endothelial cells, or a combination thereof. In an embodiment, the co-culture may comprise any combination of primary cells. Further the co-culture may comprise 3 or more cells. Further, the one or more cell types may comprise a stem cell type. Such co-cultures can be valuable in understanding the molecular mechanism of stem cell differentiation as a co-culture of cells may more accurately mimic the native environment of a stem cell than traditional in vitro conditions currently employed. Also contemplated are co-cultures wherein each individual cell type is labeled with a distinct fluorophore, dye or the like, to facilitate identification of the cell type. Fluorophores and dyes are known within the art and may be purchased from a variety of chemical suppliers. Preferably the fluorophore or dye does not affect the viability, or the normal metabolism of the cell type.

In another embodiment, the present invention contemplates cell culturing and cryopreservation of CNS cells derived from transgenic or knock-out organisms, which exhibit a specific genotype or phenotype. For example, but not wishing to be limiting, the present invention contemplates cells derived from transgenic organisms which exhibit symptoms of diseases, such as, but not limited to Alzheimer's disease.

The present invention further contemplates a kit comprising the CNS cell culture composition of the present invention, the CNS cryopreservation composition of the present invention or both. The kit may further comprise CNS cells which are cryogenically frozen using the CNS cryopreservation composition of the present invention. Also, the kit may comprise instructions for the culturing CNS cells, cryopreserving cells, thawing cells, culturing thawed cells or any combination thereof.

Also contemplated by the present invention is a method of enhancing commonality in neuronal research comprising,
  providing an individual, group or organisation that maintains a plurality of cryopreserved primary neuronal cells cultures, the individual, group or organisation capable of providing one or more samples of cryopreserved neuronal cell cultures to one or more researchers, such that the cryopreserved primary neuronal cell cultures may be thawed, cultured and employed, for example, but not limited to in research or other experiments by the one or more researchers.

Any of the primary cell cultures as disclosed herein and any of the cell cryopreservation and cell culturing compositions may be employed in the method. Further, instructions may be provided to aid in thawing and culturing the cryopreserved cell culture. Also contemplated by the method are kits which comprise one or more primary cell cultures, cell cryopreservation compositions, cell culture compositions, instructions, or any combination thereof.

Providing primary neuronal cell cultures that are derived from a common source and isolation method permits, without wishing to be limiting, the results of experiments by several researchers to be more directly compared and analysed as such results are derived from common stocks of primary neuronal cell cultures. Such a method may be a valuable tool in neuronal research.

The above description is not intended to limit the claimed invention in any manner. Furthermore, the discussed combination of features might not be absolutely necessary for the inventive solution.

The present invention will be further illustrated in the following examples. However, it is to be understood that these examples are for illustrative purposed only, and should not be used to limit the scope of the present invention in any manner.

EXAMPLES

Example 1

Preparation of Solutions and Culture Media

Preferably all culture media is prepared and stored for no longer than about 4-6 weeks, more preferably about 3 weeks. Still more preferably, all culture media is prepared fresh prior to use.

ENS Cell Culture Composition
Reagents:
  0.030 g cytosine arabinofluronoside in 100 ml distilled water
  0.0122 g uridine triphosphate in 100 ml distilled water
  0.246 g fluoro-2' deoxyuridine in 100 ml distilled water
  0.584 g glutamine in 20 distilled water
  6.0 g glucose in 20 ml distilled water
  Penicillin/Streptomycin (lyophilized) in 20 ml distilled water
  Rat serum (blood spun at 2500 rpm at 4° C. for 15 minutes)
  Minimum essential medium (MEM)

100 ml of ENS cell culture composition is prepared by adding 1 ml each of cytosine arabinofluronoside, uridine triphosphate, fluoro-2' deoxyuridine, glutamine, glucose, and Penicillin/Streptomycin solutions to 2.5 ml rat serum. MEM is added to the mixture to bring final volume to 100 ml. The solution is filtered into a sterile container using a 50 ml syringe and 2 filters and refrigerated in sterile environment. As will be evident to someone of skill in the art there exists numerous ways of combining components to arrive at the ENS cell culture composition of the present invention, without departing from the scope of the present invention, and are fully contemplated by the method of the present invention Further, the ENS cell culture composition may further comprise ENS cells.

ENS Cell Cryopreservation Composition

In an embodiment, the ENS cell cryopreservation composition of the present invention may comprise ENS cell culture composition and DMSO in a ratio of about 93:7 (v/v) respectively. As will be evident to someone of skill in the art there exists numerous ways of combining components to arrive at the ENS cell cryopreservation composition of the present invention, without departing from the scope of the present invention, and are fully contemplated by the method of the present invention. Further, the ENS cell cryopreservation composition of the present invention may comprise ENS cells.

Leibovitz's L 15 Washing Medium
Reagents:
  0.584 g glutamine in 20 distilled water
  6.0 g glucose in 20 ml distilled water
  Penicillin/Streptomycin (lyophilized) in 20 ml distilled water
  10% (v/v) Bovine serum
  Leibovitz's L 15 Medium 100 ml washing medium is prepared by adding 1 ml each of glutamine, glucose, and Penicillin/Streptomycin solutions to 10 ml bovine serum, followed by adding Leibovitz's L15 Medium to bring the final volume to 100 ml. The solution is filtered into a sterile container using a 50 ml syringe and 2 filters, and stored in a refrigerated, sterile environment.

Hanks 1× Solution (Non-Sterile)
Reagents:
 Hanks solution
 Sodium bicarbonate
 Distilled water
 175 ml of distilled water is added to 20 ml Hanks solution. The pH is adjusted to 7.3 with sodium bicarbonate and the solution is brought to a final volume of 200 ml with distilled water. The solution is kept refrigerated.

Krebs 10× Solution
Reagents:
 73.67 g sodium chloride (NaCl)
 3.85 g potassium chloride (KCl).
 1.66 g sodium biphosphate monohydrate (NaH$_2$PO$_4$.H$_2$O)
 2.45 g magnesium chloride hexahydrate (MgCl$_2$.6H$_2$O)
 3.68 g calcium chloride dihydrate (CaCl$_2$.2H$_2$O)
 20 g glucose
 21 g sodium bicarbonate
 To make Krebs 1× solution, Krebs 10× is diluted to 1× using distilled water and gassed with 95% CO$_2$, 5% O$_2$.

Dispase/Collagenase
 0.01 g of 245 unit/mg collagenase and 0.04 g of dispase is weighed into a dry 15 ml centrifuge tube. The composition is stored with desiccant and refrigerated.

L-Cysteine
 0.001 g L-cysteine is weighed into a 15 ml centrifuge tube. The tube is protected from light with aluminum foil and stored with desiccant.

0.1M Phosphate Buffered Saline (PBS)
 7.58 g NaCl
 3.26 g NaH$_2$PO$_4$—H$_2$O
 10.36 g Na$_2$HPO$_4$
 1L of 0.1M PBS is prepared by combining the above reagents with 900 ml of distilled deionized water, adjusting the pH to 7.4 and bringing the volume to 1L. The solution is autoclaved for 20 minutes and subsequently stored at 4° C.

General Cell Culture Medium (also Termed CNS Plating Medium)
 78 ml minimum essential medium (MEM)
 10% (v/v) heat inactivated horse serum (HS)
 10% (v/v) heat inactivated fetal bovine serum (FBS)
 20 mM D-glucose
 2 mM L-glutamine
 100 U Penicillin-streptomycin
 100 ml of the general cell culture medium is prepared by adding 10 ml of each horse serum and fetal bovine serum to D-glucose. 1 ml of each 200 mM L-glutamine and penicillin-streptomycin is added and the volume is adjusted to 100 ml with MEM. The general cell culture medium is filtered into a sterile container using a Nalgene 150 ml SFCA membrane 0.2 mM filter. The general cell culture medium is stored at about 4° C.

CNS Cell Culture Composition (also Termed CNS Plating Medium with ACG)
 78 ml minimum essential medium (MEM)
 10% (v/v) heat inactivated horse serum (HS)
 10% (v/v) heat inactivated fetal bovine serum (FBS)
 20 mM D-glucose
 2 mM L-glutamine
 100 U Penicillin-streptomycin
 400 mM ascorbic acid (A)
 2 mM glutathione (G)
 306 mM N-acetylcysteine (C)

100 ml of the CNS cell culture medium composition is prepared by adding 10 ml of each horse serum and fetal bovine serum to D-glucose. The appropriate amounts of glutathione, ascorbic acid, and N-acetylcysteine are added (in this order) in combination with 1 ml of each 200 mM L-glutamine and penicillin-streptomycin and the volume is adjusted to 100 ml with MEM. The CNS cell culture medium composition is filtered into a sterile container using a Nalgene 150 ml SFCA membrane 0.2 mM filter. The CNS cell culture medium composition of the present invention is stored at about 4° C. As will be evident to someone of skill in the art there exists numerous ways of combining components to arrive at the CNS cell culture medium composition of the present invention, without departing from the scope of the present invention, and are fully contemplated by the method of the present invention Further, the CNS cell culture medium composition may further comprise CNS cells.

CNS Cell Cryopreservation Composition
 78 ml minimum essential medium (MEM)
 20 mM D-glucose
 10% (v/v) heat inactivated horse serum (HS)
 10% (v/v) heat inactivated fetal bovine serum
 2 mM L-glutamine
 100 U Penicillin-streptomycin
 8% (v/v) DMSO
 400 mM ascorbic acid
 2 mM glutathione
 306 mM N-acetylcysteine
 10 ml of CNS cell cryopreservation composition may be prepared as follows: 10 ml of general cell culture medium is added to 6 mg of glutathione. The solution is dissolved and filtered. To 8.7 ml of the solution comprising glutathione is added 800 ml of DMSO, 400 ml of a 10 mM stock of ascorbic acid and 100 ml of a 30.6 mM stock of N-acetylcysteine. The solution is made about 10 minutes before use and allowed to equilibrate at 37° C. prior to use. As will be evident to someone of skill in the art there exists numerous ways of combining components to arrive at the CNS cell cryopreservation composition of the present invention, without departing from the scope of the present invention, and are fully contemplated by the method of the present invention. Further, the CNS cell cryopreservation composition of the present invention may comprise CNS cells.

Cortical Growth Medium
 89 ml Dulbecco's modified eagle medium (DMEM)
 10% (v/v) heat inactivated horse serum (HS)
 100 U penicillin/streptomycin
 100 ml of Cortical growth medium is prepared by adding 10 ml horse serum and 1 ml penicillin/streptomycin and the volume is brought to 100 ml with DMEM. The solution is filtered into a sterile container using a Nalgene 150 ml SFCA membrane 0.2 mm filter. The Cortical growth medium is stored at a temperature of about 4° C.

Example 2

Enteric Neuron Isolation, Culturing and Cryopreservation

A. Tissue Isolation
 Male Sprague Dawley rats 200-300 g (Charles River laboratories, Canada) are sacrificed by cervical dislocation according to Canadian Council on Animal Care guidelines, and a 30 cm segment of ileum isolated. This tissue is flushed with freshly-prepared gassed (95% CO$_2$, 5% O$_2$) Kreb's solution (7.36 g/L NaCl, 0.385 g/L KCl, 0.166 g/L $NaH_2PO_4$ ($H_2O$), 0.245 g/L $MgCl_2.6H_2O$, 0.368 g/L $CaCl_2.2H_2O$, 2.0 g/L glucose, and 2.1 g/L $NaHCO_3$) to remove intestinal contents, and the tissue is maintained in continuously-gassed Kreb's solution on ice until processed for dissection. Dissection of intestinal segments is visualized using a dissecting microscope, with tissue pinned out in glass dissection trays filled with oxygenated Kreb's solution. Segments (3 cm) of the ileum, cleared of adherent connective tissue, are cut longitudinally close to the point of mesenteric attachment and pinned out, muscle side upwards ready for fine dissection of the myenteric plexus/longitudinal muscle layers. Throughout dissection, the tissue is maintained immersed in continuously-gassed Kreb's solution. Using the blunt edge of curved forceps, the mucosal layer is carefully scraped away from underlying gut wall. Using fine forceps, the remaining mucosa, muscularis mucosae and circular muscle, together are carefully separated away from the myenteric plexus/longitudinal muscle layers underneath. Any remaining circular muscle fibres are carefully dissected away from the myenteric plexus.

B. Enzymatic Dissociation of ENS Cells

The isolated 'laminar preparations' of myenteric plexus/longitudinal muscle are enzymatically processed for cell dissociation under sterile conditions in a laminar flow culture hood. Isolated laminar preparations are placed in a container of 10 ml of filter-sterilized Hanks Balanced Salt Solution pH 7.3 containing 100 ml of papain II and 1.0 mg of L-cysteine. The preparations are incubated for 10 min. in a 37° C. water bath. The tissue is then rinsed in a washing medium composed of Leibovitz's L-15 medium comprising 10% fetal bovine serum, 2 mM L-glutamine, 15 mM glucose and 100 U penicillin-streptomycin, prepared as described in Example 1.

After rinsing, the tissue is incubated (37° C., water bath) for 10 min in 10 ml of Hanks Balanced Salt Solution containing 10 mg of collagenase type I and 40 mg of dispase II. The tissue in this solution is then gently triturated with a flame-polished Pasteur pipette until cells are dissociated. This medium of dissociated cells is centrifuged at 4° C. for 5 min. at 500 rpm, the supernatant removed from the precipitated cells, and the cells are resuspended in 8 ml of L-15 washing medium. Centrifugation is repeated for 5 min. at 500 rpm and 4° C., and the resultant precipitated cells resuspended in Cell culture composition composed of 90% MEM, 2.5% rat serum, 2 mM L-glutamine, 15 mM glucose, 100 U penicillin-streptomycin, 10 mM fluorodeoxy-uridine, 1 mM cytosine arabinoside and 0.5 mM uridine triphosphate.

C. Freezing ENS Cells

125 µl of the 14% DMSO is placed into a labelled 1.8 ml volume cryovials and set aside. The tube containing the dissociated cells is cleared of supernatant using a vacuum pump. 1 ml of cell culture composition is added to the tube and the cells are gently re-suspended. 125 µl of the cell suspension is then transferred to a 15 ml volume centrfuge tube and 300 µl of Cell culture composition added. With the cell suspension thoroughly mixed, the suspension is transferred to cryovials containing 14% DMSO (ratio is 120 µl suspension to 125 µl of DMSO) giving a final concentration of 7% v/v DMSO and these are placed in a Nalgene "M. Frosty" 1° C. freezing container in a ~80° C. freezer overnight. In an alternate embodiment, the cells maybe frozen with the aid of a computer integrated freezing system, for example, but not limited to the system available from Thermoforma The cryovials are then transferred to long term liquid nitrogen storage.

D. Thawing ENS Cells

A cryovial of cells stored in liquid nitrogen is removed and placed in a 37° C. water bath for 3 min. In a sterile laminar flow hood, 300 µl of 37° C. ENS cell culture composition is added. The cells are re-suspended and mixed well. 100 µl aliquots of cell suspension are removed for cell culture. Plated cells are kept in a 37° C. incubator (gassed with 95% $CO_2$, 5% $O_2$) for at least six hours. After six hours, ENS cell culture composition (37° C.) is added and the cells returned to the incubator.

E. ENS Cell Culture

ENS cell suspensions (freshly prepared or thawed cryopreserved cells) are plated at about $10^3$ cells/$mm^2$ onto glass cover slips or sterile glass LabTek chamber slides (VWR Canlab) coated with Matrigel matrix (VWR Canlab). Cultures are maintained at 37° C. in an incubation chamber (gassed with 95% $CO_2$, 5% $O_2$), and ENS cell culture composition is changed after the initial 24 hr incubation and every subsequent 72 hrs. The cell cultures are observed microscopically using phase contrast upon plating and every subsequent 24 hrs to monitor the progression of cell adhesion and process extension. Preferably, cultures are removed from their incubator for periods less than about 10 min. ENS cultures are generally used in experiments about seven days after plating.

F. Immunohistochemistry

ENS cells are fixed in 4% paraformaldehyde (w/v) comprising 0.2% picric acid (w/v), 0.1 M sodium phosphate buffer (pH 6.9) for 60 min. The cells are then rinsed several times and kept in 0.01 M sodium phosphate buffered saline (PBS) at 4° C. Coverslips are removed from 24-well tissue culture plates with fine forceps and excess PBS is removed with tissue. The cover slips are placed onto microscope slides and glued on the slide by applying nail polish to the edge of the coverslip. PBS is added to the coverslip to prevent the sample from drying out. The coverslips are incubated with the primary antibody at working dilution overnight at 4° C. The primary antibodies are diluted in 0.3% Triton X-100 (Sigma) in 0.01 M PBS. All incubations carried out in humidified chambers. The sample are rinsed in 0.01 M PBS after primary antibody incubation for a minimum of 3 times, each for a period of 10 minutes. The primary antibodies are visualized using fluorescence conjugated secondary antibodies at the appropriate working dilution. Secondary antibodies are incubated with cells for 40-60 min at 37° C. in humidified chambers. Labelled cell samples are mounted in 0.9% sodium chloride-glycerol (1:10) containing p-phenylenediamine (1 mg/ml).

Microscopy: The immunohistochemical staining patterns of the cells may be evaluated by any method known in the art. Immunohistochemical staining pattern are evaluated using a Zeiss Axiophot II microscope equipped with an epifluorescence (Hg-lamp) lamp and appropriate filter sets (excitation/emission) for the fluorophores (FITC: 490/525 nm, Texas Red: 590/620 nm). Digital images of the cultures are captured using Northern Eclipse software and are printed unaltered except for text labeling, brightness/contrast correction and inversion to a negative image. Live cultures are routinely monitored for growth by microscopy using an inverted microscope and phase optics—after fixing and immunostaining cultures are examined for morphology using Normaski contrast optics with low glycerol mounting medium to preserve refractive index differences within the cell cultures.

Cell counts of immunohistochemically stained cultures: Cells are counted from five arbitrary areas (fields) of each coverslip. Fields/locations are the same for each coverslip and include 4 cardinal peripheral fields and the center of the coverslip. Each area is photographed using fluorescence microscopy and a 20× objective. Digital images are analyzed using Northern Eclipse software (manual count tool). To enable counting of clusters of cells, the area of the coverslip shown in the image is viewed simultaneously through the microscope. In all experiments, two coverslips from each treatment group are counted and the data sets are graphed.

Morphological identification of cell types: A rabbit polyclonal anti-neuron-specific enolase (NSE) primary antibody (1:400 dilution) (Dako) is used in conjunction with a secondary Cy3-conjugated donkey anti-rabbit antibody, diluted 1:100 (Jackson), for visualization of enteric neurons. A rabbit polyclonal anti-glial fibrillary acidic protein (GFAP) primary antibody (1:400 dilution) (DakoPatts) is used with a secondary FITC-conjugated donkey anti-rabbit IgG diluted 1:80 (Chemicon) for glial cell visualization. A mouse monoclonal anti-vimentin primary antibody (1:800 dilution) (Boehringer Mannheim), is bound by a secondary Cy3-conjugated sheep anti-mouse IgG diluted 1:100 (Sigma). Both enteric glial cells and fibroblasts positively stain for the presence of vimentin, facilitating morphological identification and differentiation of these cell types in culture.

For other immunohistochemical studies, a mouse monoclonal anti-smooth muscle actin primary antibody (1:100 dilution) is used with a secondary FITC-conjugated goat anti-mouse IgG (1:80 dilution) (Am Qualex) for smooth muscle cell visualization. A rabbit polyclonal anti-macrophage primary antibody (1:400 dilution) (Accurate), which labels macrophages, and a rabbit polyclonal anti-histamine primary antibody (1:200 dilution) (Incstar), which labels mast cells, gut endocrine cells and blood cells, are both bound by a secondary FITC-conjugated donkey anti-rabbit IgG (1:20 dilution) (Amersham). A mouse monoclonal anti-ckit primary antibody (1:200 dilution) (Santa Cruz) is used in conjunction with a secondary FITC-conjugated goat anti-mouse IgG (1:20 dilution) (Am Qualex) for visualization of interstitial cells of Cajal.

Immunohistochemical characterization of neuronal subtypes: A rabbit polyclonal anti-nitric oxide synthase (NOS) antibody (1:400 dilution) (Santa Cruz), a rabbit polyclonal anti-vasoactive intestinal polypeptide (VIP) antibody (1:400 dilution) (Peninsula), a rabbit polyclonal anti-met-enkephalin (Met-Enk) antibody (1:500) (Beldo), and a rabbit polyclonal anti-gamma aminobutyric acid transaminase (GABA-T) antibody (1:400 dilution) is used. For all of these primary antibodies, a Cy3-conjugated donkey anti-rabbit secondary antibody (1:100 dilution) (Jackson) is employed. Finally, a mouse monoclonal anti-somatostatin (SOM) antibody (1:100 dilution) is used in conjunction with a secondary FITC-conjugated goat anti-mouse IgG (1:20 dilution) (Am Qualex).

NOS histochemistry: NADPH-diaphorase histochemical staining for nitric oxide synthase (NOS) activity is performed according to the method of Nichols et al., 1994, which is herein incorporated by reference. Fixed cultures are rinsed in 10 mM PBS, NO synthase reaction medium (1 mM NADPH, 0.5 mM nitroblue tetrazolium, 0.3% Triton X-100 in 10 mM PBS (pH 8.0)) is applied, and culture slides incubated in a dark, moist chamber at 37° C. for 1 hr. Slides are rinsed in 10 mM PBS for 15 min., and in decreasing concentrations of 100 mM PBS, 50 mM PBS, 25 mM PBS, and 12.5 mM PBS for 1 min. each. Each slide is air-dried and a coverslip is mounted thereupon using Tris-Glycerol 1:3. The histochemical product for NADPH-dependent diaphorase, indicating NOS activity, is photographed under bright-field conditions.

Quantitation: Cultures of cryopreserved cells are compared to fresh non-frozen myenteric cell cultures from the same animal. Cell survival is assessed 7 days after plating. Dissociated cells are evenly aliquoted amongst cryovials and culture slides, to ensure that the number of cells in the non-frozen and frozen cell cultures, are approximately equal. For quantitation, neurons stained for anti-neuron-specific enolase (NSE) are counted manually.

Hoechst 33258 histochemistry stains the nuclei of all cells present, may be used in the determination of total cell numbers in culture. In this procedure, 2.5 mg/mL Hoechst 33258 is applied to immunohistochemically-stained cultures for 10 minutes at room temperature. Slides are then rinsed in 10 mM PBS and mounted under a diluted fluorescence fade-retarding mounting medium (1 mg/ml p-phenylenediamine in 0.9% NaCl, 10% glycerol). Total cell numbers are counted manually.

Apoptotic cells, visualized with Hoechst 33258 staining, exhibit characteristic chromatin condensation, and are excluded from total numbers of surviving cells. Immunohistochemically-identifiable neurons exhibiting apoptotic chromatin condensation are also excluded from total numbers of surviving neurons.

Cell survival in cultures of cryopreserved cells maybe expressed as a percentage of cell survival in unfrozen control cell cultures. Analysis is performed using one-tailed Student's t test, with significance considered established at $p<0.05$.

Upon plating, uniform rounded cells devoid of processes occurring either singly or in small clumps, rapidly precipitate to the bottom of chamber wells. By about 24 hrs, non-viable cells and cell debris may be seen floating within the cell culture composition, while aggregates of viable cells are attached to the culture substrate. Also, some glial cells (identified by initial cell body flattening and cytoplasmic expansion) may be attached to the substrate. Although the majority of cells continue to exhibit a uniform rounded appearance, a small number of cells extend short processes. By about 48 hrs after plating, cells flatten onto the culture substrate and demonstrate clear cell-type morphologies. Smooth muscle cells, lymphocytes, macrophages, mast cells, endocrine cells, and interstitial cells of Cajal normally present within the intact adult rat ileum, are depleted in the primary cell cultures (not shown).

Neurons cluster together to form aggregates, often extending several branching processes which are enpassant with many other cell bodies, processes or both within the same cluster or in neighboring neuronal clusters. The growth patterns of enteric neurons suggest that these cells adhere to and grow over glial cells. Fibroblasts maybe present in cultures, however, upon careful dissection of the tissue of interest, the number of contaminating fibroblasts remain low. The enteric neurons continue to extend branching processes, and by about 7 days in culture form complex networks of interconnecting 'ganglia-like' structures.

Immunohistochemical staining of primary cell cultures with anti-neuron specific enolase suggest that primary ENS cell cultures are morphologically similar to their unfrozen counterparts (FIG. 1A). Enteric glia contain the intermediate filament protein GFAP, and anti-GFAP staining suggests large glial cell aggregates in cultures prepared according to the method of the present invention (FIG. 1B). Staining for the presence of the mesenchymal intermediate filament protein vimentin, suggests the presence of small numbers of morphologically-identifiable fibroblasts (FIG. 1C). These cells are generally present in isolated small clusters, and constituted less than about 10% of the total cell population in culture.

Staining for typical enteric neuronal subtypes, as indicated by neurotransmitter localization, including VIP (anti-vasoactive intestinal peptide), SOM (anti-somatostatin), and NO (anti-nitric oxide), suggest that many types of neuronal cells are present in cryopreserved cell cultures (FIG. 2A), with frequencies and morphological characteristics similar to those in the unfrozen control cell cultures (not shown).

Nitric Oxide (NO) neuron activity (demonstrated by NADPH-diaphorase staining for NO synthase activity) is also evident in cryopreserved, thawed cell cultures FIG. 2B). Immunostained and diaphorase stained neurons correspond with those identified morphologically as neurons with Dogiel Types I and II morphologies which normally present in the mammalian myenteric plexus in vivo.

Quantitative evaluation of the cultures established from cryopreserved cells suggests that cell viability does not significantly differ from control cultures plated directly from unfrozen cells (FIG. 3). In addition, the cultures established from cryopreserved cells display similar morphological and neurochemical characteristics to unfrozen control cell cultures.

The cryopreserved myenteric neurons in culture also display functional similarities. Cryopreserved cells which are thawed and cells that do not undergo cryopreservation exhibit AH- and S-type electrophysiological responses (FIG. 4) which are similar to those observed by myenteric neurons in vivo. Patch Clamp electrical recordings were performed on 10 day old cultures of rat cortical neurons treated with the above cryopreservation protocol and stored frozen for 105 days (FIG. 4B). These recordings were compared to recordings obtained from 10 day old control 'unfrozen' cortical cells, cultured fresh from the same cortex (FIG. 4A). The electrophysiological characteristics of cryopreserved cortical neurons in culture are similar to those obtained using 'sister' cultures of unfrozen cells Example 3

CNS Cell Isolation, Culturing and Cryopreservation

A. Animals

Timed pregnant female Sprague-Dawley from Charles River are used. Rats are housed singly in type IV Macrolone cages (57×35×17 cm) with wood shaving bedding which is changed twice a week. A 12 h light/dark schedule is used and the room temperature is maintained at 20±0.5° C. with a relative humidity of about 40-50%. Timed pregnant animals are delivered to a vivarium in the second week of gestation and maintained on standard rodent chow and water till E9 Animals are housed, handled and sacrificed in accordance with the guidelines of the Canadian Council on Animal Care (CCAC).

B. Tissue Dissection

All work stations are thoroughly sterilized with UV light and 70% ethanol before use.

The dissected regions are transferred immediately to culture dishes containing PBS kept on frozen ice packs. After 16 cortices have been collected, the culture dish is placed in a temperature monitored refrigerator and is kept under those conditions until the dissection process is completed. All steps from the trituration to the aliquoting are performed on ice. The cryovials are labelled prior to dissection and kept in a temperature monitored refrigerator before and after filling.

A rat is sacrificed by cervical dislocation and placed in a pre-cleaned flowhood. The abdomen is washed with 70% ethanol, opened (using large scissors) and the embryonic sacs removed (large forceps) and transferred to cold sterile PBS (0.1 M). Each sack is opened and the embryo removed and transferred to sterile cold PBS. The head is separated using small scissors and transferred to cold, sterile PBS. The heads are transferred to a new pre-cleaned flowhood where the brains are removed by opening up the skull using 45° angled trident scissors and by peeling the scalp and cranial bones off to the sides using curved forceps. The brain is gently scooped out of the cranial cavity (back end of the curved forceps) and placed into cold sterile PBS. The head is held in place through the dissection by the tips of the straight forceps placed into the cranial orbits. The dissected brains (in sterile cold PBS) are transferred to a pre-cleaned flowhood equipped with a dissecting microscope (Zeiss Stemi DV4). Each brain is moved over to fresh sterile cold PBS and placed under the microscope. The arachniod mater is removed with a curved forceps. This procedure reduces red blood cell contamination. The olfactory bulbs are removed and the caudate and putamen dissected away from the cortex (curved forceps) and transferred to sterile cold PBS. Unwanted tissue (hippocampus, basal forebrain) is removed from the cortex, and the cortex is then transferred to fresh sterile cold PBS. The total cell number obtained per embryo is about 10 million for the cortex and about 4 million for the caudate putamen.

C. Dissociation of CNS Cells

Cortices and striata (caudate putamen) are collected in cold PBS (approximately 2 mls in 35 mm petri dish) and transferred to a precleaned laminar flow hood. The tissue and PBS are gently drawn into a 10 ml pipette and transferred to a 15 ml tube. An equal volume of a cell culture medium comprising EM+20 mM D-glucose+2 mM L-glutamine+10% (v/v) heat inactivated fetal bovine serum (FBS)+10% (v/v) heat inactivated horse serum (HS)+1 U/mL penicillin streptomycin) is added to the tube and it is spun for 6 min at 11,000 rpm. The cell culture medium may also comprise the CNS cell culture medium composition of the present invention. Supernatant is removed and cell culture composition (comprising a volume of about 1 ml less than the number of brains dissected) is added to effect a superficial rinse. A 10 ml pipette is used to gently triturate the cells between about 10 and about 14 times. Preferably no bubbles are created in performing this step. CNS cells derived from tissue prepared according to the method of the present invention appears cloudy suggesting the presence dissociated cells in suspension. Preferably, the CNS cell suspension contains little visible particulate matter. In the event that particulates are present, the tissue may be gently triturated up to about 4 additional times. Following this step, the contents of the tube are allowed to stand for about 1 min allowing tissue aggregates to settle out of solution. The solution is subsequently transferred to a second tube leaving any tissue aggregates behind. To quantitate the number of cells in the solution an aliquot of the solution may be removed for counting.

CNS Cell counting: The concentration of CNS cells per ml of solution may be estimated by mixing 50 µl of trypan blue with 50 µl of CNS cell suspension, withdrawing 10 µl of this mixture and counting the cells in a hemocytometer. Specifically, CNS cells in the four corners of a hemocytometer may be counted. The cell concentration in the suspension may be estimated using the following formula: (# of cells/# of corners counted×dilution factor×$10^4$=# of cells/ml). However, as would be evident to someone of skill in the art, there are other methods known in the art to estimate the concentration of cells in suspension. Any of these cell counting methods may be employed in practising the present invention.

C. CNS Cell Culture

An estimate of the number CNS cells per ml is performed as discussed previously herein. Based on this estimate, an aliquot containing about 2,000,000 CNS cells is diluted to a final volume of about 4 ml with the CNS cell culture medium composition of the present invention. 1 ml is added to each well of a 24-well sterile tissue culture plate (Sarstedt) that contains a round 12 mm glass coverslip (Fisher Scientific) coated with Matrigel (Becton Dickinson). The cell culture plates are placed in a 37° C. incubator with 5% $CO_2$ in air atmosphere. Four hours after plating the CNS cells, the CNS cell culture medium composition of the present invention is removed and fresh 37° C. CNS cell culture medium composition is added (without antioxidants). Mitotic inhibitors (Sigma) are added at day 4 at a concentration of 15 μg/ml of fluorodeoxyuridine and 35 μg/ml of uridine triphosphate in the cell culture composition. On day 7, half the cell culture composition is removed and replaced with growth medium (DMEM+10% heat inactivated HS+100 U penicillin streptomycin) at 37° C. or the cultures are fixed with 4% paraformaldehyde (w/v) and 0.2% picric acid (w/v) in 0.1 M sodium phosphate buffer (pH 6.9) for. 60 min for immunohistochemistry.

Preparation of coverslips Coverslips (round, 12 mm, Fisher Scientific, thickness=1) are soaked in 3% HCl in distilled water for 1-24 hours. After an appropriate period the coverslips are rinsed in culture grade water 0.10 times, soaked in 1% sodium carbonate in distilled water for 1-2 hours, rinsed in culture grade water 10 times, dried in a 100° C. hot air oven (Stable-Therm, Fisher Scientific) for 1 hour and then sterilized in a 260° C. hot air oven for 2 hours. A 1 ml aliquot of Matrigel (1:10 in MEM, stored at −20° C.) is thawed at +4° C., and added to wells of the 24 well tissue culture plate containing 1 sterile coverslip per well. Matrigel or other suitable coating is applied to the area used for cell growth. Substrates coated with Matrigel are placed in a 37° C. incubator for at least 30 min prior to applying cells.

D. CNS Cell Freezing

CNS cells in CNS cell culture medium composition of the present invention are centrifuged at 11,000 rpm for 6 min. The supernatant is removed and the CNS cells are suspended in the cell cryopreservation composition of the present invention (CNS cell culture medium composition+8% DMSO+400 μM Ascorbic acid+2 mM Glutathione+50 μg/ml N-acetylcysteine at approximately 5,000,000 cells/ml. Subsequently, approx. 1 ml of the mixture is gently dispensed into 2.0 ml Nalgene cryovials. To avoid inter-tube variability only two 1 ml aliquots are removed at time and dispensed into cryovials. The cell suspension is re-suspended 1-2 times before the following two aliquots. The vials are then placed into a controlled rate freezing apparatus, for example, but not limited to the computer interfaced freezing system from Thermoforma, frozen, and maintained at −80° C. for at least 4 h. The vials are then subsequently transferred to long term liquid nitrogen storage.

E. Thawing of CNS Cells

Frozen CNS cell suspensions are rapidly thawed by placing vials into a 37° C. water bath for 3 min. Using a 10 ml pipette, the CNS cells are transferred to a sterile 15 ml tube and the desired volume of 37° C. CNS cell culture medium composition is added drop by drop (over a period of about 2 min) while continually rotating the tube. The cell suspension is gently resuspended 5-6 times and plated using about 1 ml/well in a 24-well sterile tissue culture plate (Sarstedt) containing a round 12 mm glass coverslip (Fisher Scientific) coated with Matrigel (Becton Dickinson). To avoid CNS cells from settling at the bottom of the tube during plating, only 2 mls are removed at a time and the vial containing CNS cells is re-suspended 1-2 times between plating. The plates are placed in a 37° C. incubator with a 5% $CO_2$ in air atmosphere.

4 h after plating the CNS cell culture medium composition of the present invention is removed with a pump and fresh 37° C. CNS cell culture medium composition is added. A CNS cell culture medium composition comprising mitotic inhibitors (Sigma) is added at day 4. On day 7, half the CNS cell culture medium composition is removed and replaced with a growth medium (DMEM+10% heat inactivated HS+100 U penicillin streptomycin) at 37° C. or the cultures are fixed with 4% paraformaldehyde (w/v) and 0.2% picric acid (w/v) in 0.1 M sodium phosphate buffer (pH 6.9) for 60 min for immunohistochemistry.

Immunohistochemistry of CNS Cell Cultures

Immunohistochemical markers used to analyze CNS cultures may include Tuj 1 and PGP 9.5. Tuj 1 is directed against a juvenile form of tubulin, is neuron specific and a marker for neuronal processes such as axons and dendrites. PGP 9.5 is directed against a neuron specific ubiquitin terminal carboxylase which may comprise up to about 2% of neuronal cytoplasmic protein. PGP 9.5 labels the cell body and dendritic compartments of neurons. The histochemical and immunohistochemical techniques used to study CNS cells is identical to the techniques used to study ENS cells, as described above. The results of immunohistochemical staining and other studies of CNS cells cryopreserved using the method of the present invention, the CNS cell cryopreservation composition and CNS cell culture medium composition of the present invention are shown in FIG. 5 through FIG. 12.

Antioxidants such as ascorbic acid, glutathione and N-acetylcysteine improve CNS cell and neuronal survival when these components are included in the CNS cell culture medium composition of the present invention. Table 1 shows the effect of several combinations of antioxidants on neuronal survival relative to a composition which lacks antioxidants.

Table 1-Antioxidant Effects on CNS Cell Culture Viability

TABLE 1

Antioxidant Effects on CNS Cell Culture Viability

| Ascorbic acid (μM) | Glutathione (mM) | N-acetyl-cystein (μg/ml) | Results (cell viability)* |
|---|---|---|---|
| 400 | — | — | + |
| — | 2 | — | +++ |
| — | — | 50 | + |
| 400 | 2 | — | +++ |
| 400 | — | 50 | ++ |
| — | 2 | 50 | +++ |
| 400 | 2 | 50 | ++++ |

*cell viability is relative to compositions which lack antioxidants.

Table 1 suggests that CNS cell culture medium compositions and CNS cell cryopreservation compositions comprising ascorbic acid, glutathione and N-acetyl cysteine enhance neuronal survival during cell culturing and cell cryopreservation. The results shown in Table 1 are graphically depicted in FIG. 9.

Electrophysiological Characteristics of Cultured, Cryopreserved Neurons Compared to Unfrozen Neurons Patch Clamp electrical recordings are performed on 10 day old cultures of rat cortical neurons treated with the CNS cell cryopreservation composition and stored frozen for 105 days. The recordings are compared to recordings obtained from 10 day old control 'unfrozen' cortical cells, cultured fresh from the same cortex.

The results shown in FIG. 8 suggest that the electrophysiological characteristics of cryopreserved, thawed cortical neurons in culture using the compositions of the present invention are similar to those obtained using 'sister' cultures of unfrozen cells.

Effects of Antioxidants on Glial cells

The effects of the CNS cell culture medium composition and CNS cell cryopreservation composition on CNS cells is shown in FIG. 11B. FIG. 11B suggests that there is an increase in the number of supporting glial cells in culture when CNS cells are cultured and cryopreserved using the CNS compositions of the present invention. Without wishing to be limiting, the CNS cell cultures exhibit an abundance of glia (shown in FIG. 11B in two different focal planes) which appear to form elaborate three dimensional arrays amongst the neuronal cells, similar to that which occurs in vivo (not shown).

Cryopreservation of Murine CNS Cells

The CNS cell cryopreservation and CNS cell culturing compositions of the present invention may be employed to culture and cryopreserve dissociated, murine CNS cells as shown in FIG. 12. The CNS cells shown in FIG. 12, have been cryogenically preserved in the composition of the present invention for a period of about 8.5 months prior to thawing and culturing using the CNS cell culture medium composition of the present invention. Further, the mouse from which the CNS tissue is isolated carries a GFP ubiquitin transgene and all cells, neural and otherwise, are endogenously fluorescent (not shown).

Example 4

Thawing of Frozen Rat Cortex Cells

Rat cortex cells were cryopreserved as described in the previous examples and subjected to one of several thawing protocols including:
1) Thaw one cryovial by gloved hand until thawed. The time to thaw took 4 minutes and 23 seconds.
2) Thaw one cryovial in 37° C. water bath for 5 minutes.
3) Thaw one cryovial in 37° C. water bath for 10 minutes.
4) Thaw one cryovial in 37° C. water bath for 20 minutes.
5) Thaw one cryovial in 56° C. water bath until thawed. In this experiment thawing took 1 minute and 56 seconds.
6) Thaw one cryovial in 56° C. water bath for 2.5 minutes.

Once thawed, the cell suspension was removed and placed in a 15 ml sterile conical tube. Pre-warmed CNS plating media (see Example 1) was added slowly and the cells plated at a density of about 150,000 cells per well in a 96 well plate.
7) Thaw one cryovial in 37° C. water bath for 2.5 minutes. Once thawed, 500 μl of the cell suspension was removed and placed in a 15 ml sterile conical tube. Pre-warmed CNS plating media was added slowly and cells were plated at a plating density of about 150,000 cells per well in a 96 well plate the cryovial containing the remaining cell suspension was placed in a −80° C. freezer for about 1 hour and 20 minutes for refreezing. At this point, the tube was removed from the freezer and re-thawed in a 37° C. water bath for 2.5 minutes. Pre-warmed CNS plating media was added and cells were plated as described above.
8) Store one cryovial at about 4° C. (refrigerator) until thawed. In this experiment thawing took about 70 minutes. Once thawed, about 500 μl of the cell suspension was removed and placed in a sterile 15 ml sterile conical tube. Pre-warmed CNS plating media was added slowly and cells were then plated at a density of 150,000 cells per well in a 96 well plate. The cryovial containing the cell suspension was placed in a −80° C. freezer for 90 minutes for refreezing. At this point, the tube was removed from the freezer and re-thawed in 37° C. water bath for 2.5 minutes. Pre-warmed CNS plating media was added and cells were plated as described above.

On day 4 of culturing, all wells were treated with antioxidant inhibitors (ACG; See Example 1) as described previously and on day 7 all plates were fixed for immunohistochemistry including PGP, GFAP, and Hoechst's staining. These results are shown in FIGS. 13A-H. The results suggest that the cells may be thawed by various methods known in the art without overly influencing cell quality. As expected, none of the cells from the refrozen cell suspension survived.

Example 5

Procedure for Mouse Cortical Dissection

Sterilize dissecting instruments for 20 seconds in the hot bead sterilizer. Place a pregnant animal (about E16) in a Halothane unit and leave until the animal is conscious but "sleepy". Using a cervical dislocator, sacrifice the animal and place the animal on an absorbent disposable sheet. Soak the abdomen of the animal in 70% Ethanol and using the large forceps, pinch and lift the skin of the abdomen. Using the large scissors, cut through the skin of the abdomen. Quickly remove the embryonic sacs and place them in the large petri dish of sterile PBS in the ice bucket. Using the medium forceps, pinch the outside of the sac and using the medium scissors, cut through the sac surrounding the embryo. Transfer the pup into a small sterile petri dish containing sterile PBS on ice. Repeat for the remaining embryos.

Using the medium scissors remove the head from the embryo and place into a new petri-dish containing fresh sterile PBS in the ice bucket. Repeat for the remaining embryos. Transfer the petri dish containing the embryo heads into a laminar flow hood. Place the petri dish on an ice pack covered with a 70% ethanol soaked tissue. Remove one head and place in a new petri-dish containing fresh ice cold sterile PBS. Using the straight tip forceps, pierce the eye sockets of the head and hold against the bottom of the petri-dish. Using the trident scissors, starting at the base of the skull, cut through the skull towards the front of the head keeping the scissors at an upward angle. Use the curved tip forceps to pull each side of the skull to the side to expose the brain.

Use the curve of the curved tip forceps starting at the front of the skull to gently push the brain out of the skull. Use the curved tip forceps to pinch the brain from the base of the skull if it is still attached.

Use the curved tip forceps to scoop (not pinch) the brain to transfer the brain to a new petri-dish containing fresh sterile PBS on the ice pack. Repeat for the remaining heads. Place sterile small petri dishes filled with ice cold sterile PBS on the ice pack and label them Cortex and hippocampus or any other region being collected.

Place one brain in a new 35 mm petri-dish containing ice cold sterile PBS and place under a dissecting microscope set at the lowest level of light coming from below. Refer to the dissection diagram sheet. With the brain ventral (bottom) side up, use one curved tip forcep to pierce the center of the brain to hold it to the bottom of the petri-dish. Using the second curved tip forcep remove the olfactory bulbs.

Peel off the membrane surrounding the brain that contains the blood vessels (pia matter). Flip the brain over (dorsal side up), again pierce the center of the brain and remove any remaining membrane. Fold out one side of the brain and using the curved tip forceps remove the hippocampus, septum and the striatum. Pinch off the isolated cortex and place in the petri-dish containing fresh sterile PBS that is sitting on ice. Repeat for the other half of the brain.

Repeat the above procedure for any remaining brains. Change the PBS in the dissection dish (under the microscope) after every second brain dissected with fresh ice cold sterile PBS.

Once all cortices have been isolated, transfer the dishes to a biological safety hood and use a sterile 10 ml pipet to gently transfer the cortices to a sterile 50 nm conical tube, avoiding air bubbles. Make note of the volume transferred. Place a maximum of 16 cortices per tube (8 whole brains).

Add a volume of ice cold CNS plating media equal to the volume already in the tube. Place the tube on ice. Repeat for any remaining tubes. Centrifuge the tubes at 1100 rpm for 6 min.

After centrifugation remove the supernatant from the 50 ml tube using the pump and a Pasteur pipette. To the 50 ml tube containing the cortices, add sterile CNS plating media (CNS cell culture medium composition (see Example 1) lacking antioxidants) to a volume equal to 1 ml per brain less one ml (ie, if there are 16 cortices in the tube add media to a final volume of 7 ml). Place the tubes on ice.

Using a 10 ml sterile pipette triturate (aspirate and dispense) the cortices 13 times. Look at the suspension and if there are large pieces of cortex remaining triturate a few more times to a maximum of 18 times, avoiding air bubbles. Let the tube sit on ice for 1 min to allow the large pieces to settle at the bottom of the tube.

Transfer the supernatant with a sterile 10 ml pipette to a new sterile 50 ml conical tube without disturbing the large pieces at the bottom of the tube. Make note of the volume of supernatant transferred. Place the tube on ice. Add the supernatant from any additional tubes to the same tube.

Invert the tube gently several times to ensure an even dispersion of cells in suspension. Remove 50 µL of the cell suspension and count the cells. Remove the volume of cell suspension needed to plate fresh cultures. Centrifuge the remaining cells suspension at 1100 rpm for 6 min. Using the pump and a sterile glass Pasteur pipette remove the supernatant. To the cell pellet add the volume of CNS cell cryopreservation composition media that results in 4 million cells per ml. Mix very gently until cell pellet is resuspended. Aliquot 1 ml per vial. Transfer the vials to the programmable freezing unit and freeze the cells using the Programmable Freezing Unit SOP.

Fresh Cultures

Once the cell count has been determined, plate cells for fresh culture verification (500,000 cells per well in 24-well culture plates or 100,000 cells per well of 96-well plate). 24 hours after plating change the media with fresh 37° C. CNS plating media On day 4 of culture, change media with fresh 37° C. CNS plating media with mitotic inhibitors.

Culturing of Previously Cryopreserved Cells

Thaw a vial of cells at 37° C. for 2.5 minutes. Transfer the cells to a 15 ml conical tube and slowly add 3 ml CNS plating media warmed to 37° C. Plate 1 ml cell suspension per well of a 24-well plate on Matrigel coated coverslips. Remove the media 4 hours later and replace with 1 ml 37° C. CNS plating media. On day 4 of culture add media with inhibitors as per fresh cultures.

Figure 14A:
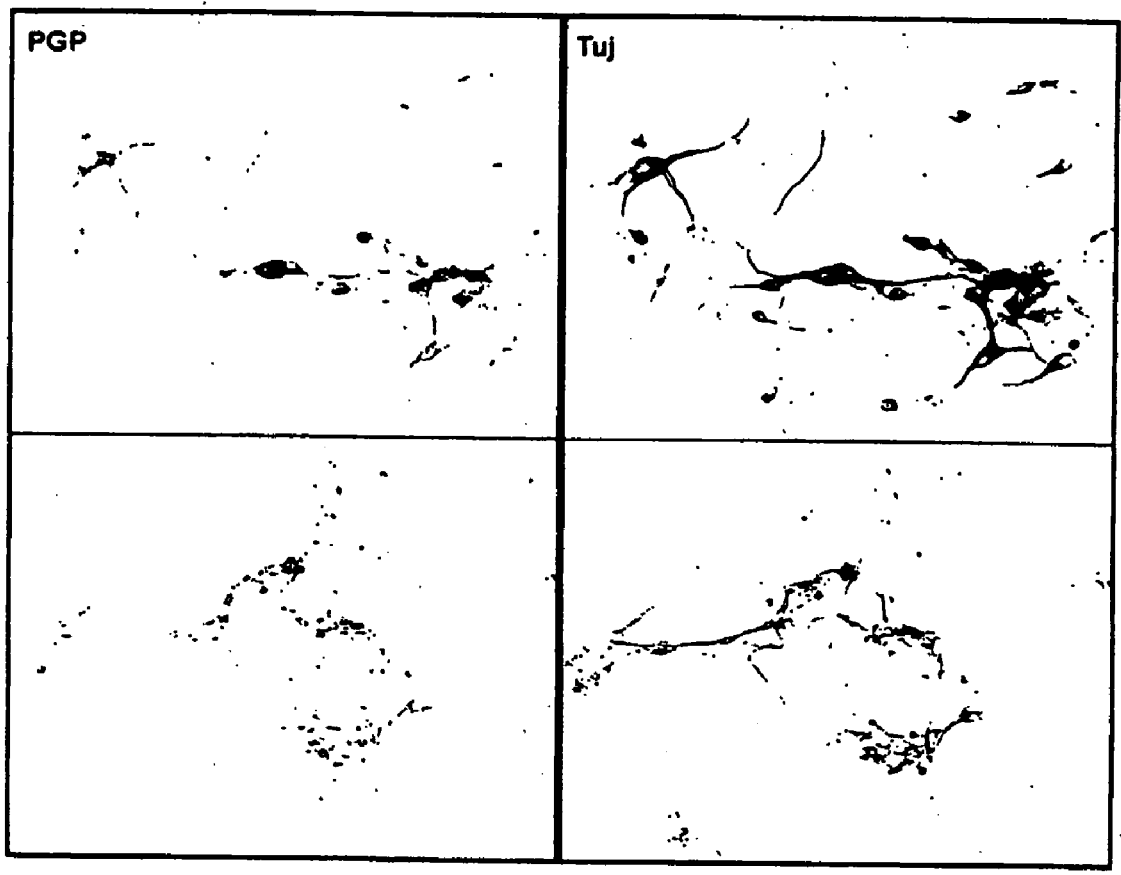
FIG. 14A: PGP and Tuj staining of frozen mouse cortex (embryonic day 16), following thawing and 7 day culture in CNS cell culture composition comprising ACG antioxidants.
Figure 14B:
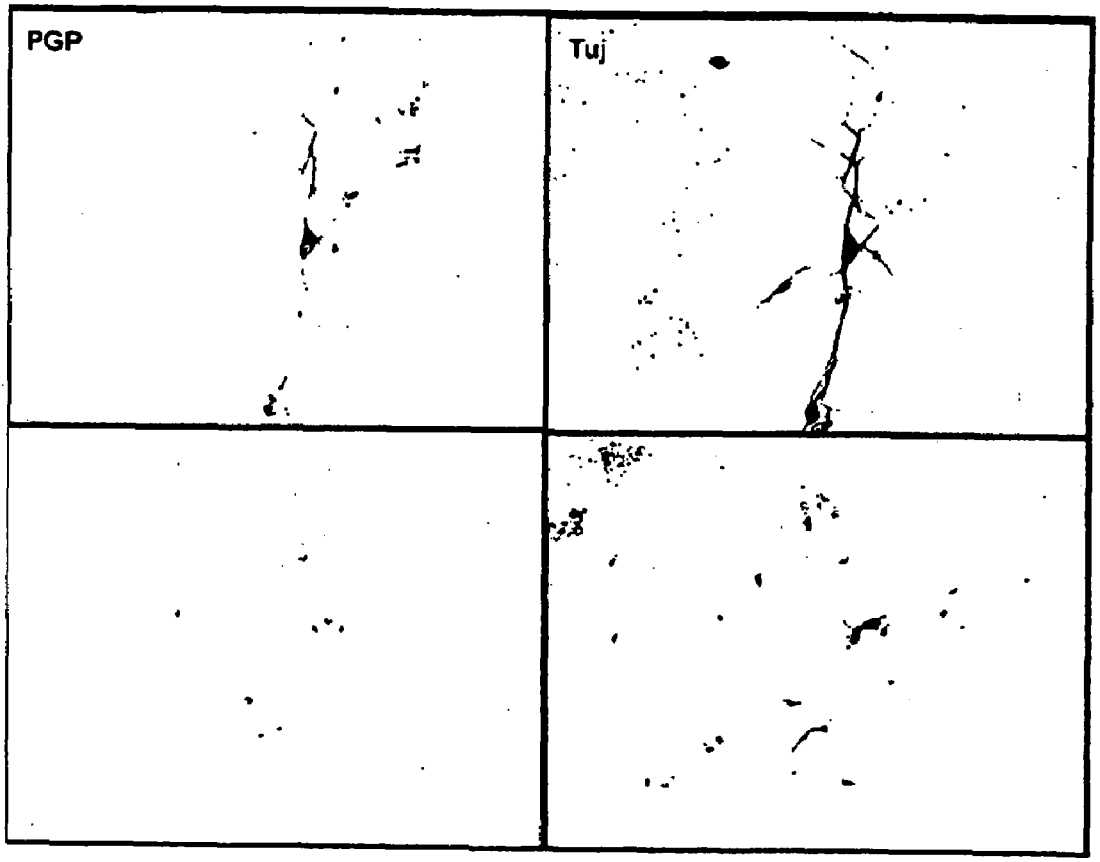
FIG. 14B: PGP and Tuj staining of frozen mouse cortex (embryonic day 19), following thawing and 7 day culture in CNS cell culture composition comprising ACG antioxidants.
Figure 14C:
FIG. 14C: cell micrographs of fresh hippocampus from postnatal day 1, and embryonic mouse cortex (day 18/19) maintained in CNS cell culture composition for 7 days in CNS plating medium.
Figure 14C:
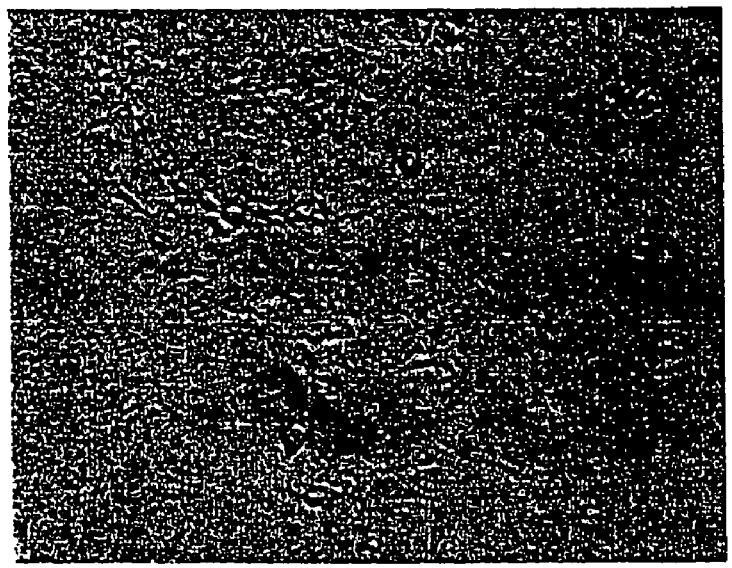
Figure 14D:
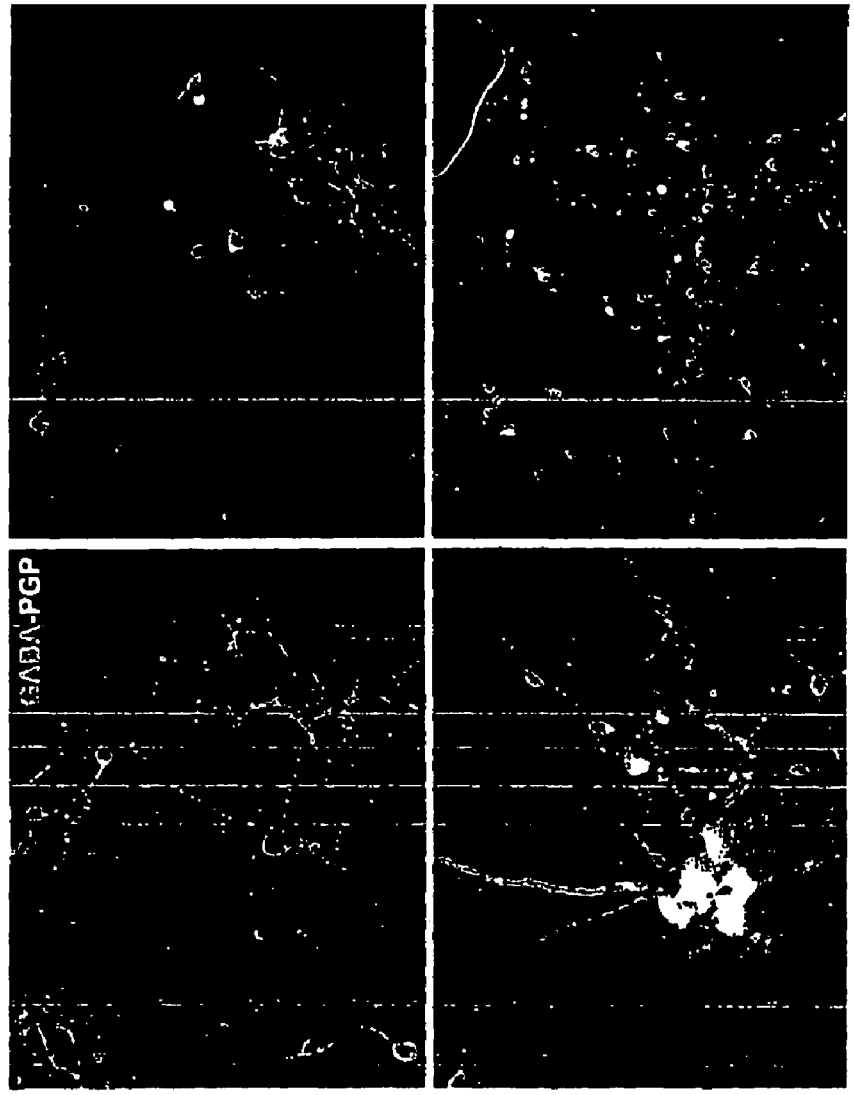
FIG. 14D: GABA-PGP staining of frozen mouse cortex E16 cells cultured for 7 days in vitro.
Figure 14E:
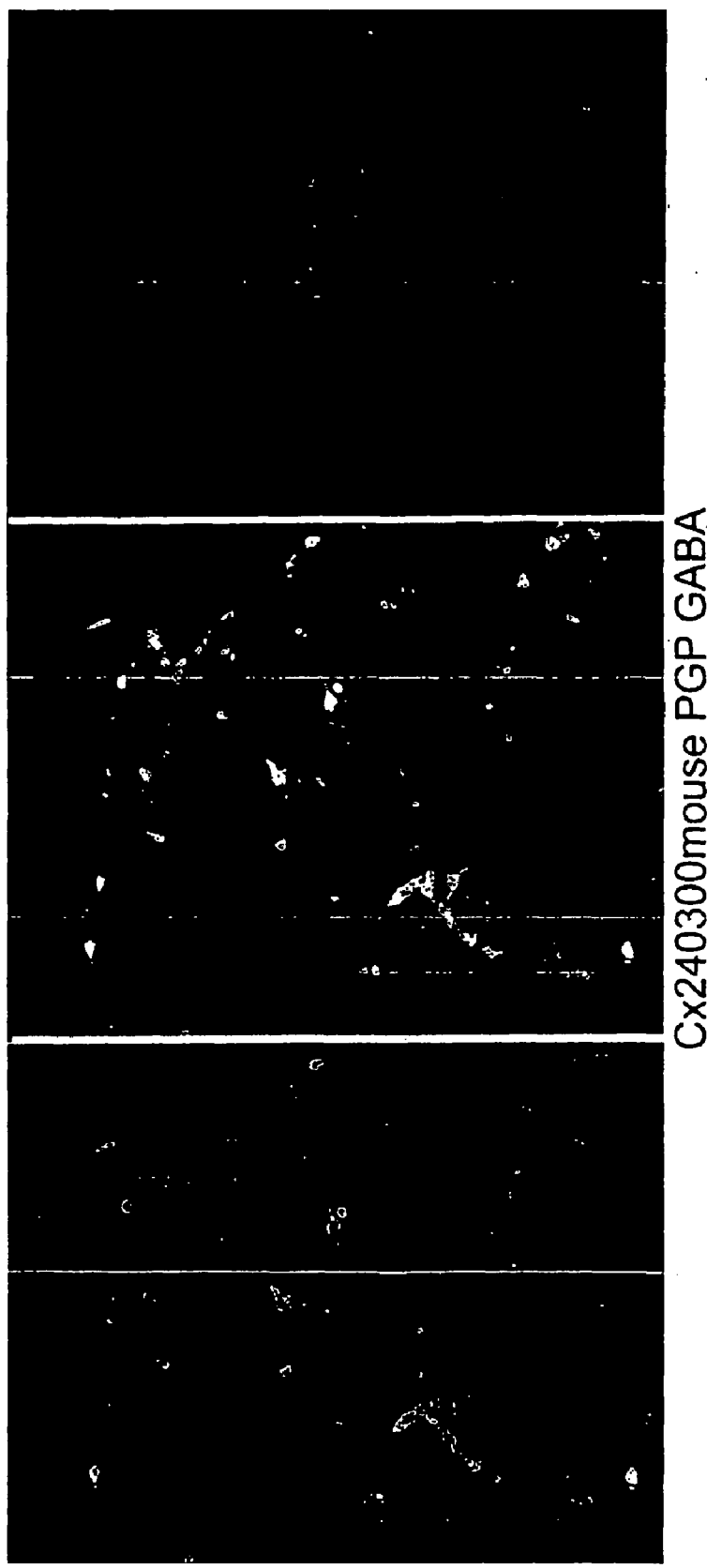
FIG. 14E: PGP-GABA staining of mouse cortical cells.

Referring now to FIGS. 14A-E there is shown PGP and Tuj staining of cryopreserved mouse cortex (embryonic day 16) cultured for 7 days post thaw in CNS cell culture medium composition comprising ACG antioxidants [FIG. 14A], and cryopreserved mouse cortex (embryonic day 19) cultured for 7 days post thaw in CNS cell culture medium composition comprising ACG antioxidants [FIG. 14B]. FIG. 14C shows microscopy photographs of fresh mouse hippocampus (post natal day 1) and fresh mouse cortex (embryonic day 18/19) maintained in CNS plating media at a density of about 500,000 cells/ml. FIGS. 14D and E show GABA-PGP staining of mouse cortical cell cultures.

The results shown in FIGS. 14A-E indicate that the cryopreservation and cell culture compositions of the present invention may be employed in the cryopreservation and cell culturing of mouse cortical cells. Further, the cells may be derived from embryonic or post natal cortices. Preferably, embryonic cortical cells are obtained from about day 16 (E16) embryos. However, embryonic cortical cells of other ages may also be employed by the present invention.

Example 6

Procedure for Mouse Hippocampus Dissection

Sterilize dissecting instruments for 20 seconds in the hot bead sterilizer.

Place a pregnant animal in a Halothane unit and leave until the animal is conscious but "sleepy".

Using a cervical dislocator, sacrifice the animal and place the animal on an absorbent disposable sheet.

Soak the abdomen of the animal in 70% Ethanol and using the large forceps, pinch and lift the skin of the abdomen. Using the large scissors, cut through the skin of the abdomen. Quickly remove the embryonic sacs and place them in the large petri dish of sterile PBS in the ice bucket.

Using the medium forceps, pinch the outside of the sac and using the medium scissors, cut through the sac surrounding the embryo. Transfer the pup into a small sterile petri dish containing sterile PBS on ice. Repeat for the remaining embryos.

Using the medium scissors remove the head from the embryo and place into a new petri-dish containing fresh sterile PBS in the ice bucket. Repeat for the remaining embryos.

Transfer the petri dish containing the embryo heads into a laminar flow hood. Place the petri dish on an ice pack covered with a 70% ethanol soaked tissue. Remove one head and place in a new petri-dish containing fresh ice cold sterile PBS. Using the straight tip forceps, pierce the eye sockets of the head and hold against the bottom of the petri-dish. Using the trident scissors, starting at the base of the skull, cut through the skull towards the front of the head keeping the scissors at an upward angle. Use the curved tip forceps to pull each side of the skull to the side to expose the brain.

Use the curve of the curved tip forceps starting at the front of the skull to gently push the brain out of the skull. Use the curved tip forceps to pinch the brain from the base of the skull if it is still attached.

Use the curved tip forceps to scoop (not pinch) the brain to transfer the brain to a new petri-dish containing fresh sterile PBS on the ice pack. Repeat for the remaining heads. Place sterile small petri dishes filled with ice cold sterile PBS on the ice. Place one brain in a new 35 mm petri-dish containing ice cold sterile PBS and place under a dissecting microscope set at the lowest level of light coming from below. Refer to the dissection diagram sheet. With the brain ventral (bottom) side up, use one curved tip forcep to pierce the center of the brain to hold it to the bottom of the petri-dish. Using the second curved tip forcep remove the olfactory bulbs.

Peel off the membrane surrounding the brain that contains the blood vessels (pia matter). Flip the brain over (dorsal side up), again pierce the center of the brain and remove any remaining membrane. Fold out one side of the brain and using the curved tip forceps remove the hippocampus. Transfer the isolated hippocampus to a petri-dish containing fresh sterile PBS that is sitting on ice. Repeat for the other half of the brain.

Repeat the above procedure for any remaining brains. Change the PBS in the dissection dish (under the microscope) after every second brain dissected with fresh ice cold sterile PBS. Once all the hippocampus has been isolated, transfer the dishe to a biological safety hood and use a sterile 10 ml pipet to gently transfer the tissue to a sterile. 15 ml conical tube, avoiding air bubbles. Make note of the volume transferred.

Add a volume of ice cold CNS plating media equal to the volume already in the tube. Centrifuge the tubes at 1100 rpm for 6 min.

After centrifugation remove the supernatant from the 15 ml tube using the pump and a Pasteur pipette. To the 15 ml tube containing the tissue, add 2 ml sterile CNS plating media. Using a sterile flamed tipped Pasteur pipette triturate (aspirate and dispense) the tissue 13 times. Look at the suspension and if there are large pieces of tissue remaining triturate a few more times to a maximum of 18 times, avoiding air bubbles. Let the tube sit on ice for 1 min to allow the large pieces to settle at the bottom of the tube.

Transfer the supernatant with a sterile flamed tipped Pasteur pipette to anew sterile 15 ml conical tube without disturbing the large pieces at the bottom of the tube. Make note of the volume of supernatant transferred.

Invert the tube gently several times to ensure an even dispersion of cells in suspension. Remove 50 µL of the cell suspension and count the cells. Remove the volume of cell suspension needed to plate fresh cultures. Centrifuge the remaining cells suspension at 1100 rpm for 6 min. Using the pump and a sterile glass Pasteur pipette remove the supernatant. To the cell pellet add the volume of Cryoprotectant media that results in 4 million cells per ml. Mix very gently until cell pellet is resuspended. Aliquot 1 ml per vial. Transfer the vials to the programmable freezing unit and freeze the cells using the Programmable Freezing Unit.

Fresh Cultures

Once the cell count has been determined, plate cells for fresh culture verification (500,000 cells per well in 24-well culture plates or 100,000 cells per well of 96-well plate). 24 hours after plating change the media with fresh 37° C. CNS plating media (see Example 1). On day 4 of culture, change media with fresh 37° C. CNS plating media with inhibitors as described previously.

Culturing of Previously Cryopreserved Cells

Thaw a vial of cells at 37° C. for 2.5 minutes. Transfer the cells to a 15 ml conical tube and slowly add 4.3 ml CNS plating media warmed to 37° C. Plate 1 ml cell suspension per well of a 24-well plate on Matrigel coated coverslips. Remove the media 4 hours later and replace with 1 ml 37° C. CNS plating media. On day 4 of culture add media with inhibitors as per fresh cultures.

Figure 15A:
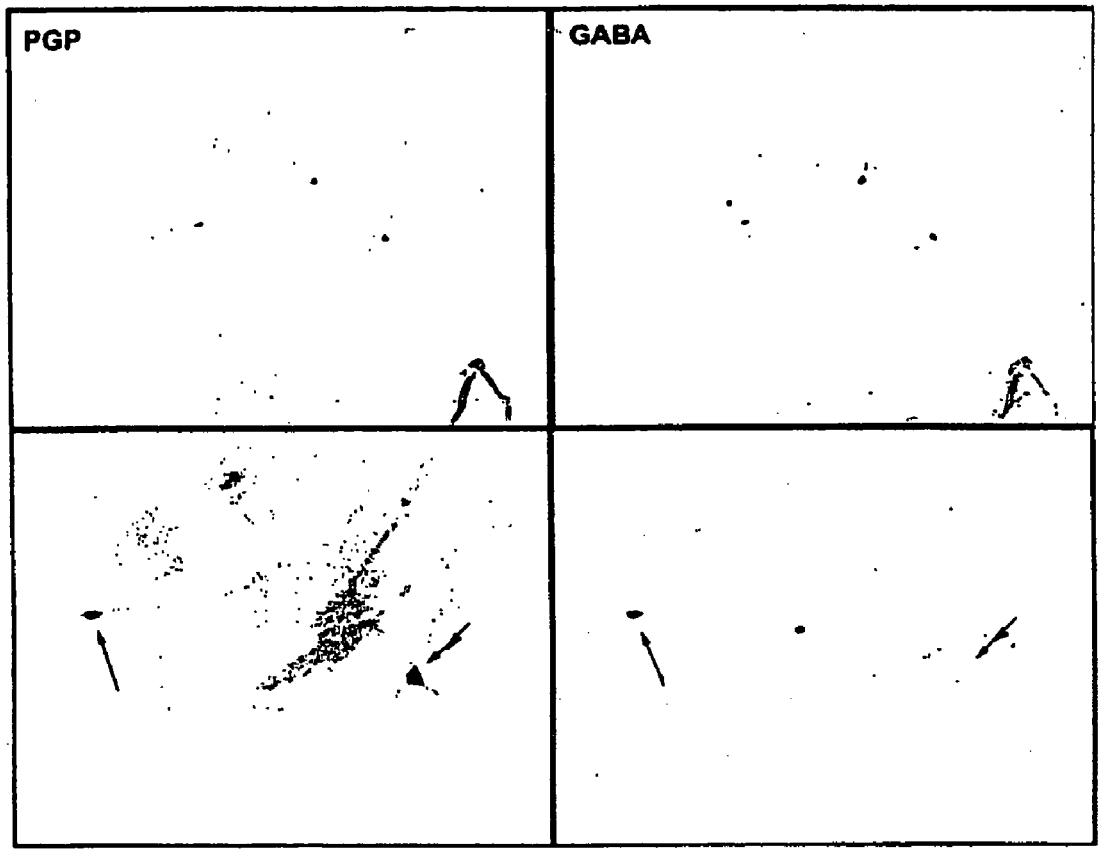
FIG. 15A shows PGP and GABA staining of postnatal day 1 cryopreserved mouse hippocampal cells cultured for 7 days in CNS cell culture composition lacking ACG antioxidants.
Figure 15B:
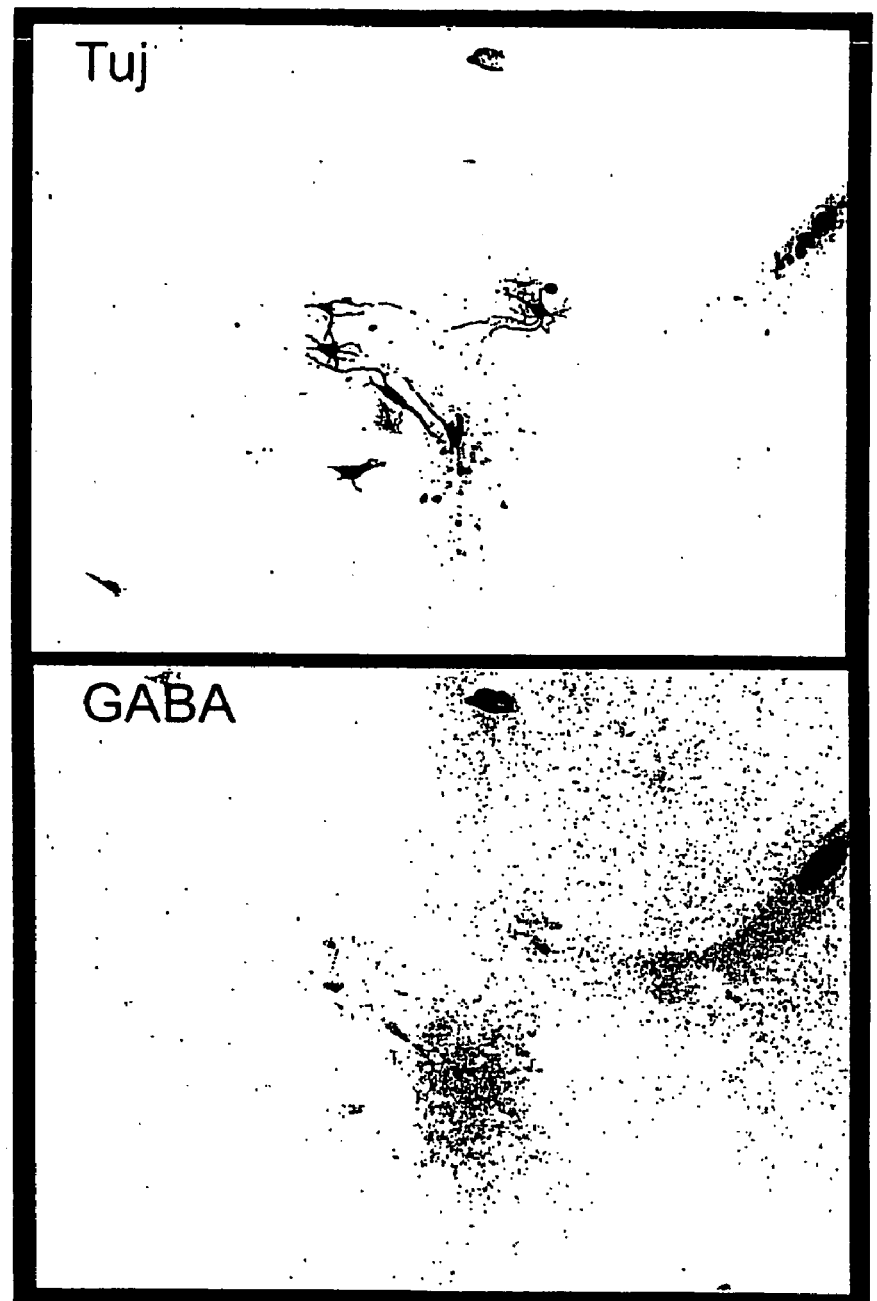
FIG. 15B shows Tuj and GABA staining of embryonic day 18/19 cryopreserved mouse hippocampal cells cultured for 7 days in CNS cell culture composition lacking ACG antioxidants.
Figure 15C:
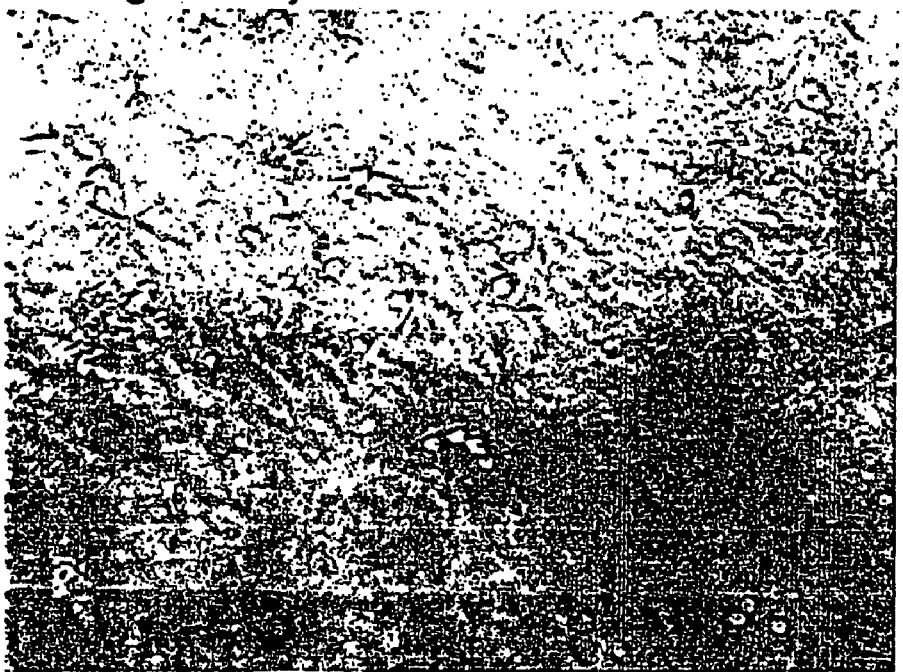
FIG. 15 shows results obtained following cryopreservation of mouse hippocampal cells.
FIG. 15D shows GABA-PGP staining of cryopreserved mouse hippocampal post-natal day 1 cells cultured for 7 days in CNS cell culture composition medium.
Figure 15C:
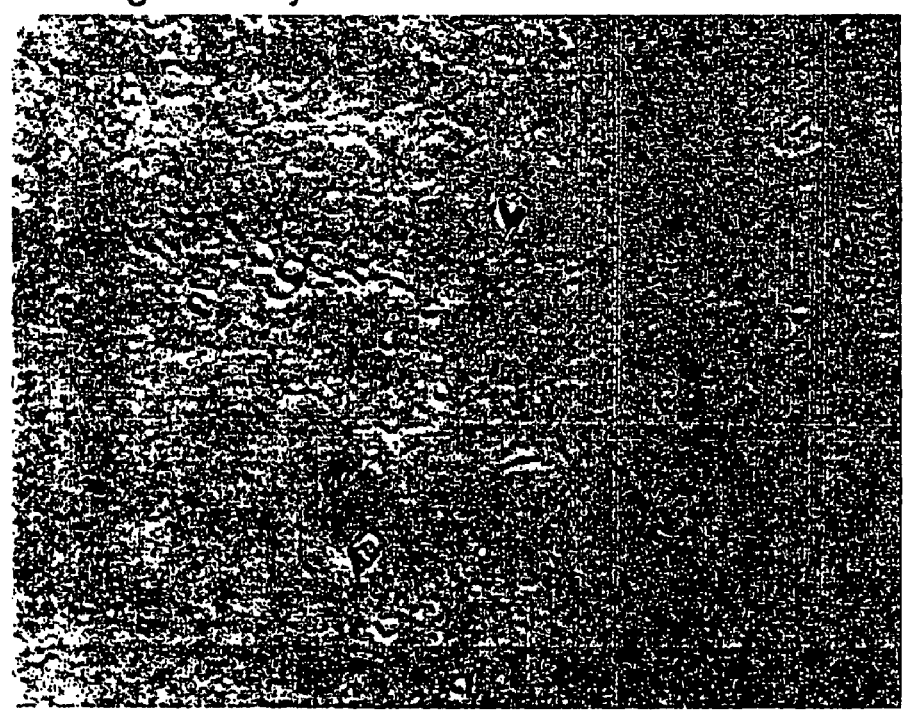
Figure 15D:
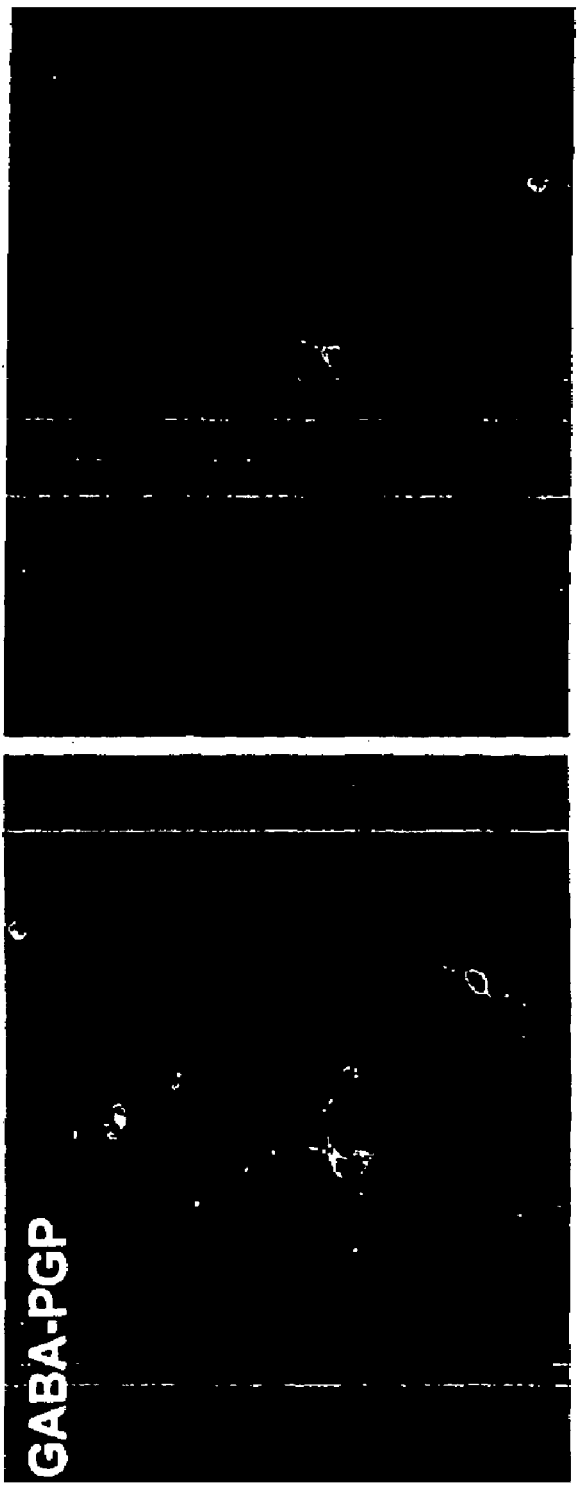

Referring now to FIGS. 15A-D there is shown results of mouse hippocampal cells cryopreserved and cultured using the cryopreservation and cell culture compositions of the present invention. Shown in FIG. 15A is PGP and GABA staining of frozen mouse hippocampal cells (postnatal day 1) following thawing and culturing for 7 days in CNS cell culture media comprising ACG antioxidants. FIG. 15B shows results of Tuj and Gaba staining of cryopreserved hippocampal cells (embryonic day 18/19) following thawing and culturing for 7 days in CNS cell culture media comprising ACG antioxidants. FIG. 15C shows cell micrographs of fresh mouse hippocampal and mouse cortex cells of post natal day 1 and embryonic day 18/19 age respectively, maintained in CNS plating media at a density of about 500 000 cells/ml. FIG. 15D shows GABA-PGP staining of cryopreserved mouse hippocampal cells (day 1 postnatal). Collectively these results indicate that the cryopreservation compositions and the cell culture compositions may be employed in the cryopreservation and culturing of mouse hippocampus cells of post natal or embryonic origin. In an aspect of an embodiment, the hippocampus cells are embryonic day 18/19 cells or day 1 postnatal cells. However, cells of other ages may also be cryopreserved and cultured using the compositions as disclosed herein.

Example 7

Procedure for Rat Hippocampus Dissection

Sterilize dissecting instruments for 20 seconds in the hot bead sterilizer. Place a pregnant animal (E18/19) in a Halothane unit and leave until the animal is conscious but "sleepy".

Using a cervical dislocator, sacrifice the animal and place the animal on an absorbent disposable sheet.

Soak the abdomen of the animal in 70% Ethanol and using the large forceps, pinch and lift the skin of the abdomen. Using the large scissors, cut through the skin of the abdomen. Quickly remove the embryonic sacs and place them in the large petri dish of sterile PBS in the ice bucket.

Using the medium forceps, pinch the outside of the sac and using the medium scissors, cut through the sac surrounding the embryo. Transfer the pup into a small sterile petri dish containing sterile PBS on ice. Repeat for the remaining embryos.

Using the medium scissors remove the head from the embryo and place into a new petri-dish containing fresh sterile PBS in the ice bucket. Repeat for the remaining embryos.

Transfer the petri dish containing the embryo heads into a laminar flow hood. Place the petri dish on an ice pack covered with a 70% ethanol soaked tissue. Remove one head and place in a new petri-dish containing fresh ice cold sterile PBS. Using the straight tip forceps, pierce the eye sockets of the head and hold against the bottom of the petri-dish.

Using the trident scissors, starting at the base of the skull, cut through the skull towards the front of the head keeping the scissors at an upward angle. Use the curved tip forceps to pull each side of the skull to the side to expose the brain.

Use the curve of the curved tip forceps starting at the front of the skull to gently push the brain out of the skull. Use the curved tip forceps to pinch the brain from the base of the skull if it is still attached.

Use the curved tip forceps to scoop (not pinch) the brain to transfer the brain to a new petri dish containing fresh sterile PBS on the ice pack. Repeat for the remaining heads. Place sterile small petri dishes filled with ice cold sterile PBS on the ice. Place one brain in a new 35 mm petri-dish containing ice cold sterile PBS and place under a dissecting microscope set at the lowest level of light coming from below. Refer to the dissection diagram sheet. With the brain ventral (bottom) side up, use one curved tip forcep to pierce the center of the brain to hold it to the bottom of the petri-dish. Using the second curved tip forcep remove the olfactory bulbs.

Peel off the membrane surrounding the brain that contains the blood vessels (pia matter). Flip the brain over (dorsal side up), again pierce the center of the brain and remove any remaining membrane. Fold out one side of the brain and using the curved tip forceps remove the hippocampus. Transfer the isolated hippocampus to a petri-dish containing fresh sterile PBS that is sitting on ice. Repeat for the other half of the brain.

Repeat the above procedure for any remaining brains. Change the PBS in the dissection dish (under the microscope) after every second brain dissected with fresh ice cold sterile PBS.

Once all the hippocampus has been isolated, transfer the dish to a biological safety hood and use a sterile 10 ml pipet to gently transfer the tissue to a sterile 15 ml conical tube, avoiding air bubbles. Make note of the volume transferred.

Add a volume of ice cold CNS plating media equal to the volume already in the tube. Centrifuge the tubes at 1100 rpm for 6 min.

After centrifugation remove the supernatant from the 15 ml tube using the pump and a Pasteur pipette. To the 15 ml tube containing the tissue, add 2 ml sterile CNS plating media Using a sterile flamed tipped Pasteur pipette triturate (aspirate and dispense) the tissue 13 times. Look at the suspension and if there are large pieces of tissue remaining triturate a few more times to a maximum of 18 times, avoiding air bubbles. Let the tube sit on ice for 1 min to allow the large pieces to settle at the bottom of the tube.

Transfer the supernatant with a sterile flamed tipped Pasteur pipette to a new sterile 15 ml conical tube without disturbing the large pieces at the bottom of the tube. Make note of the volume of supernatant transferred.

Invert the tube gently several times to ensure an even dispersion of cells in suspension. Remove 50 µL of the cell suspension and count the cells. Remove the volume of cell suspension needed to plate fresh cultures. Centrifuge the remaining cells suspension at 1100 rpm for 6 min. Using the pump and a sterile glass Pasteur pipette remove the supernatant. To the cell pellet add the volume of CNS cell cryopreservation composition that results in 4 million cells per ml. Mix very gently until cell pellet is resuspended. Aliquot 1 ml per vial. Transfer the vials to the programmable freezing unit and freeze the cells using the Programmable Freezing Unit.

Fresh Cultures

Once the cell count has been determined, plate cells for fresh culture verification at 300,000 cells/ml in 37° C. CNS plating media+ACG (see Example 1). 24 hours after plating change the media with fresh 37° C. CNS plating media. On day 4 of culture, change media with fresh 37° C. CNS plating media with inhibitors as described previously.

Culturing of Previously Cryopreserved Cells

Thaw a vial of cells at 37° C. for 2.5 minutes. Transfer the cells to a 15 ml conical tube and slowly add 9 ml CNS plating media+ACG warmed to 37° C. Plate 1 ml cell suspension per well of a 24-well plate on Matrigel coated coverslips for a plating density of 400,000 cells/ml. Remove the media 4 hours later and replace with 1 ml 37° C. CNS plating media On day 4 of culture add media with inhibitors as per fresh cultures.

Figure 16A:
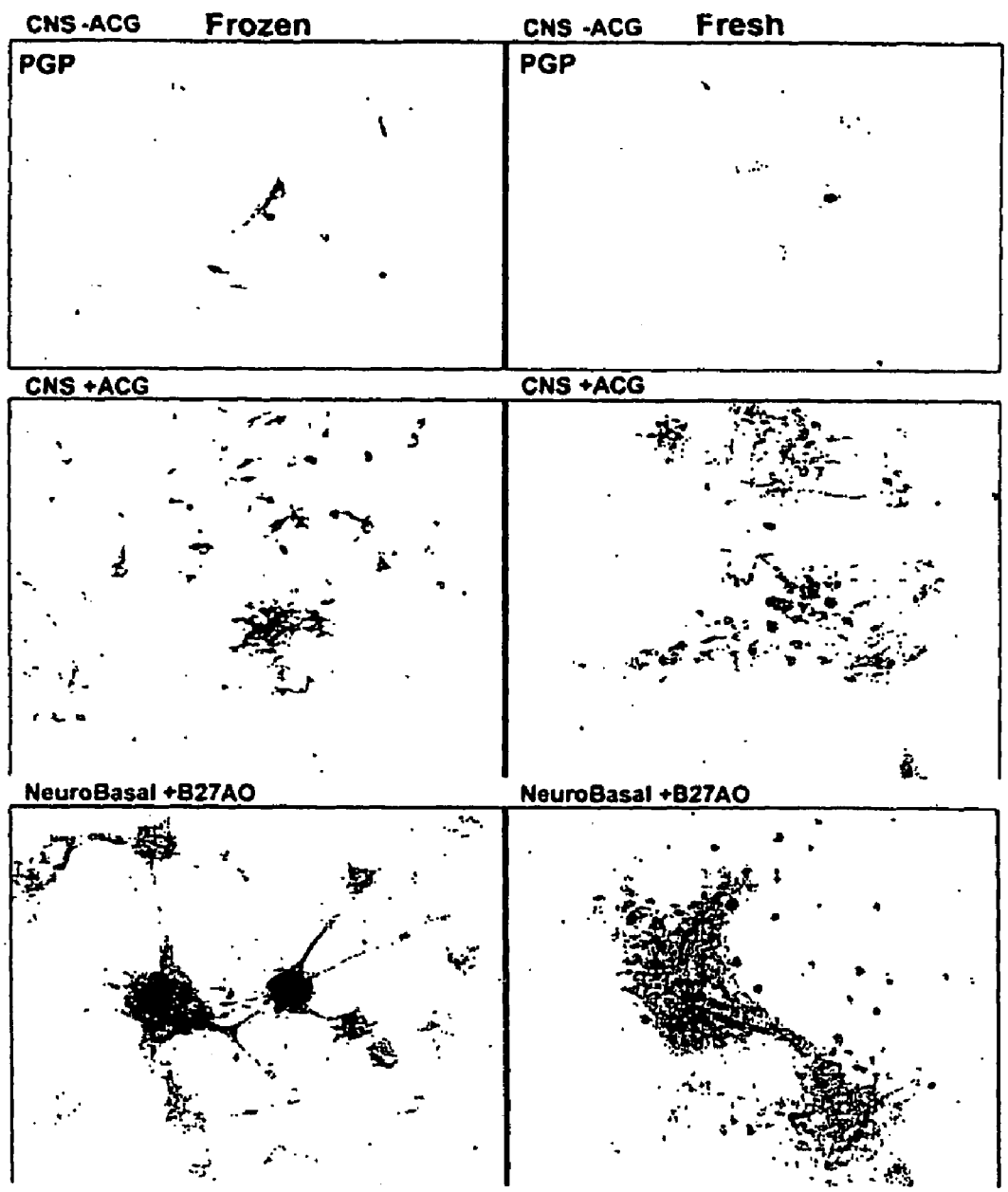
FIG. 16A shows PGP staining of fresh or cryopreserved rat hippocampus cells (embryonic day 18/19) maintained in culture for 7 days with either cell culture medium lacking ACG antioxidants, comprising AGC antioxidants, or Neurobasal medium with B27 (comprising antioxidants) or Neurobasal medium with B27 lacking antioxidants.

Referring now to FIGS. 16A-E, there is shown results of cryopreserving rat hippocampus cells using the cell cryopreservation and cell culture compositions of the present invention. Shown in FIG. 16A are comparative photomicrographs depicting PGP staining from rat hippocampus cells (embryonic day 18/19) from cryopreserved and freshly dissected specimens treated with CNS cell culture medium composition of the present invention with and without antioxidants (ACG; see Example 1). Also shown is the effect of B27 supplemented NeuroBasal medium on the cells. The results suggest that rat hippocampus cells may be cryopreserved and cultured using the cell cryopreservation and cell culture compositions of the present invention.

Figure 16B:
FIG. 16B shows PGP and GABA staining of cryopreserved rat hippocampal cells (embryonic day 18/19) maintained in culture for 7 days with Neurobasal media with B27 comprising antioxidant.
Figure 16C:
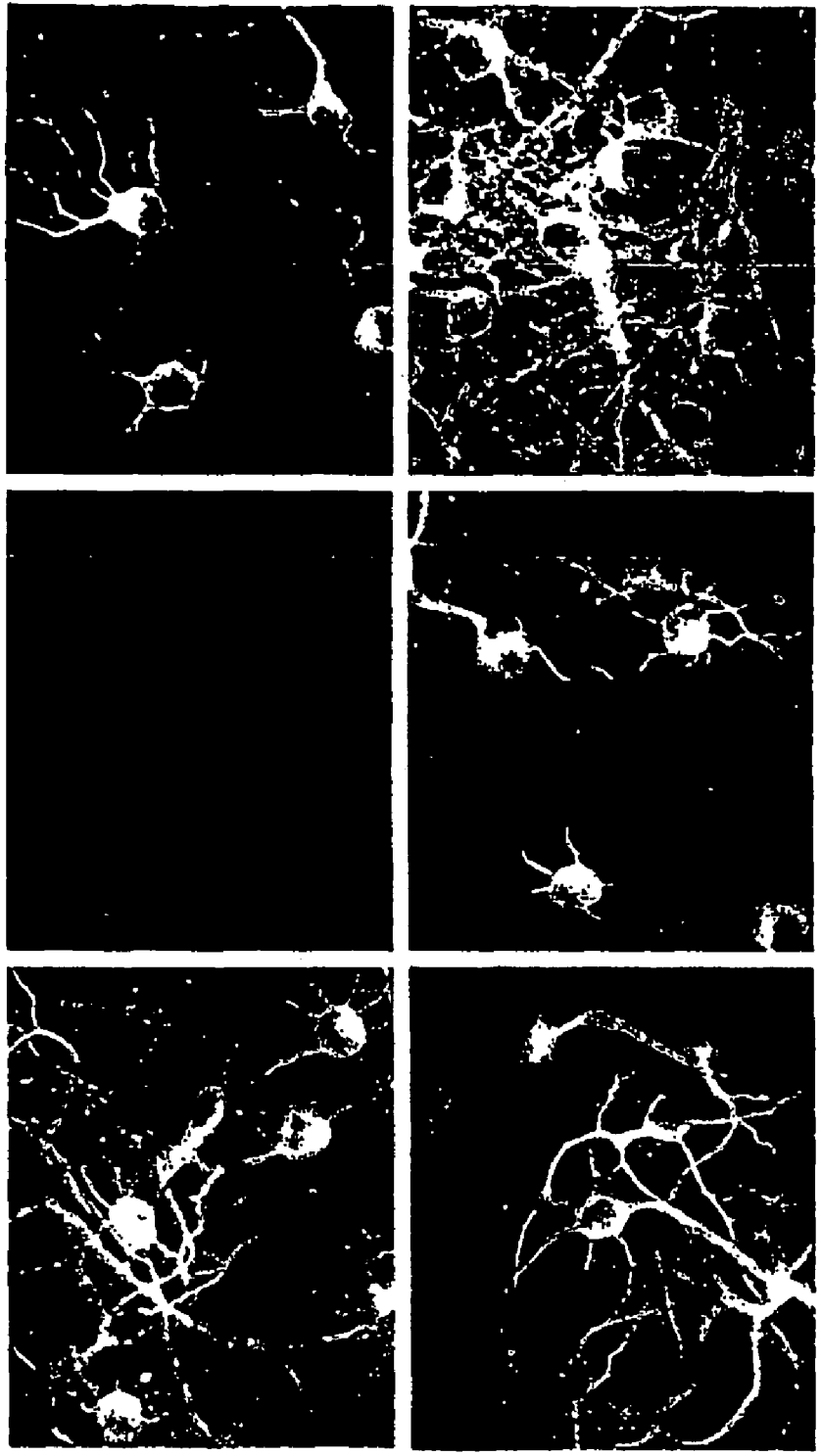
FIG. 16C shows staining of cryopreserved rat hippocampal neurons maintained in Neurobasal medium with B27 comprising antioxidants.

FIG. 16B shows PGP and GABA staining of cryopreserved rat hippocampus cells (embryonic day 18/19) after thawing and maintained in neurobasal medium with B27 plus antioxidants. FIG. 16C shows staining of rat hippocampus neurons following cryopreservation and culturing in Neurobasal medium comprising B27 and antioxidants.

Thus, in an aspect of an embodiment, cells such as, but not limited to rat hippocampus cells are cryopreserved, cultured or both cryopreserved and cultured with cell cryopreservation medium comprising ACG as described in Example 1. In an alternate embodiment, cells such as, but not limited to rat hippocarnpus cells are cryopreserved, cultured or both cryopreserved and cultured with Neurobasal medium comprising B27 antioxidant.

All references are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A cryopreservation composition for cryopreserving non-proliferative primary neuronal cells from the CNS comprising nutrient medium, serum, D-glucose, L-glutamine, an antibiotic, a cryopreservative, and three antioxidants comprising ascorbic acid, glutathione, and N-acetylcysteine, wherein the composition comprises about 20% (v/v) serum, about 2 mM glutamine, about 20 mM glucose, about 1 U/ml penicillin-streptomycin, about 400 mM ascorbic acid, about 2 mM glutathione, about 300 mM N-acetylcysteine and about 80% (v/v) dimethylsulfoxide (DMSO).

2. The composition of claim 1, wherein said nutrient medium comprises minimal essential medium, or Neurobasal medium.

3. The composition of claim 1, wherein said serum comprises about 10% (v/v) horse serum and about boo (v/v) fetal bovine serum.

4. The composition of claim 1, further comprising at least one mitotic inhibitor.

5. The composition of claim 4, wherein said at least one mitotic inhibitor comprises fluorodeoxyuridine, cytosine arabinoside, uridine triphosphate or a combination thereof.

6. The composition of claim 5, wherein said fluorodeoxyuridine is present in an amount of about 10 mM.

7. The composition of claim 5, wherein said cytosine arabinoside is present in an amount of about 1 mM.

8. The composition of claim 5, wherein said uridine triphosphate is present in an amount of about 0.5 mM.

9. The composition of claim 5, wherein said composition comprises flurodeoxyuridine, cytosine arabinoside, and uridine triphosphate.

10. The composition of claim 9, wherein flurodeoxyuridine is present in an amount of about 10 mM, cytosine arabinoside is present in an amount of about 1 mM and uridine triphosphate is present in an amount of about 0.5 mM.

11. The composition of claim 1, further comprising primary neuronal cells.

12. The composition of claim 11, wherein the neuronal cells are dorsal root ganglion neurons.

13. The composition of claim 11, wherein said primary neuronal cells are cryopreserved in said composition.

* * * * *